US008034388B2

(12) United States Patent
Magnuson et al.

(10) Patent No.: US 8,034,388 B2
(45) Date of Patent: Oct. 11, 2011

(54) ANTHOCYANIN-RICH COMPOSITIONS AND METHODS FOR INHIBITING CANCER CELL GROWTH

(75) Inventors: Bernadene Ann Magnuson, Columbia, MD (US); M. Monica Giusti, Dublin, OH (US); Minnie Malik, Olney, OH (US); Cuiwei Zhao, Ellicott City, MD (US)

(73) Assignee: The University of Maryland, Riverdale, MD (US)

( * ) Notice: Subject to any disclaimer, the term of this patent is extended or adjusted under 35 U.S.C. 154(b) by 251 days.

(21) Appl. No.: 11/388,163

(22) Filed: Mar. 23, 2006

(65) Prior Publication Data

US 2006/0159781 A1    Jul. 20, 2006

Related U.S. Application Data

(63) Continuation of application No. 10/795,967, filed on Mar. 8, 2004, now abandoned.

(60) Provisional application No. 60/452,600, filed on Mar. 6, 2003.

(51) Int. Cl.
*A61K 36/00* (2006.01)
*A61K 36/73* (2006.01)
*A61K 36/45* (2006.01)

(52) U.S. Cl. ........................ 424/732; 424/725

(58) Field of Classification Search ........................ None
See application file for complete search history.

(56) References Cited

U.S. PATENT DOCUMENTS

| 6,656,914 | B2 * | 12/2003 | Nair et al. ...................... 424/725 |
| 6,818,234 | B1 | 11/2004 | Nair et al. |
| 2001/0016573 | A1 | 8/2001 | Nair et al. |
| 2001/0049349 | A1 | 12/2001 | Chinery et al. |
| 2002/0054924 | A1 * | 5/2002 | Leahy et al. .................. 424/732 |
| 2002/0182270 | A1 * | 12/2002 | Stier et al. ...................... 424/725 |
| 2003/0031734 | A1 | 2/2003 | Rosen |
| 2006/0024392 | A1 | 2/2006 | Magnuson et al. |

FOREIGN PATENT DOCUMENTS

JP    2001172191    *    6/2001

OTHER PUBLICATIONS

Chen et al., Induction of G1 phase arrest in MCF human breast cancer cells by pentagalloylglucose through the down-regulation of CDK4 and CDK2 activities and up-regulation of the CDK inhibitors p27(Kip) and p21(Cip).Biochemical Pharmacology 65 (11): 1777-85, 2003.*
Koide et al., Influence of flavonoids on cell cycle phase as analyzed by flow-cytometry. Cancer Biotherapy & Radiopharmaceuticals 12 (2): 111-115, 1997.*
Kaack et al., Black chokeberry (*Aronia melanocarpa*) for manufacture of a food colorant. Tidsskr. Planteavl 96: 183-196, 1992.*
Lin et al., Distinct molecular pathways mediate progesterone-induced growth inhibition and focal adhesion. Endocrinology, 144 (12): 5650-7, 2003.*
Kamei et al (Cancer Biotherapy & Radiopharmaceuticals 11 (4): 247-249, 1996).*
Wu et al (Journal of agricultural and food chemistry, (May 31, 2006), vol. 54, No. 11, pp. 4069-4075).*
Kamb, Nature Reviews, 4: 161-165, 2005.*
Definition of food coloring from Wikipedia, pp. 1-5, accessed on Nov. 28, 2009.*
Introduction of cancer from Merck Manual, accessed on Feb. 23, 2010, pp. 1-3.*
Appel et al, Metabolic stability of experimental chemotherapeutic agents in hepatocyte:tumor cell co-cultures, Cancer chemotherapy and pharmacology, (1986) vol. 17, No. 1, pp. 47-52.*
Freshney, Culture of Animal Cells, A Manual of Basic Technique, Alan R. Liss, Inc., 1983, New York, p4.*
Dermer, Another anniversary for the war on cancer, Bio/Technology, 1994, 12:320.*
Gura, Systems for identifying New Drugs are often faulty, Science, v278, 1997, pp. 1041-1042.*
Diaz et al, Cytotoxic flavone analogues of vitexicarpin, a constituent of the leaves of Vitex negundo, Journal of natural products, (Jun. 2003) vol. 66, No. 6, pp. 865-867.*
Mamber et al, Biological effects of acetomycin. I. Activity against tumor cells in vitro and in vivo, Journal of Antibiotics, (1987) vol. 40, No. 1, pp. 73-76.*
B.A. Magnuson, C. Zhao, G. Lala, Y. Kwon, T. Yu, J. Friedman, C. Obele, and M. Malik. 2003. Anthocyanin-rich extracts inhibit growth of human colon cancer cells and azoxymethane-induced colon aberrant crypts in rats. *Proceedings* of the Frontiers in Cancer Prevention Research Conference. B182. Oct. 26-30, Phoenix, AZ. Poster.
C. Zhao, M. Malik, B.A. Magnuson, M.P. Moyer, M.M. Giusti. 2003. The inhibitory effect of different anthocyanin-rich extracts on cancer cell growth. *Institute of Food Technologists Annual Meeting*. July, Chicago, Il. Poster.

(Continued)

*Primary Examiner* — Qiuwen Mi
(74) *Attorney, Agent, or Firm* — Darlene A. Vanstone; Carolyn S. Elmore; Elmore Patent Law Group P.C.

(57) ABSTRACT

The present invention provides compositions and methods for inhibiting the growth and cell cycle progression in carcinoma cells comprising the step of contacting the cells with an anthocyanin rich extract (ARE) in an amount effective to inhibit the growth and cell cycle progression of the carcinoma cells without effecting the growth and cell cycle progression on normal cells. The invention further provides therapeutic compositions and methods of inhibiting the growth and cell cycle progression of carcinoma cells in a patient comprising administering to a patient a therapeutically effective amount of an anthocyanin-rich extract with the proviso that the anthocyanin rich extract does not effect the growth and cell cycle progression of normal cells in the patient. In preferred embodiments, the anthocyanin-rich extract useful in the compositions and methods of the invention are derived from chokeberry, bilberry, grape or combinations thereof. In preferred embodiments the carcinoma cells are colon carcinoma cells.

1 Claim, 22 Drawing Sheets

OTHER PUBLICATIONS

C. Zhao, T. Yu, M. Malik, L.W. Douglass, B.A. Magnuson. 2003 Growth inhibition of HT-29 colon cancer cells by various berry extracts. *The American Association for Cancer Research 94th Annual Meeting*, Jul. 11-14, Washington DC. Poster.

M. Malik, L. Zhao, N. W. Schoene, M.M. Giusti, M.P. Moyer, B.A. Magnuson. 2002. Inhibition of colon cancer cell growth by anthocyanin-rich extracts from fruits. *Colon Cancer: Genes to Prevention*. Philadelphia, PA. Mar. 7-10. Poster.

B. Magnuson. 2002. Evidence of cancer inhibition by anthocyanin-rich extracts. International Workshop on Anthocyanins. Adelaide, Australia, Apr. 17-19. Slide Presentation.

Malik, Minnie, "Anthocyanin-Rich Extract From *Aronia meloncarpa* E. Induces a Cell Cycle Block in Colon Cancer but Not Normal Colonic Cells," *Nutrition and Cancer*, 46(2): 186-196 (2003).

M.Malik, C.Zhao, T.Wang, B.A.Magnuson. 2003. Cyanidin-3 galactoside, a major anthocyanin present in fruit extract of *Aronia melanocarpa*, affect growth and gene expression in colon cancer cells. The American Association for Cancer Research 94th Annual Meeting, Jul. 11-14, Washington DC. Poster.

Internet website-http://www.aronia.dk/information/anthocyanins.htm (5 pages).

Hollman, Peter. C.H., and Katan, Martijn B., Absorption, metabolism and health effects of dietary flavonoids in man. Biomedicine and Pharmacotherapy, 51(8): 305-310 (1997).

Hollman, P.C.H., and Katan, Martijn B., "Bioavailabilty and Health Effects of Dietary Flavonols," *Free Radical Research*, 31:237-248 (1999).

Rice-Evans, C.A., and Miller, N.J., "Antioxidant activities of flavonoids as bioactive components of food," *Biochemical Society Transactions*,24(3): 790-795 (1996).

Caderni Giovanna, et al., "Effects of black tea, green tea and wine extracts on intestinal carcinogenesis induced by azoxymethane in F344 rats," *Carcinogenesis*, 21(11): 1965-1969 (2000).

Caderni, Giovanna, et al., "Effect of complex polyphenols on colon carcinogenesis," *Eur. J Nutr.*, 38(3): 126-132 (1999).

Heiser, M.A., et al., "Influence of fruit and vegetable juices on the endogenous formation of N-nitrosoproline and N-nitrosothiazolidine-4-carboxylic acid in humans on controlled diets," *Carcinogenesis*, 13: 2277-2280 (1992).

Stoner, G.D., et al., "Isothiocyanates and Freeze-Dried Strawberries as Inhibitors of Esophageal Cancer," *Toxicological Sciences*, 52(Supplement): 95-100 (1999).

Kresty, L.A., et al., "Chemoprevention of Esophageal Tumorigenesis by Dietary Administration of Lyophilized Black Raspberries[1]," Cancer Res., 61: 6112-6119 (2001).

Xue, H., et al., "Inhibition of cellular transformation by berry extracts," *Carcinogenesis*, 22(2): 351-356 (2001).

Kamei, H., M.D. et al., "Suppression of Tumor Cell Growth by Anthocyanins In Vitro," *Cancer Invest*, 13(6): 590-594 (1995).

Koide, T., et al., "Antitumor Effect of Hydrolyzed Anthocyanin from Grape Rinds and Red Rice," *Cancer Biotherapy & Radiopharm.*, 11(4): 273-277 (1996).

Koide, T., et al., "Antitumor Effect of Anthocyanin Fractions Extracted from Red Soybeans and Red Beans in vitro and in vivo," *Cancer Biotherapy & Radiopharm.*, 12(4): 277-280 (1997).

Yoshimoto, Makoto, et al., "Antimutagenecity of Deacylated Anthocyanins in Purple-fleshed Sweetpotato," *Biosci. Biotechnol. Biochem.*, 65(7): 1652-1655 (2001).

Seeram N. P., et al., "Cyclooxygenase Inhibitory and Antioxidant Cyanidin Glycosides in Cherries and Berries," *Phytomedicine* 8(5): 362-369 (2001).

Harris, G.K., et al., "Effects of Lyophilized Black Raspberries on Azoxymethane-Induced Colon Cancer and 8-Hydroxy-2'-Deoxyguanosine Levels in the Fischer 344 Rat," *Nutr. Cancer*, 40(2):125-133 (2001).

Pool-Zobel, B.L., et al., "Anthocyanins are Potent Antioxidants in Model Systems but do not Reduce Endogenous Oxidative DNA Damage in Human Colon Cells," *Eur. J. Nutr.*, 38(5): 227-234 (1999).

Magnuson, B.A., et al., "Effects of Various Phytochemicals on Colonic Cancer Biomarkers," *American Chemical Society*, Chapter 22: 231-243 (1998).

Kenny, F.S., et al., "Gamma Linolenic Acid With Tamoxifen as Primary Therapy in Breast Cancer," 2000, *Int J Cancer*, 85:643-648.

Menendez, J.A., et al., "Synergistic Interaction Between Vinorelbine and Gamma-Linolenic Acid in Breast Cancer Cells," 2002, *Breast Cancer Res Treat*, 72:203-219.

Conklin, Kenneth A., "Dietary Antioxidants During Cancer Chemotherapy: Impact on Chemotherapeutic Effectiveness and Development of Side Effects," 2000, *Nutr Canc.*, 37:1-18.

Chinery, Rebecca, et al., "Antioxidants Enhance the Cytotoxicity of Chemotherapeutic Agents in Colorectal Cancer: A p53-Independent Induction of p21 $^{WAF1/CIP1}$ via C/EBPβ," *Nature Med.*, 3(11): 1233-1241 (1997).

Hour, Tzyh-Chyuan, et al., "Curcumin Enhances Cytotoxicity of Chemotherapeutic Agents in Prostate Cancer Cells by Inducing p21$^{WAF1/CIP1}$ and C/EBPβ Expressions and Suppressing NF-κB Activation," 2002, *Prostate*, 51:211-218.

Yin, Mei-Chin, et al., "Nonenzymatic Antioxidant Activity of Four Organosulfur Compounds Derived from Garlic," *J. Agric. Food Chem.*, 50: 6143-6147 (2002).

Ho, S.E., et al., "S-Allyl Cysteine Reduces Oxidant Load in Cells Involved in the Atherogenic Process," 2001, *Phytomedicine*, 8(1):39-46.

Liu, Ming, et al., "Antioxidant and Antiproliferative Activities of Raspberries," *J. Agric. Food Chem.*, 50: 2926-2930 (2002).

Huang, Chuanshu, et al., "Inhibition of Benzo(a)pyrene Diol-Epoxide-induced Transactivation of Activated Protein I and Nuclear Factor κB by Black Rasberry Extracts," *Cancer Res.*, 62(23): 6857-6863 (2002).

Tucker, Jody M., et al., "Response to 5-Fluorouracil Chemotherapy is Modified by Dietary Folic Acid Deficiency in Apc$^{Min/+}$Mice," Cancer Letters, 187:153-162 (2002).

Magnuson, B.A., et al, "Resistance of Aberrant Crypt Foci to Apoptosis Induced by Azoxymethane in Rats Chronically Fed Cholic Acid," *Carcinogenesis*, 15(7):1459-1462 (1994).

Zhao, Cuiwei, et al., "Effects of Commercial Anthocyanin-Rich Extracts on Colonic Cancer and Nontumorigenic Colonic Cell Growth," *J Agric. Food Chem.*, 52: 6122-6128 (2004).

Decision on Appeal for U.S. Appl. No. 11/106,240, dated Mar. 9, 2011 and all papers filed in connection therewith.

* cited by examiner

Figure 9. Anthocyanin profile of three different commercial color extracts, run under identical HPLC conditions Figure 10. Cell growth over time of HT-29 and NCM cell lines exposed to anthocyanin rich extracts. Controls: no treatment and vehicle only. B25, B50, B75: bilberry at 25 ug/mL, 50 ug/mL and 75 ug/mL respectively.

C= Control, B=Bilberry, CH=Chokeberry, G=Grape

C= Control, B=Bilberry, CH=Chokeberry, G=Grape

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
ggaacttcga ctttgtcacc gag                                              23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gaacctctca ttcaaccgcc tag                                              23

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tgcctctaaa agcgttggat                                                  20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tttttgcccc aaactacctg                                                  20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ggccaaaatg cctatgaaga                                                  20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aaacatggca gtgacaccaa                                                  20

<210> SEQ ID NO 7
<211> LENGTH: 22
<212> TYPE: DNA

-continued

```
<213> ORGANISM: Artificial Sequence
<220> FEATURE:
<223> OTHER INFORMATION: Primer

<400> SEQUENCE: 7
cagccattag tttacctgga cc                                            22

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
tgttggagca gctaagtcaa aa                                            22
```

ANTHOCYANIN-RICH COMPOSITIONS AND METHODS FOR INHIBITING CANCER CELL GROWTH

RELATED APPLICATIONS

This application is a continuation of U.S. application Ser. No. 10/795,967, filed Mar. 8, 2004, (now abandoned) which claims the benefit of U.S. Provisional Application No. 60/452,600, filed on Mar. 6, 2003. The entire teachings of the above application(s) are incorporated herein by reference.

FIELD OF THE INVENTION

This invention relates to food extracts rich in anthocyanins as specific inhibitors of cancer cell growth.

BACKGROUND OF THE INVENTION

Colorectal cancer (CRC) is the second leading cause of cancer death in Western countries (American Cancer Society 2000). It is estimated that in the United States approximately 57,000 people will die from colorectal cancer in 2003 (Cancer Facts and Figures 2003, American Cancer Society, 2003). In recent years epidemiological studies have shown that consumption of a diet containing fruits and vegetables rich in antioxidants is linked to lower incidence of colon cancer (Yang et al., 2001, *Annu Rev Nutr.*, 21:381-406). Many of the compounds in fruits and vegetables such as vitamins, minerals, phytochemicals are defined as dietary supplements (Dietary Supplement Health and Education Act, 1994). Among colorectal cancer patients it is reported that 64% use alternative medicine of which 57% take some kind of dietary supplement (Patterson et al., 2002, *J. Altern Complement Med*, 8:477-485). Various phytochemicals in fruits and vegetables have been shown to inhibit colon cancer development in animal model studies.

There remains a need for identifying natural compounds, phytochemicals and food extracts that are effective as chemopreventatives against cancer, including colon cancer. The present inventors have discovered that compositions comprising anthocyanin-rich extracts are effective for inhibiting cancer cell growth, and have further discovered methods for specifically inhibiting the growth of colon cancer cells without inhibiting the growth of normal colonic cells.

SUMMARY OF THE INVENTION

The present invention provides compositions and methods for inhibiting the growth and cell cycle progression in carcinoma cells comprising the step of contacting the cells with an anthocyanin rich extract (ARE) in an amount effective to inhibit the growth and cell cycle progression of the carcinoma cells without effecting the growth and cell cycle progression on normal cells. The invention further provides therapeutic compositions and methods of inhibiting the growth and cell cycle progression of carcinoma cells in a patient comprising administering to a patient a therapeutically effective amount of an anthocyanin-rich extract with the proviso that the anthocyanin rich extract does not effect the growth and cell cycle progression of normal cells in the patient. In preferred embodiments, the anthocyanin-rich extract useful in the compositions and methods of the invention are derived from chokeberries (*Aronia meloncarpa* E.), bilberries (*Vaccinium myrtillus* L.), grapes (*Vitis vinifera*) or combinations thereof. In preferred embodiments the carcinoma cells are colon carcinoma cells.

BRIEF DESCRIPTION OF THE DRAWINGS

FIG. 3A are a series of histograms showing cell cycle distribution of control (vehicle) and ARE-treated (50 µg/ml) HT-29 cells after 24, 48 and 72 h of exposure and FIG. 3B is a bar graph showing the percent cells in each cell cycle phase after 24, 48 and 72 h of exposure to vehicle (con) or chokeberry ARE (ARE) media.

FIG. 4A is an electropherogram (solid line) of control experiment; FIG. 4B is an electropherogram (dashed line) of ARE treated experiment; and FIG. 4C shows the superimposition of electropherograms of treated experiment over control experiment.

FIG. 7A is a Gel-like image from Agilent bioanalyzer 2100 of semiquantitative RT-PCR amplification of cyclooxygenase genes in NCM460 (A) and HT-29 (B) demonstrates a higher expression of COX-1 gene (401 bp) in NCM460 normal colon epithelial cells (A1) as compared to the expression in HT-29 cells (B1). COX-2 gene (297 bp) expression in NCM460 (A2) was lower compared to COX-2 expression in HT-29 colon cancer cells (B2); and FIG. 7B is a bar chart that depicts the differences in COX-1 and COX-2 gene expression in normal and cancer colon cell lines.

FIG. 8A shows the percent change in expression of COX-2 gene induced by ARE exposure in HT-29 cells; FIG. 8B shows the quantitative EIA determination of COX-2 protein in HT-29 cell lysates; and FIG. 8C is a bar graph showing the media from COX-2 protein experiment was analyzed for $PGE_2$ production.

FIG. 14A is purified chokeberry anthocyanin fraction.

FIG. 14B is a purified fraction of aglycon chokeberry ARE.
FIG. 14C is purified bilberry anthocyanin fraction.

DETAILED DESCRIPTION OF THE INVENTION

Figure 1:
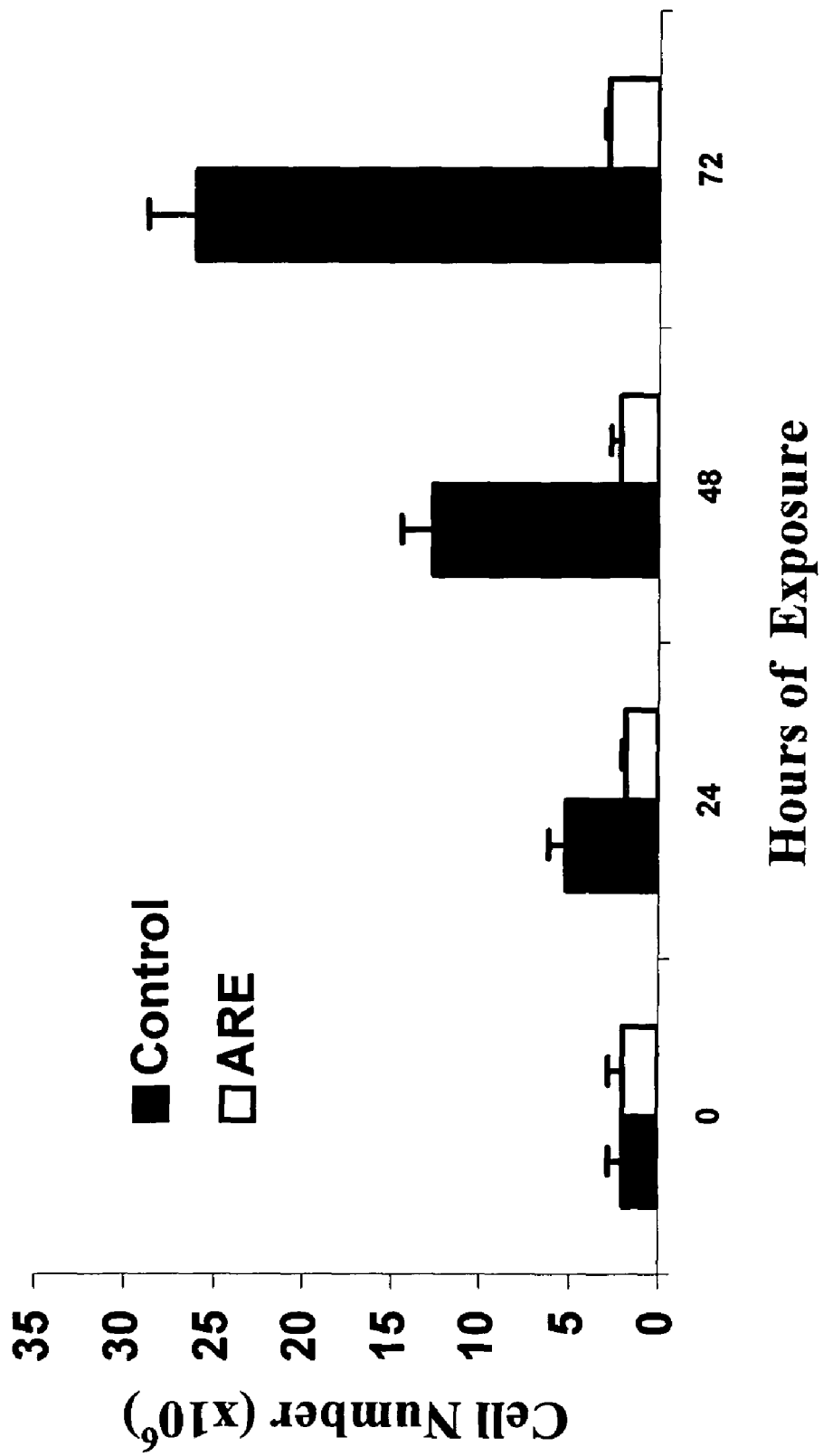
FIG. 1 is a bar graph showing the effect of chokeberry ARE on growth of colon cancer HT-29 cells over time.

The present invention provides compositions and methods for inhibiting the growth and cell cycle progression in carcinoma cells comprising the step of contacting the cells with an anthocyanin rich extract (ARE) in an amount effective to inhibit the growth and cell cycle progression of the carcinoma cells without effecting the growth and cell cycle progression on normal cells. The invention further provides therapeutic compositions and methods of inhibiting the growth and cell cycle progression of carcinoma cells in a patient comprising administering to a patient a therapeutically effective amount of an anthocyanin-rich extract that inhibits the growth and cell cycle progression of carcinoma cells without effecting the growth and cell cycle progression of normal cells in the patient. In preferred embodiments, the anthocyanin-rich extract useful in the compositions and methods of the invention is derived from chokeberries (*Aronia meloncarpa* E.), bilberries (*Vaccinium myrtillus* L.), grapes (*Vitis vinifera*) or combinations thereof. In one preferred embodiment the ARE is derived from chokeberries. In other preferred embodiments the carcinoma cells are colon carcinoma cells.

Anthocyanins are flavonoid pigments in blue and red fruits and vegetables. Bioflavonoids are the isoflavonoid and flavonoid compounds contained in certain foods such as berries. Phenolics are compounds with a phenyl group and having one or more hydroxyl groups contained in certain foods such as berries. Fruits and vegetables contain three main classes of dietary phenolics; flavonoids, phenolic acids and polyphenols. Over 5,000 different flavonoids have been described, and they are categorized into flavonols, flavones, catechins, flavanones, anthocyanidins and isoflavonoids. In recent years a large number of investigators have studied how polyphenols and proanthocyanidins may act as anticancer agents by protection against free radical damage. The different hydroxylation, glycosylation and acylation patterns may modulate their antioxidative and biological. Acylated anthocyanins have been reported to have increased antioxidant activity as compared to their non acylated counterparts and studies suggest that antioxidant compounds may be effective against various cancers. The inventors have obtained data suggesting that anthocyanin-rich extracts may be potent inhibitors of cell proliferation by blocking the cell cycle in colon cancer cells (see Example 1).

"Anthocyanin-rich extracts" or "AREs" are extracts derived from foods such as fruits and vegetables that are preferably, semi-purified, purified and/or concentrated such that the water content, sugar content and acid content are reduced and the remaining components are mainly the phenolics including anthocyanins. AREs are known in the art and many are readily available commercially from sources such as Artemis International, Inc. (Madera, Calif.). Concentrated and highly concentrated (about at least 2-3 grams of monomeric anthocyanin per liter or per kg) AREs obtained using standard separation and purification techniques and are also readily commercially available in the form of powders and liquids. Methods for obtaining AREs and isolated and concentrated anthocyanins are well known in the art (see, the Examples infra).

Fruits and vegetable that are particularly suitable for providing anthocyanin rich extracts include those fruits and vegetables preferably containing approximately at least 10 mg per 100 g of fresh fruit. In preferred methods and compositions of the invention, the AREs are derived and concentrated from berries and vegetables including but not limited to chokeberry, black raspberry, red raspberry, blueberry, blackberry, cranberry, bilberry, black currant, cherry, elderberry, grape, kiwi, strawberry, purple potatoes and black carrots or combinations of any of the above. Alternatively, blueberries and cherries extracts are not used. In one preferred embodiment, the ARE is derived from chokeberry, bilberry or grape or combinations thereof. In another preferred embodiment, the ARE is derived from chokeberry and the major anthocyanin contained in extract of chokeberry is cyanidin-3-galactoside.

In accordance with the invention, carcinoma cells include abnormal cancer cells associated with colorectal cancer, ovarian cancer, bone cancer, renal cancer, breast cancer, gastric cancer, pancreatic cancer, melanoma, hematopoietic tumors such as lymphoma, leukemia, plasma cell dyscrasias, and multiple myeloma and amylodosis. Preferably, the growth and cell cycle progression of colon carcinoma cells are inhibited by the methods and compositions of the invention.

In one preferred embodiment, the invention provides a method for inhibiting the growth and cell cycle progression of carcinoma cells, comprising contacting the carcinoma cells with an anthocyanin-rich extract in an amount effect to down regulate Cox 2 gene expression in carcinoma cells without effecting Cox 1 or Cox 2 gene expression in normal cells. In preferred embodiments anthocyanin-rich extract is derived from bilberries, grapes or combinations thereof. In other preferred embodiments, the carcinoma cells are colon carcinoma cells.

In another preferred embodiment, the invention provides a method for inhibiting the growth and cell cycle progression of carcinoma cells, comprising contacting the carcinoma cells with an anthocyanin-rich extract in an amount effective to up regulate the gene expression of $p21^{WAF1}$ and $p27^{KIP1}$ in carcinoma cells without effecting $p21^{WAF1}$ and $p27^{KIP1}$ gene expression in normal cells. In one preferred embodiment, the carcinoma cells are colon carcinoma cells. In another preferred embodiment, the anthocyanin-rich extract is derived from chokeberries, bilberries or grapes or combinations thereof. In yet another preferred embodiment, the anthocyanin-rich extract is derived from chokeberries.

In another preferred embodiment, the invention provides a method of inhibiting the growth and cell cycle progression of carcinoma cells comprising contacting the carcinoma cells with an anthocyanin-rich extract in an amount effective to cause dual blockage of cell cycle progression at both the $G_1/G_0$ and $G_2/M$ phases of the cell cycle without effecting the cell cycle progression in normal cells. In one preferred embodiment, the carcinoma cells are colon carcinoma cells. In another preferred embodiment, the anthocyanin-rich extract is derived from chokeberries, bilberries or grapes or combinations thereof. In yet another preferred embodiment, the anthocyanin-rich extract is derived from chokeberries.

In yet another preferred embodiment, the invention provides a method of inhibiting the growth and cell cycle progression of carcinoma cells comprising contacting the carcinoma cells with an anthocyanin-rich extract in an amount effective to down regulate the gene expression of cyclin A and cyclin B1 without effecting the gene expression of cyclin A and cyclin B1 in normal cells. In one preferred embodiment, the carcinoma cells are colon carcinoma cells. In another preferred embodiment, the anthocyanin-rich extract is derived from chokeberries, bilberries or grapes or combinations thereof. In yet another preferred embodiment, the anthocyanin-rich extract is derived from chokeberries.

In another preferred embodiment, the invention provides a method of inhibiting the growth and cell cycle progression of carcinoma cells comprising contacting the carcinoma cells with an anthocyanin-rich extract in an amount effective to up regulate the gene expression of $p21^{WAF1}$ and $p27^{KIP1}$ and down regulate gene expression of cyclin A and cyclin B1 in carcinoma cells, without effecting the gene expression of $p21^{WAF1}$, $p27^{KIP1}$, cyclin A and cyclin B1 in normal cells. In one preferred embodiment, the carcinoma cells are colon carcinoma cells. In another preferred embodiment, the anthocyanin-rich extract is derived from chokeberries, bilberries or grapes or combinations thereof. In yet another preferred embodiment, the anthocyanin-rich extract is derived from chokeberries.

The terms "cell cycle" and "cell cycle progression" are well known in the art (see for example *Molecular Biology of the Cell*, Bruce Alberts et al., $4^{th}$ ed. (2002) Garland Science New York, N.Y.) and essentially refer to the phases involved in cellular reproduction. Briefly, the two major cell cycle phases include the S phase for DNA duplication and the M phase for mitosis. There are gap phases that function to extend the time for carrying out the S or M phase. The $G_1$ gap phase occurs between M phase and the S phase and the $G_2$ phase occurs between the S phase and the M phase of the cell cycle. In certain circumstances, cells may delay their progress through the $G_1$ phase and enter a resting phase called $G_0$. Cell growth and cell cycle progression may be inhibited, arrested or blocked at any one or more points in the cell cycle growth and progression by any number of internal and external influences on the cell. The present invention focuses on the effects that the AREs of the invention have on the growth and progression of the cell cycle and particularly inhibition of cell growth and cell cycle progression.

A patient, including mammals, and specifically humans, suffering from colorectal cancer, ovarian cancer, bone cancer, renal cancer, breast cancer, gastric cancer, pancreatic cancer, melanoma, hematopoietic tumors such as lymphoma, leukemia, plasma cell dyscrasias, and multiple myeloma and amylodosis cancer can be treated by the topical or systemic administration to the patient of an effective amount of an ARE in accordance with the invention, preferably in the presence of a pharmaceutically acceptable carrier or diluent.

Thus, the invention provides a method of inhibiting the growth and cell cycle progression of carcinoma cells in a patient comprising administering to a patient a therapeutically effective amount of an anthocyanin-rich extract effective to inhibit the growth and cell cycle progression of carcinoma cells without effecting the growth and cell cycle progression of normal cells in the patient. In one embodiment the carcinoma cells are colon carcinoma cells. In another embodiment, the anthocyanin-rich extract is derived from chokeberries, bilberries, grapes or combinations thereof.

In another preferred embodiment, the invention provides a method of inhibiting the growth and cell cycle progression of colon carcinoma cells in a patient comprising administering to a patient a therapeutically effective amount of an anthocyanin-rich extract derived from chokeberries capable of causing dual blockage of cell cycle progression at both the $G_1/G_0$ and $G_2/M$ phases of the cell cycle without effecting the cell cycle progression in normal cells.

The invention further provides a pharmaceutical composition preferably comprising a pharmaceutically acceptable carrier and an anthocyanin-rich extract (ARE) capable of inhibiting the growth and cell cycle progression of carcinoma cells in a patient without effecting the growth and cell cycle progression of normal cells in the patient. The pharmaceutical composition preferably comprises an anthocyanin-rich extract derived from chokeberries, bilberries, grapes or combinations thereof. In a preferred embodiment, the pharmaceutical composition comprises an ARE derived from chokeberries.

In yet another embodiment the invention provides a pharmaceutical composition comprising a pharmaceutically acceptable carrier and an anthocyanin-rich extract capable of causing dual blockage of cell cycle progression at both the $G_1/G_0$ and $G_2/M$ phases of the cell cycle in a patient without effecting the cell cycle progression in normal cells in the patient. The pharmaceutical composition preferably comprises an anthocyanin-rich extract derived from chokeberries, bilberries, grapes or combinations thereof. In a preferred embodiment, the pharmaceutical composition comprises an ARE derived from chokeberries.

In one embodiment, anthocyanin-rich extracts of the invention can be formulated for administration as a food supplement using one or more fillers. Neutraceuticals compositions can be formulated for administration by any route including, but not limited to, inhalation, insufflation (through mouth or nose) oral, buccal, parenteral, vaginal or rectal administration. In one embodiment for oral administration, the pharmaceutical compositions are added directly to foods ingested as part of a normal meal. Various methods are known to those skilled in the art for addition or incorporation of nutraceuticals into foods. Alternatively, AREs in accordance with the invention can be administered as conventional pharmaceuticals as is described below.

The pharmaceutical compositions in accordance with the invention can be administered subcutaneously, intravenously, intraperitoneally, intramuscularly, parenterally, orally, submucosally, by inhalation, transdermally via a slow release patch, or topically, in an effective dosage range to treat the target condition. Typical systemic dosages for all of the herein described conditions are those ranging from 0.01 mg ARE/kg to 500 mg ARE/kg of body weight per day as a single daily dose or divided daily doses. Typical daily dosages can range from 0.1 mg-300 mg, preferably 1-200 mg, and more preferably between 60-100 mg. Typical dosages for topical application are those ranging from 0.001 to 100% by weight of the ARE. The pharmaceutical composition is administered for a sufficient time period to alleviate the undesired symptoms and the clinical signs associated with the condition being treated.

The concentration of ARE in the pharmaceutical composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The pharmaceutical composition may be administered all at once, or may be divided into a number of smaller doses to be administered at varying intervals of time.

A preferred mode of administration of the pharmaceutical composition for systemic delivery is oral. Oral compositions will generally include an inert diluent or an edible carrier. They may be enclosed in gelatin capsules or compressed into tablets. For the purpose of oral therapeutic administration, the active compound, can be incorporated with excipients and used in the form of tablets, troches or capsules. Pharmaceutically compatible binding agents, and/or adjuvant materials can be included as part of the composition.

The tablets, pills, capsules, troches and the like can contain, any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The pharmaceutical compositions of the invention can be administered as a component of an elixir, suspension, syrup, wafer, lozenge, chewing gum or the like. A syrup may contain sucrose as a sweetening agent and certain preservatives, dyes and colorings and flavors.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If the pharmaceutical compositions of the invention are administered intravenously, preferred carriers are physiological saline, bacteriostatic water, Cremophor EL™ (BASF, Parsippany, N.J.) or phosphate buffered saline (PBS). In a preferred embodiment, the pharmaceutical compositions are prepared with carriers that will protect the compound against rapid elimination from the body, such as a controlled release formulation, including implants and microencapsulated delivery systems.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

EXAMPLES

Example 1

Studies Showing that AREs Induce a Cell Cycle Block in Colon Cancer but not Normal Colonic Cells Introduction-Anthocyanin-rich extracts, potent antioxidants and commercially available food coloring agents, have been reported to inhibit growth of various cancer cell lines. We investigated the effect of semi-purified anthocyanin-rich extract from fruits of *Aronia meloncarpa*, on normal colon and colon cancer cell lines. A 24 h exposure to 50 m monomeric anthocyanin/ml of *Aronia* extract resulted in 60% growth inhibition of human HT-29 colon cancer cells. The treated cells showed a blockage at G1/G0 and G2/M phases of the cell cycle. The cell cycle arrest coincided with an increased expression of the $p21^{WAF1}$ and $p27^{KIP1}$ genes and decreased expression of Cyclin A and B genes. Prolonged exposure to the extract resulted in no further change in the cell number indicating a cytostatic inhibition of cell growth. NCM460 normal colon cells demonstrated <10% growth inhibition at the highest concentration of 50 µg/ml extract. A 35% decrease in the cyclooxygenase-2 gene expression was observed within 24 h of exposure of HT-29 cells but did not translate into decreased protein levels or protein activity.

Materials and Methods

Cell Culture—Human HT-29 colon cancer cells (ATCC, HTB 38) were grown in McCoy's 5A medium (BioWhitaker Inc., Walkersville, Md.), and normal colon epithelial cells, NCM460 (INCELL Corp. LLC, Austin, Tex.) were grown in 25% conditioned M3:10 medium (INCELL Corp., LLC). Media were supplemented with 10% fetal bovine serum (FBS) and 1× antibiotic-antimycotic (Invitrogen Corporation, Carlsbad, Calif.), and cells were maintained in a humidified atmosphere of 95% air/5% $CO_2$ at 37° C.

Anthocyanin-Rich Extract (ARE) The ARE from *Aronia meloncarpa* E. (chokeberry; Artemis International, Inc., Madera, Calif.) was semi-purified by solid-phase extraction using a C-18 cartridge (Waters Corp., Milford, Mass.). Briefly, 10 g of powdered extract was dissolved in 100 ml 0.01% HCl. The extract was loaded onto a C-18 cartridge that had been pre-treated with ethanol (100%), followed by acidified water (0.01% HCl). Anthocyanins and other phenolics that bind to the C-18 cartridge were recovered with ethanol containing 0.01% HCl. The alcohol was evaporated at 40° C., and the solutes re-dissolved in 10 ml 0.01% HCl-deionized water (vehicle). Monomeric anthocyanin content was determined by the pH-differential method (15).

Cell Proliferation—Freshly trypsinized cells were seeded in 25-$cm^2$ ($1×10^6$ cells) or 75-$cm^2$ ($2×10^6$ cells) flasks in duplicate. The cells were grown for 24 h under normal growth conditions prior to treatment with chokeberry ARE. Freshly prepared ARE was added in concentrations ranging from 10 to 200 µg monomeric anthocyanin/ml medium. A vehicle control contained acidified water and was added at the same volume as ARE added to treated cells. The addition of the small amount of acidified extract (pH 4.0) did not affect the pH of the media. Cells were also grown in media alone (no-vehicle control) to ensure there was no effect of the vehicle on the growth of the cells. Prior to exposure to ARE for 24 h, 48 h or 72 h treatments, the medium was replaced with fresh medium (10% FBS) containing either vehicle control (acidified water) or ARE. For each time point, the cells were trypsinized and centrifuged at 400 g for 10 min at room temperature. Aliquots of cells were counted using a hemacytometer and viability measured using Trypan blue dye exclusion.

Cell Cycle Analysis—Cell cycle analysis was performed using flow cytometry. HT-29 cells were seeded ($2×10^6$ cells/75-$cm^2$ flask) in duplicate and incubated for 24 h before exposure to 50 µg monomeric anthocyanin/ml for various time periods of 24 h, 48 h and 72 h. All experimental conditions were as described above for the cell proliferation study. To further analyze if the cells recovered from growth inhibition after initial 24 h exposure to ARE, cells were grown for an additional 24 h in fresh media that did not contain either ARE or acidified water. Approximately $1×10^6$ cells were fixed in cold 70% ethanol and analyzed for cell cycle distribution as described by Park and Schoene (16). Briefly, the fixed cells were centrifuged, washed with 1× phosphate buffered saline (PBS) and then stained for DNA content by resuspending in 1 ml staining solution (PBS containing 20 µg propidium iodide and 25 mg ribonuclease A) (16). Cells were stained for 30 min at room temperature and then immediately analyzed by flow cytometry. Data were collected for 10,000 cellular events per sample using a FACSCalibur cytometer and CELLQuest software (Becton Dickinson, San Jose, Calif.). Cell cycle distribution percentages of stained nuclei were calculated using Modfit LT software (Verity Software House, Inc., Topsham, Me.). The DNA QC Particle Kit, for verification of instrument performance, was purchased from Becton Dickinson.

Gene Expression Analysis—HT-29 and NCM460 cells ($2 \times 10^6$ cells/75-$cm^2$ flasks) were incubated for 24 h in the presence of 10-50 µg/ml media. After exposure to ARE for 24 h, 48 h and 72 h the cells were either directly lysed in the flasks or trypsinized and counted before total cellular RNA was extracted using TRIzol Reagent (Invitrogen, CA) according to the manufacturer's protocol. RNA samples were treated with DNAse-I enzyme using the DNA free kit (Ambion Inc., Austin, Tex.). RNA Nano LabChip® and the Agilent 2100 bioanalyzer (Agilent Technologies, Palo Alto, Calif.) were used to check the quality and the quantity of the isolated total RNA. First strand synthesis was done using Retroscript kit (Ambion Inc.) and cDNA was measured spectrophotometrically.

Changes in gene expression were determined using multiplex RT-PCR. Table 1 lists the genes of interest and primer sequences.

Ribosomal 18S (Ambion Inc.) was used as the internal control. The 18S primer:competimer ratio was optimized according to the manufacturer's instructions before changes in expression of these genes was studied. After optimization of PCR conditions for a multiplex reaction (cell cycle, primer conditions and annealing temperature) the following parameters were used for the assay: 1× complete reaction buffer; dNTPs mixture (200 µM each); 18S primers:competimers (1:9) mixture (0.4 µM), $p21^{WAF1}$ primer (0.4 µM) or $p27^{KIP1}$ primer (0.4 µM) or Cyclin A (0.2 µM) or Cyclin B1 (0.2 µM) and 0.4 U/10 µl Taq DNA polymerase. The amplification conditions used were: one 2-min cycle at 92° C. followed by 27 cycles of denaturation for 30 s at 92° C., annealing for 40 s at 60° C. and extension for 1 min at 72° C. A final extension was given for 5 min at 72° C. before analysis of the PCR products.

Changes in expression of cyclooxygenase genes were studied using human COX-1 and COX-2 gene-specific Relative RT-PCR Kits (Ambion Inc.). Ribosomal gene 18S (498 bp) was used as an internal control. PCR assay conditions were optimized before changes in expression of COX-1 gene (401 bp) and COX-2 gene (297 bp) was analyzed. The multiplex reaction contained 1× complete reaction buffer; dNTPs mixture (200 µM each); 18S primers:competimers (1:9) mixture (0.4 µM), 0.4 µM COX-1 primer or 0.4 µM COX-2 primer and 0.4 U/10 µl Taq DNA polymerase. The following thermocycling conditions were used for PCR assays: one 2-min cycle at 92° C. followed by 26 cycles of denaturation for 30 s at 92° C., annealing for 30 s at 59° C. (COX-1) or 30 s at 60° C. (COX-2), and extension for 1 min at 72° C. The final extension was given for 5 min at 72° C.

The PCR products from multiplex reactions were analyzed using DNA 500 or DNA 7500 LabChip® and Agilent 2100 bioanalyzer according to the manufacturer's protocol. The changes in the gene expression were represented by the changing ratio between the area of bands representing gene of interest and the band representing 18S gene. A ratio difference in the control versus the treated cells is the measure of change in gene expression.

COX-2 Protein Assay—HT-29 and NCM460 cells seeded in 25-$cm^2$ flasks ($1 \times 10^6$ cells) and exposed to 50 µg/ml ARE for 24 h, 48 h, and 72 h were trypsinized and counted. COX-2 protein was measured using TiterZyme® EIA (Assay Designs, Inc., Ann Arbor, Mich.) according to the manufacturer's instructions.

Prostaglandin-E2 Assay—The amounts of prostaglandin-E2 ($PGE_2$) in the culture medium were determined using EIA kit (Cayman Chemical, Ann Arbor, Mich.) following manufacturer's protocol. In short, the culture medium from each time frame was centrifuged at 800 g for 5 min and the supernatant stored at −80° C. The supernatant was added to 96-well plates, coated with an anti-mouse antibody, mixed with a PG/acetylcholinesterase tracer and a monoclonal antibody against prostaglandin and incubated at 4° C. overnight. Unbound PG/acetylcholinesterase was removed and washed extensively and bound acetylcholinesterase was detected by Ellman's reagent and measured at 405 nm.

Results

Chokeberry ARE Inhibits Growth of Human HT-29 Colon Cancer Cells—Growth of HT-29 cells exposed to 50 µg monomeric anthocyanin/ml was inhibited 60-70% within the first 24 h (FIG. 1). Although continuous exposure of HT-29 cells to ARE for up to 72 h resulted in ca. 90% inhibition of growth relative to the control cells (FIG. 1), the number of cells did not change with time, and >95% of the cells were viable, indicating a cytostatic inhibition.

Inhibition of HT-29 cell growth by chokeberry ARE was concentration dependent up to 50 n monomeric anthocyanin/ml of medium (data not shown). At higher concentrations of ARE, inhibition of growth reached a plateau and the cells were no longer viable, as analyzed by Trypan blue dye exclusion (data not shown). HT-29 cells incubated in the presence of acidified water (vehicle control) grew at the same rate as cells incubated in media alone (no-vehicle control) indicating

TABLE 1

Primer sequences (5'-3') and expected product size

| Gene Name | Sequence of Primers | Product Size | SEQ ID NO |
|---|---|---|---|
| $p21^{WAF1}$ | forward: 5'-GGAACTTCGACTTTGTCACCGAG-3' | 561 bp | SEQ ID 1 |
| | reverse: 5'-GAACCTCTCATTCAACCGCCTAG-3' | | SEQ ID 2 |
| $p27^{KIP1}$ | forward: 5'-TGCCTCTAAAAGCGTTGGAT-3' | 542 bp | SEQ ID 3 |
| | reverse: 5'-TTTTTGCCCCAAACTACCTG -3' | | SEQ ID 4 |
| Cyclin B1 | forward: 5'-GGCCAAAATGCCTATGAAGA-3' | 589 bp | SEQ ID 5 |
| | reverse: 5'-AAACATGGCAGTGACACCAA -3' | | SEQ ID 6 |
| Cyclin A | forward: 5'-CAGCCATTAGTTTACCTGGACC-3' | 542 bp | SEQ ID 7 |
| | reverse: 5'-TGTTGGAGCAGCTAAGTCAAAA -3' | | SEQ ID 8 | that acidified water used in preparation of ARE did not affect the growth of cells (data not shown).

Figure 2:
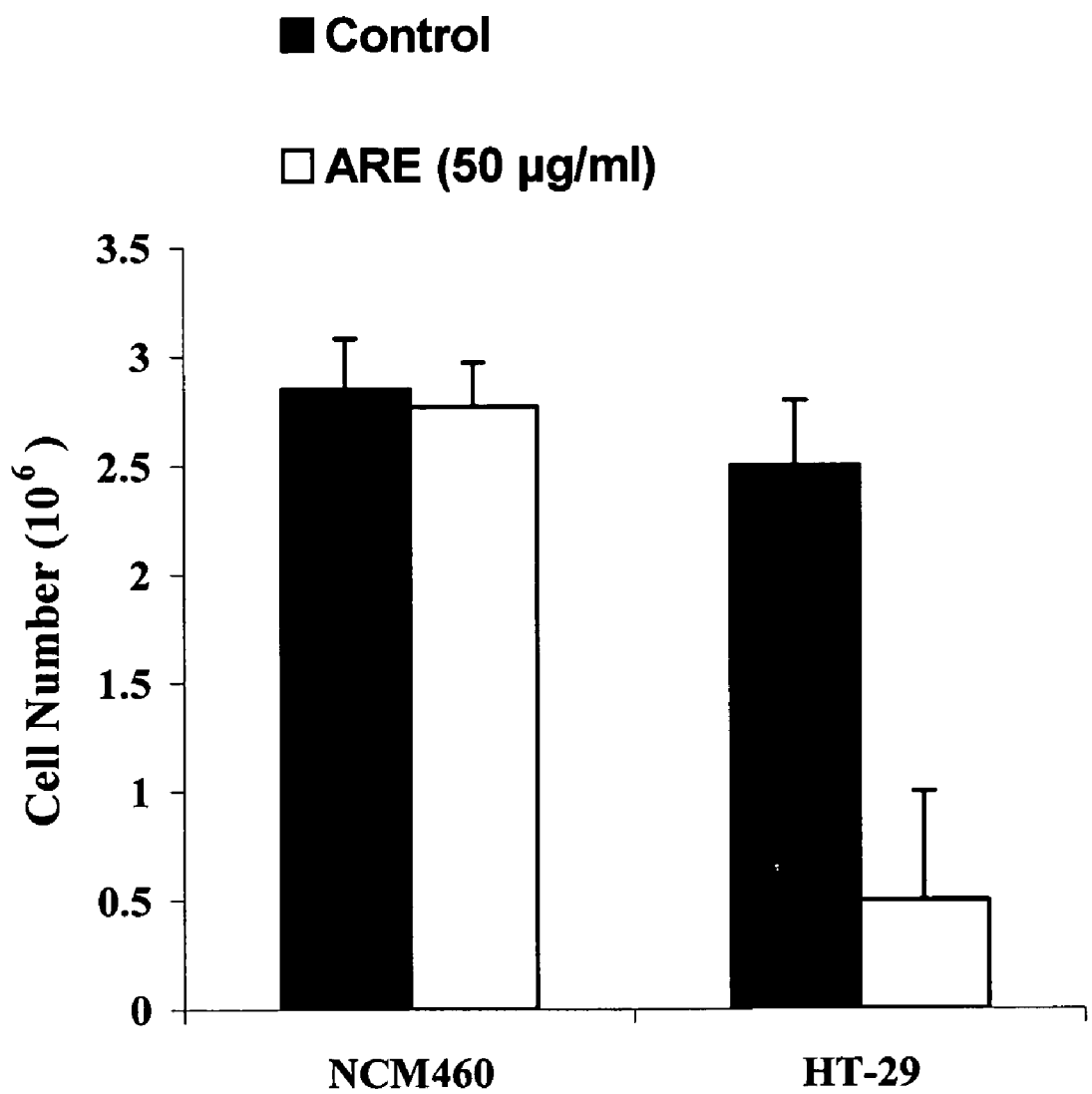
FIG. 2 is a bar graph comparing the effect of chokeberry ARE on growth of colon cancer HT29 cells with normal colon NCM460 cells.

Chokeberry ARE does not Inhibit Growth of Human NCM460 Normal Colon Cells—To assess whether ARE inhibits normal cell growth, we exposed NCM460 derived from normal colon epithelial cells (17), to the same concentrations of chokeberry ARE. This study shows for the first time that, growth of normal human NCM460 colon cells was inhibited less than 10% by exposure to 50 µg/ml of media for 24 h in contrast with HT-29 colon cancer cells where growth inhibition of 65% was observed (FIG. 2).

Figure 3A:
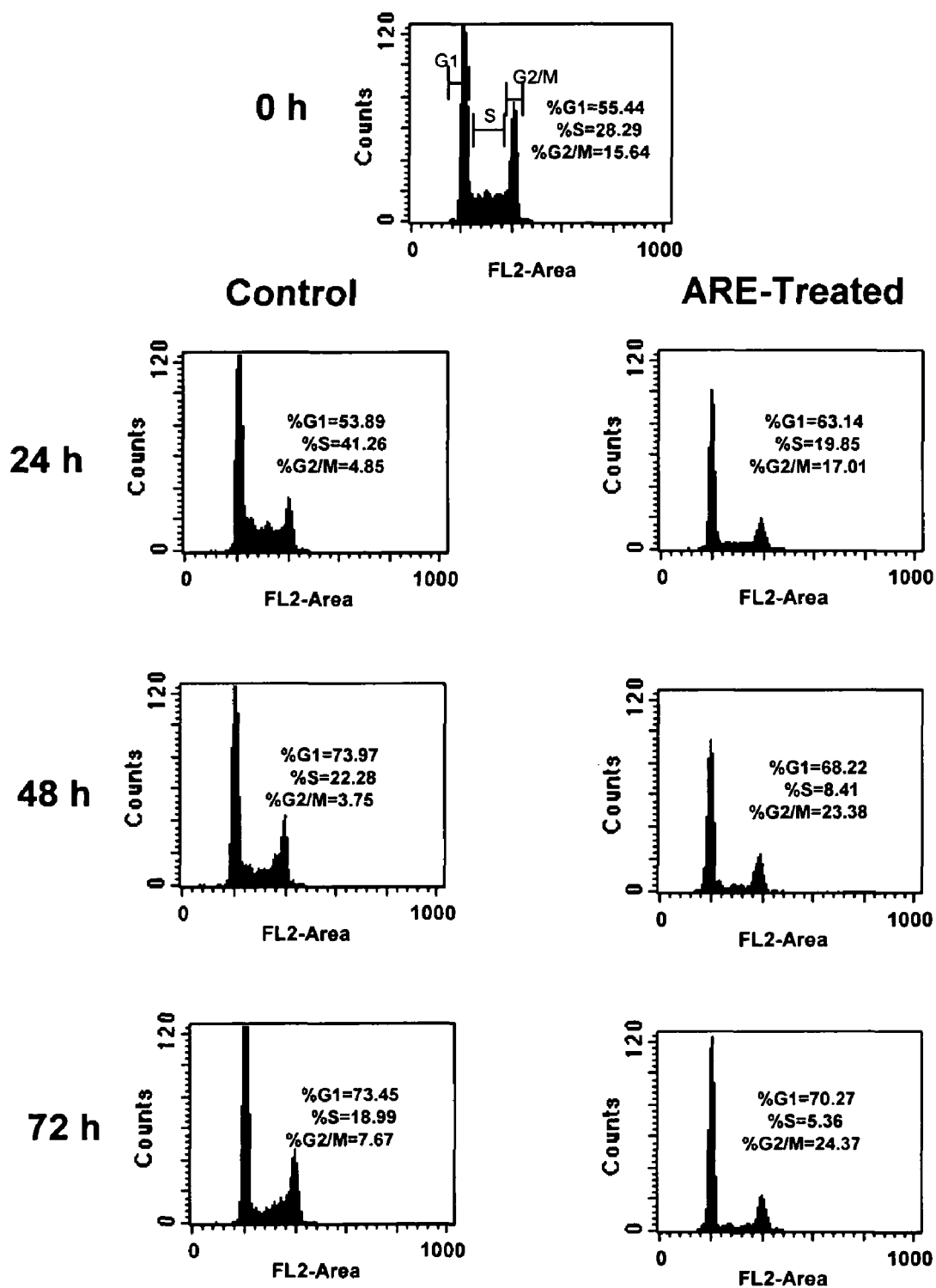
FIGS. 3A-B shows the effect of ARE on cell cycle progression of HT-29 cells.
Figure 3B:
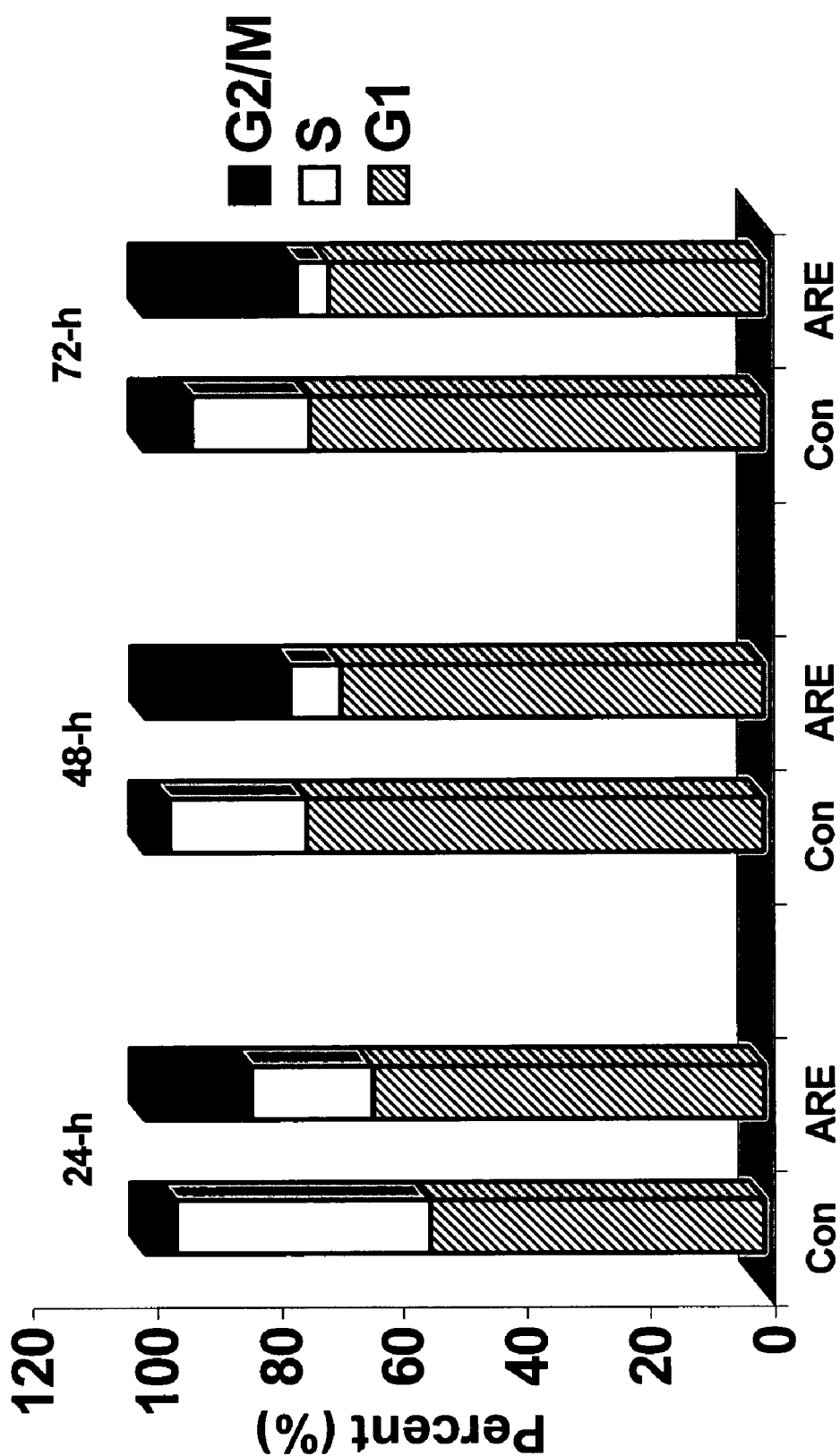

Chokeberry ARE induces a Dual Block in Cell Cycle of HT-29 Cells—We investigated whether ARE-induced inhibition of cell growth is through a blockage in progression of cells through the cell cycle. In the present study, chokeberry ARE arrested the HT-29 cells at G1/G0 phase of the cell cycle with an accompanied concomitant decrease of percentage of cells in S phase and an increase in the G2/M phase (FIG. 3A). As shown in FIG. 3B, within 24 h of exposure the percentage of cells in G1/G0 phase increased from 54% to 63%, the percentage of cells in S phase decreased from 41% to 20%, and in G2/M phase the cell percentage increased from 5% to 17%. The increase in percentage of cells in the G2/M phase was more apparent with continued exposure to ARE for up to 48 h and 72 h (FIG. 3B). Compared with the controls at 48 h and 72 h, there was an almost 5-fold increase in accumulation of cells in the G2/M phase with a concomitant decrease of cells in S phase. No sub-G0 peaks indicative of apoptosis were observed in any experiments.

To determine if the block in the cell cycle was reversible, the ARE was removed after 24 h of exposure and cells were grown for another 24 h in ARE-free medium. These cells recovered from both the G1/G0 and G2/M blocks. The percentage of cells in the S phase increased approximately to the percentage in the control, indicating the occurrence of DNA synthesis, and a corresponding decrease in G1/G0 and G2/M phases was observed (data not shown). There was no change in the cell cycle of NCM460 cells exposed to 50 µg/ml for 24 h (data not shown).

Figure 4A:
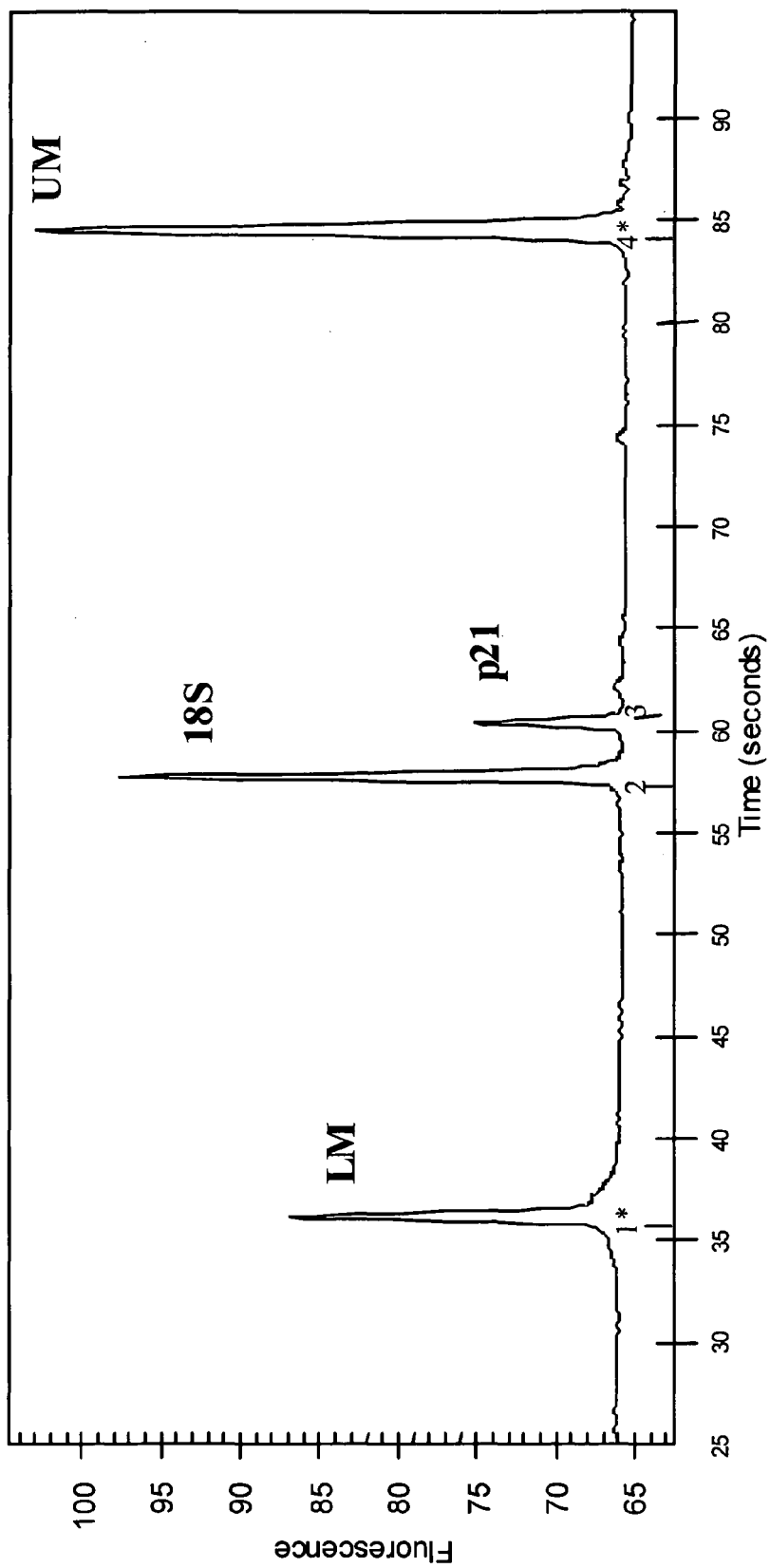
FIGS. 4A-C are electropherograms showing changes in expression of $p21^{WAF1}$ gene relative to 18S gene analyzed by multiplex RT-PCR.
Figure 4B:
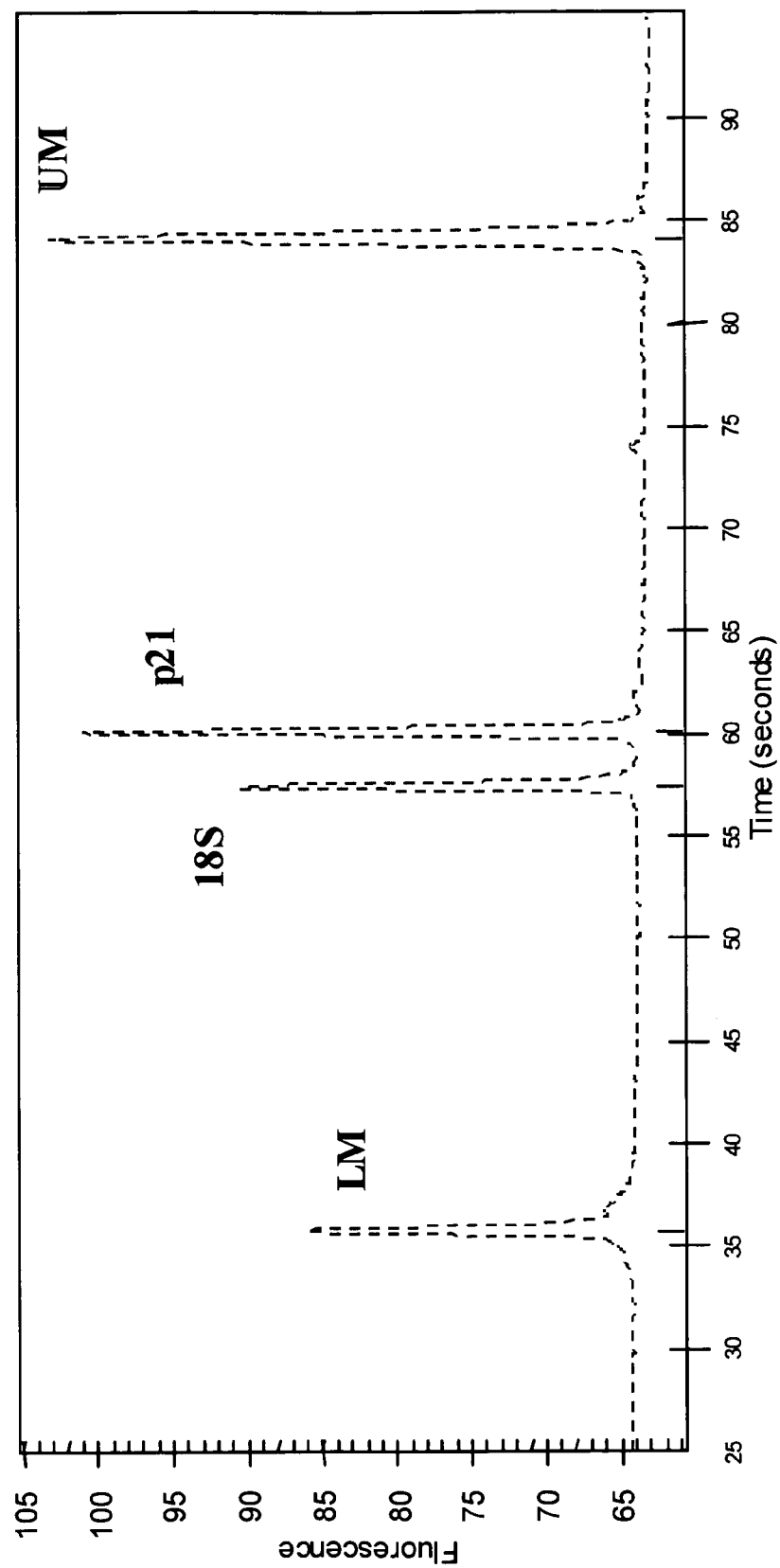
Figure 4C:
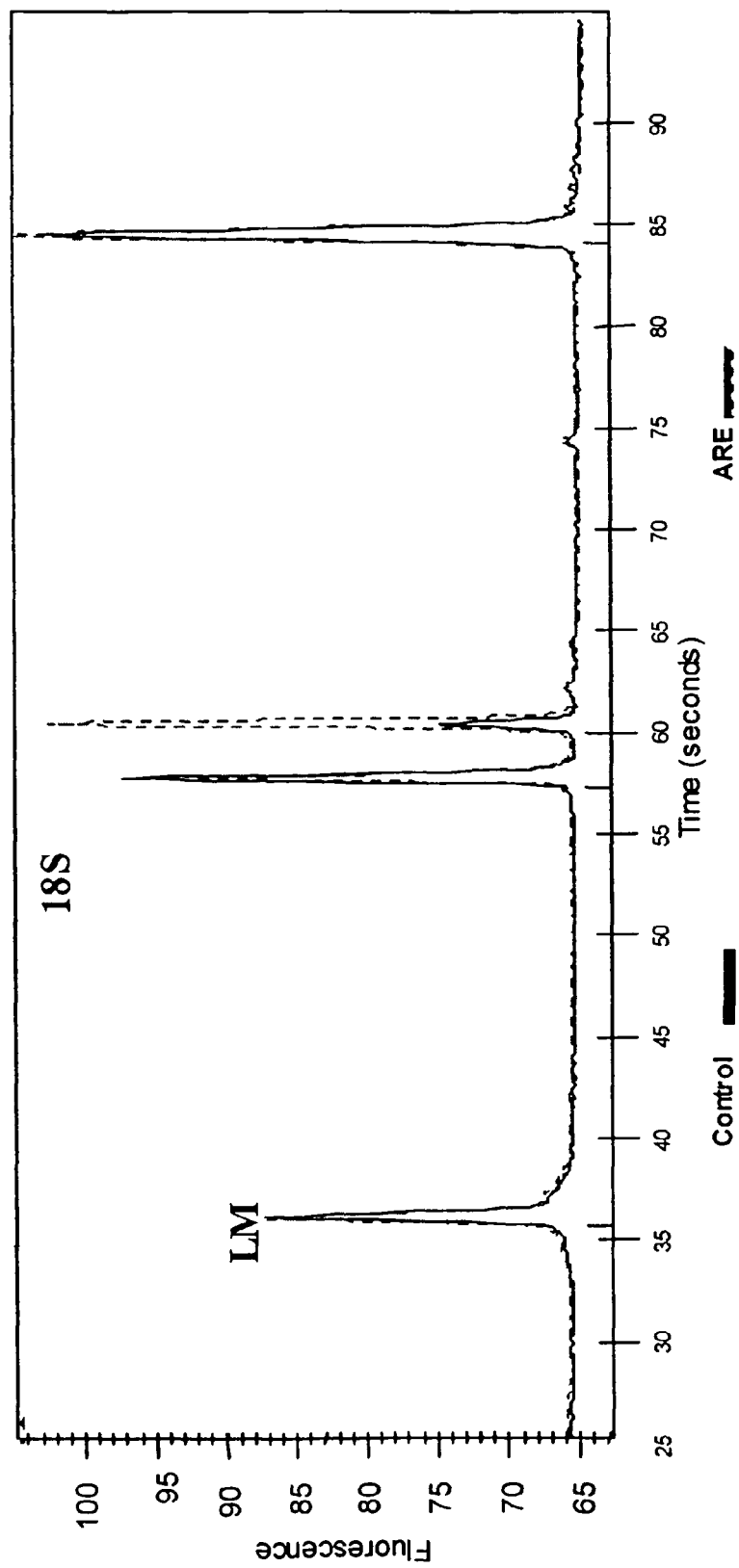
Figure 5:
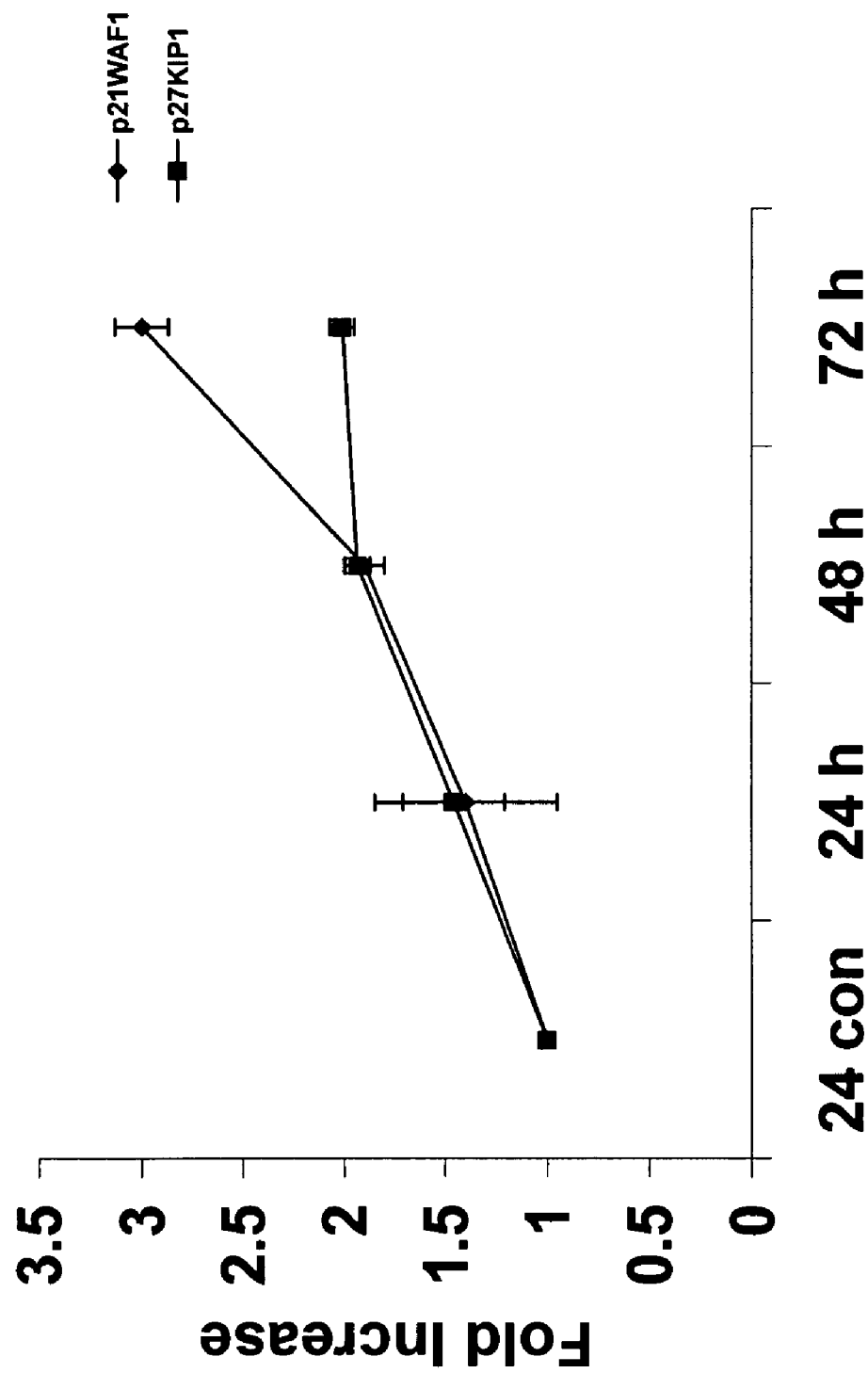
FIG. 5 is a graph showing the fold increases in expression of $p21^{WAF1}$ and $p27^{KIP1}$ genes in HT-29 cells exposed to ARE.
Figure 8A:
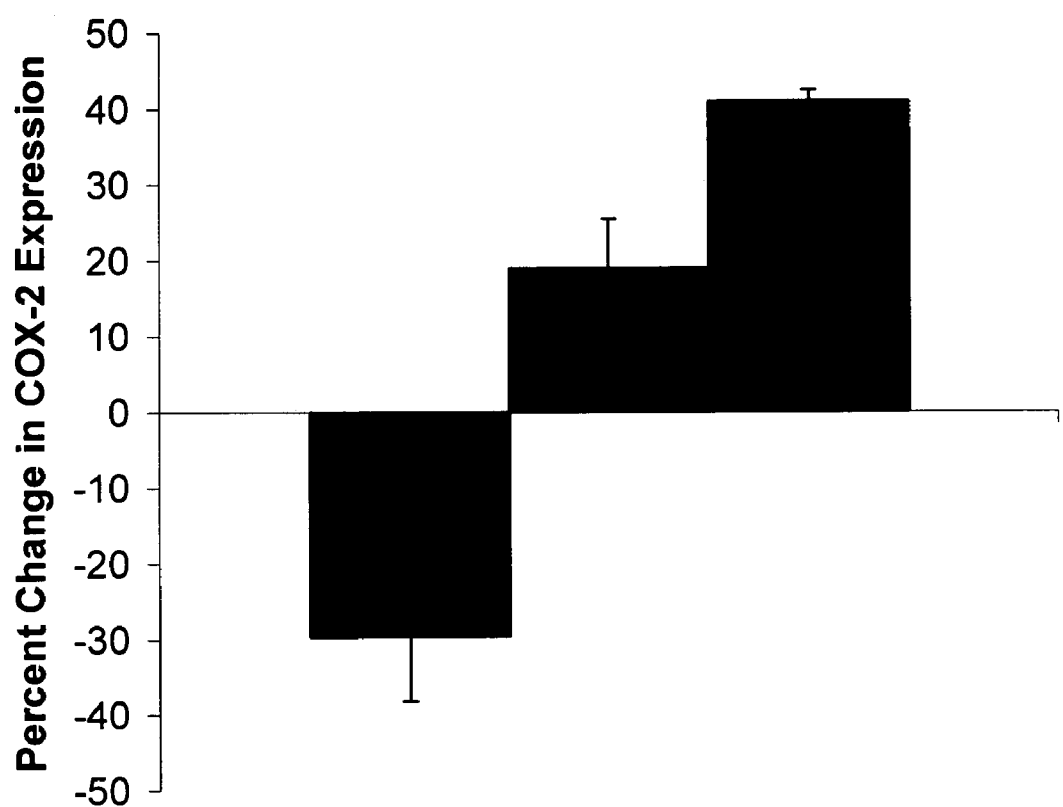
FIGS. 8A-C are graphs showing the effect of ARE exposure on COX-2 in HT-29 cells.
Figure 8B:
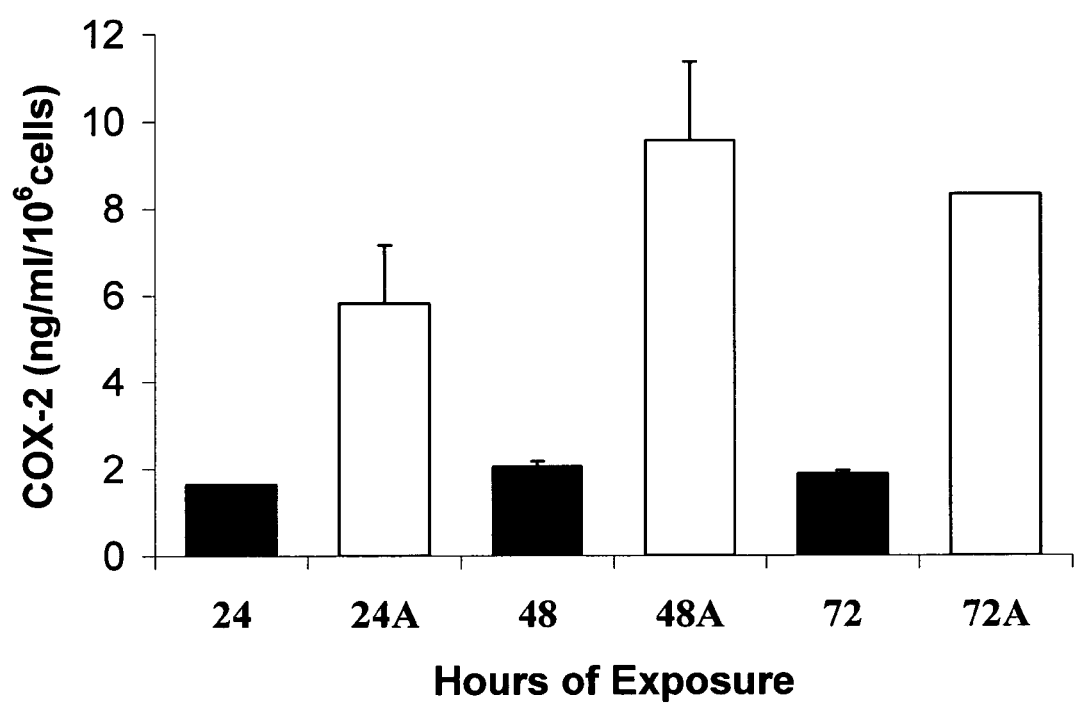

Increased Expression of $p21^{WAF1}$ and $p27^{KIP1}$ Genes in ARE-treated HT-29 Cells—To evaluate the potential molecular mechanism by which the cell cycle is arrested at G1/G0 phase we assessed the expression of cyclin kinase inhibitors, $p21^{WAF1}$ and $p27^{KIP1}$ genes. FIG. 4 (A-C) illustrates the changes in expression of $p21^{WAF1}$ gene in HT-29 cells exposed to ARE. FIG. 8A shows the electropherogram of RT-PCR products from HT-29 cells exposed to vehicle only for 24 h, where the internal control 18S and the $p21^{WAF1}$ genes are represented by peak 2 and peak 3, respectively. FIG. 4B (dashed line) represents the electropherogram of HT-29 cells treated with 50 µg/ml of chokeberry ARE for 24 h. The Agilent 2100 bioanalyzer allows superimposition of the two electropherograms (FIG. 4C) and the increased expression of $p21^{WAF1}$ gene (increased fluorescence of peak 3, dashed line) can be observed. The 18S peak (peak 2), representing the internal control, from exposed as well as the vehicle only control cells show very little change in its expression. The lower marker (LM) and upper Marker (UM) provided by the manufacturers are perfectly aligned. The increase in expression of $p21^{WAF1}$ gene in ARE treated HT-29 cells was observed in time dependent manner, with a 1.5 fold increase seen within 24 h of exposure. At the end of 72 h the expression of $p21^{WAF1}$ increased by 3 fold as compared to control cells (FIG. 5). No significant change in $p21^{WAF1}$ expression was observed in NCM460 cells exposed to 50 µg/ml ARE (data not shown).

The $p27^{KIP1}$ gene expression demonstrated a similar pattern of regulation in the HT-29 cells exposed to ARE. As observed in FIG. 5 the expression of $p27^{KIP1}$ gene increased by 2 fold in HT-29 cells exposed to 50 µg/ml ARE for 48 h, and there was no further increase observed by 72 h of exposure, as compared to cells exposed to vehicle alone. NCM460 cells showed negligible difference in expression of $p27^{KIP1}$ gene in exposed cells compared to control cells (data not shown).

Figure 6:
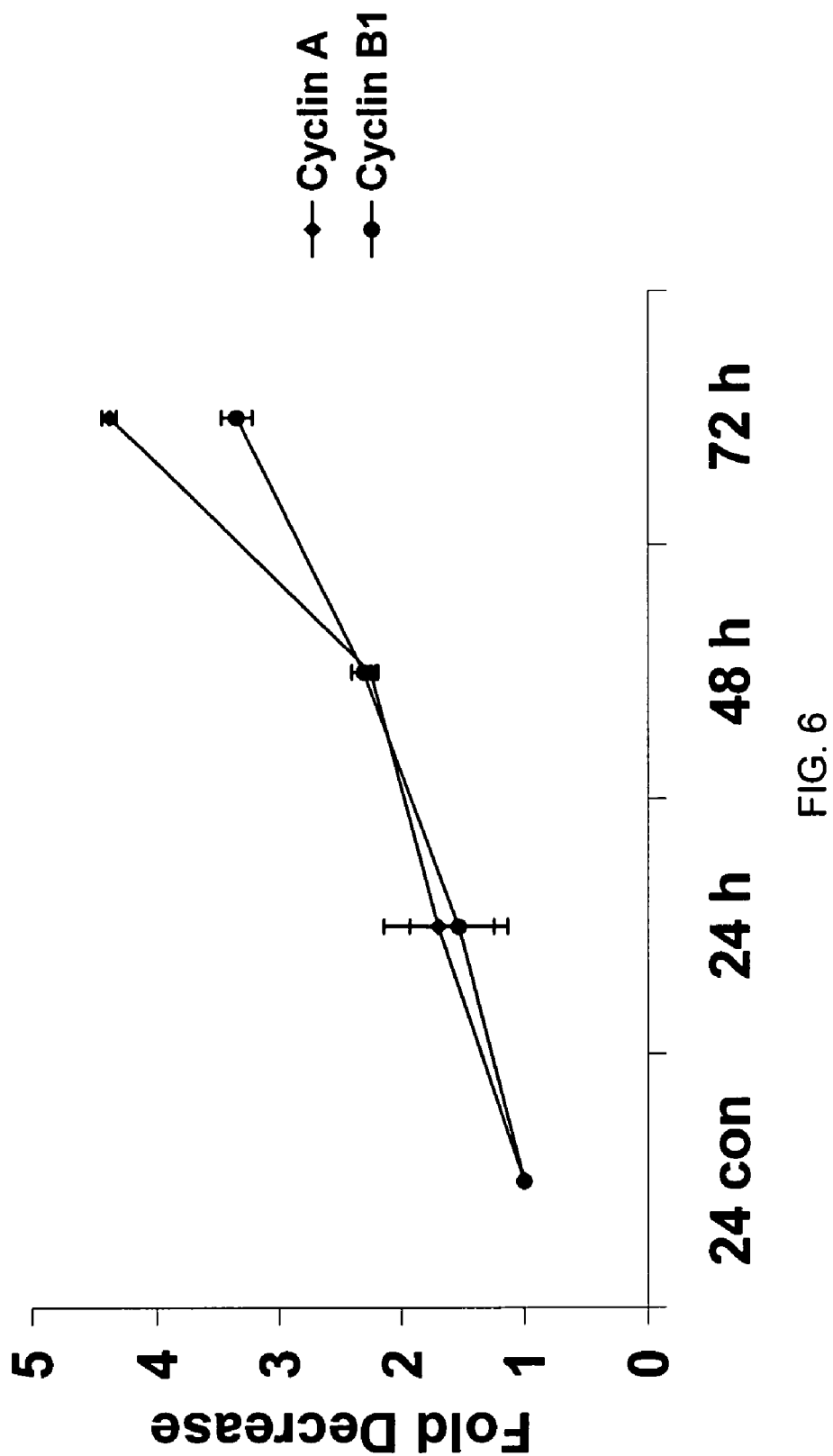
FIG. 6 is a graph showing fold decreases in expression of Cyclin A and Cyclin B1 genes in HT-29 cells exposed to 50 µg/ml of ARE for 24 h, 48 h and 72 h.

Chokeberry ARE-treated HT-29 Cells show a Decreased Expression of Cyclin Genes—Inhibition of expression of Cyclin A and Cyclin B genes was consistent with the blockage of HT-29 cells at the G2/M phase of the cell cycle (FIG. 6). The inhibition of both genes was observed in a time dependent manner. As seen in FIG. 6 at the end of 72 h of exposure to ARE HT-29 cells demonstrated 3-4 fold inhibition in the mRNA levels of Cyclin B1 and Cyclin A genes, respectively.

Figure 7A:
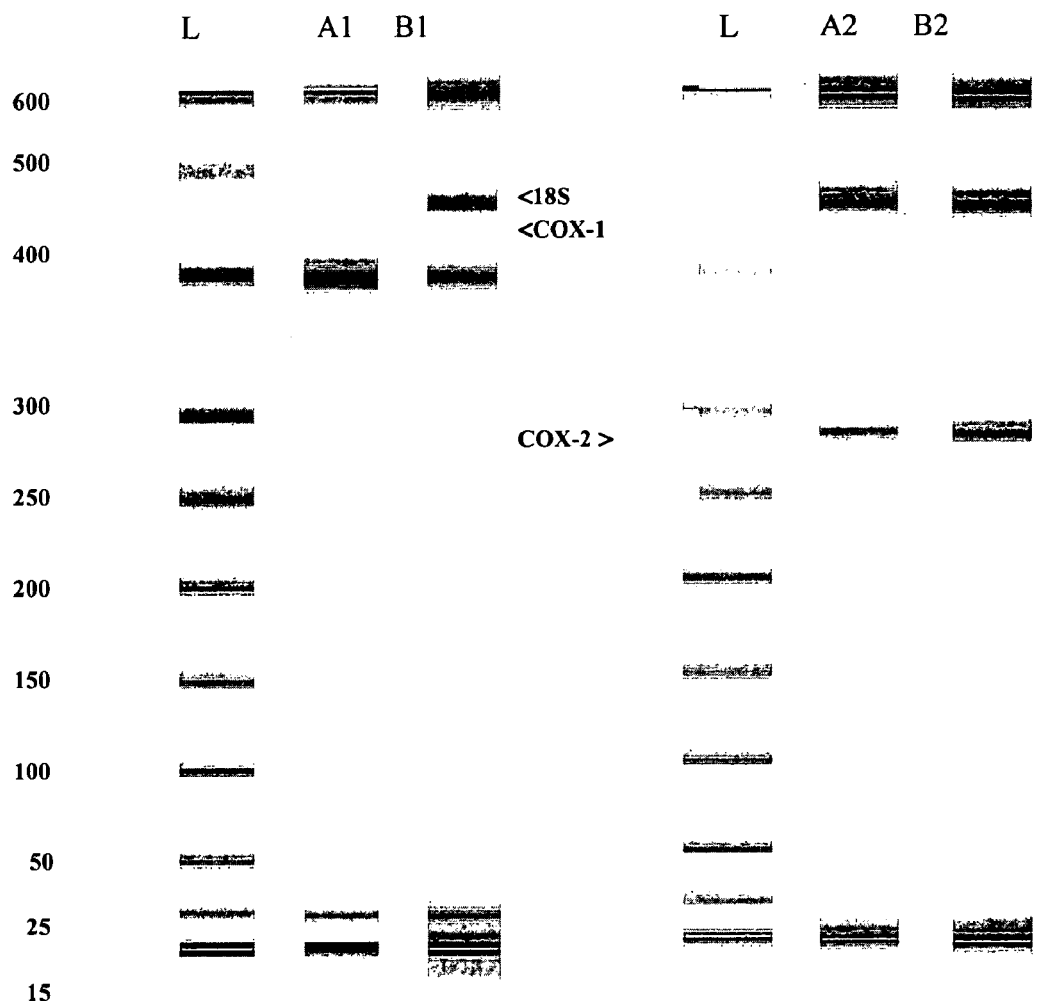
FIGS. 7A-B shows the basal level expression of COX-1 and COX-2 genes in colon cell lines NCM460 and HT-29.
Figure 7B:
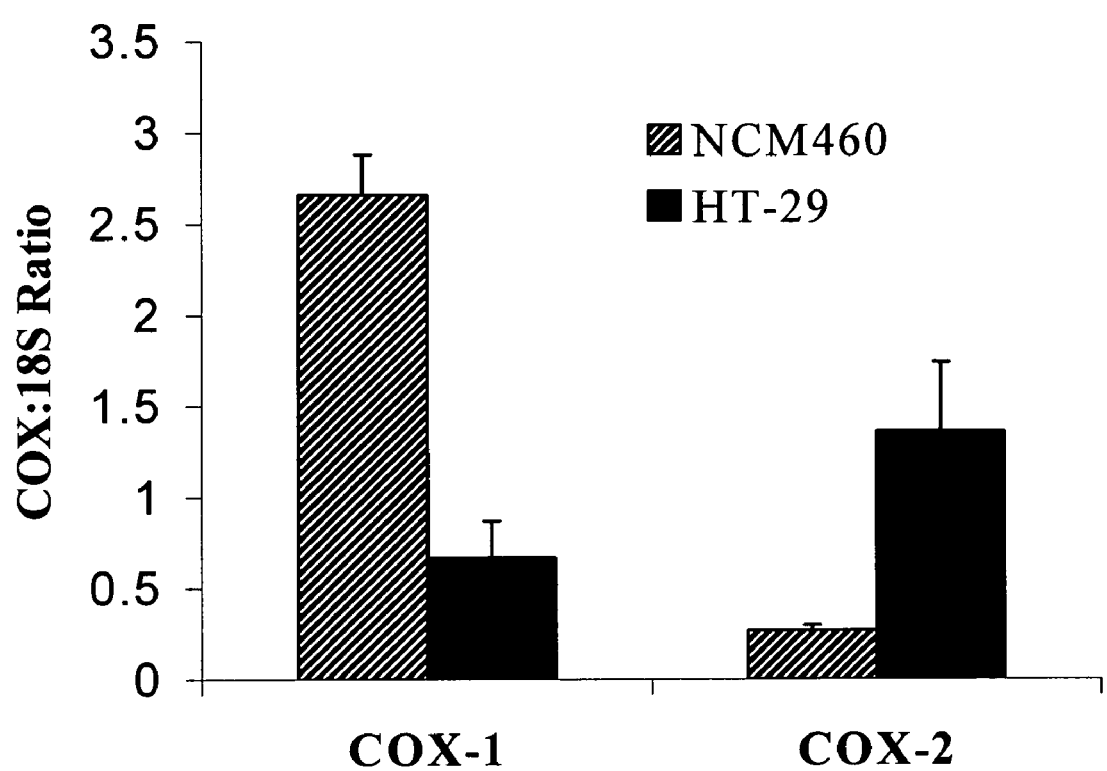

NCM460 Cells Express Higher Levels of COX-1 and Lower COX-2 as Compared to HT29 Cells—In the present study, both COX-1 and COX-2 genes were expressed in HT-29 and NCM460 cells as measured by RT-PCR (FIG. 7A). As seen in gel image from Agilent 2100 bioanalyzer, expression of the COX-1 gene (401 bp, lane A1) in normal NCM460 cells was higher than expression of the COX-2 gene (297 bp, lane A2). In contrast, HT-29 cells derived from colon adenocarcinoma had highly expressed COX-2 gene (lane B2) as compared to the COX-1 gene (lane B1). FIG. 7B represents data from two separate experiments. NCM460 cells demonstrate almost 4 fold higher expression of COX-1 gene as compared to the expression in HT-29 cells. The normal cells also demonstrate a low level of COX-2 gene expression.

Figure 8C:
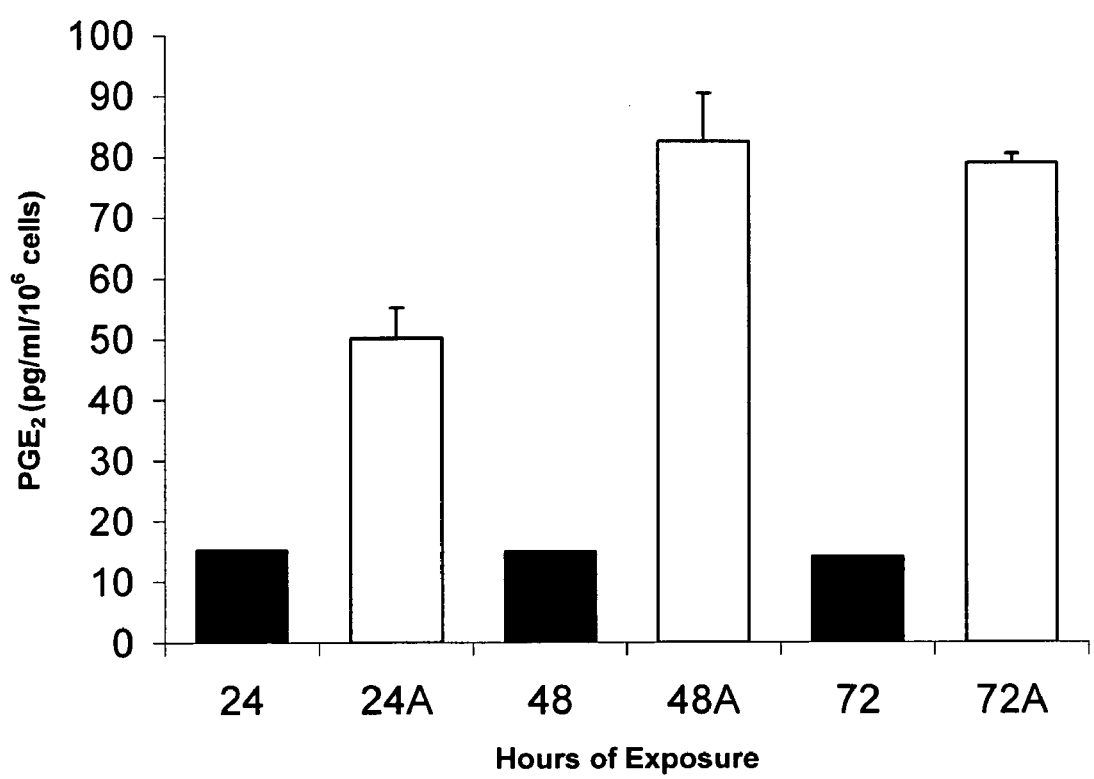

Effect of Chokeberry ARE on COX-2 Gene Expression and Activity—Chokeberry ARE inhibited COX-2 gene expression in HT-29 cells within 24 h in a concentration dependent manner, with exposures to as low as 10 µg/ml chokeberry ARE (data not shown). At 50 µg/ml chokeberry ARE exposure for 24 h the inhibition of COX-2 gene expression in HT-29 cells averaged a 32% decrease (FIG. 8A). However, this was a transient effect. With increased time of exposure up to 48 h and 72 h, the COX-2 gene in HT-29 cells showed an increased expression to almost 40%, when compared to cells grown in vehicle control media (FIG. 8A). No significant change in COX-1 gene expression was observed in HT-29 cells (data not shown). Normal colon cells, NCM460 cells did not show a significant change in expression of either COX-1 or COX-2 genes (data not shown). We further determined if COX-2 protein expression and $PGE_2$ production in HT-29 cells exposed to ARE followed a similar pattern as COX-2 gene expression. COX-2 protein (FIG. 18) and activity as measured by $PGE_2$ production (FIG. 8C) was elevated in cells treated with chokeberry ARE at all time points.

Discussion

We report that commercially available extract from chokeberry fruits, rich in anthocyanins, can inhibit the growth of colon cancer cells without affecting the growth of normal colon cells in vitro. HPLC analysis of the commercially available chokeberry ARE illustrated that it is a mixture of phenolic compounds with cyanidin-3-galactoside as the predominant anthocyanin. Almost 70% of total anthocyanins in chokeberry ARE is cyanidin-3-galactoside. The colon cancer cells, HT-29 exposed to chokeberry ARE demonstrated more than 65% growth inhibition within 24 hours of exposure and high cell viability suggesting a cytostatic inhibition. Similar cytostatic inhibition of cell proliferation and differentiation by anthocyanins was reported by Kamei et al. (10), who demonstrated that anthocyanins, such as delphinidin, cyanidin, and pelargonidin, significantly inhibited HCT-15 intestinal cancer cell growth as compared with other flavonoids. There are few literature reports of the effects of anthocyanins or other flavonoids on growth of cells derived from normal tissue, although growth of WI-38 fibroblasts from normal lung was suppressed by anthocyanin and other flavonoids derived from petals of Rosa and Chrysanthemum (10). We demonstrated for the first time that NCM460 cells, which are epithelial cells derived from the normal colon (17), grow normally in presence of the chokeberry extract. Less than 10% growth inhibition was observed when the normal cells were exposed for as long as 48 h. This inhibition was not significant when compared to the 90% growth inhibition observed in HT-29 colon cancer cells after 48 h of exposure. Therefore, chokeberry ARE was able to specifically inhibit growth of colonic cancer cells but not normal colonic cells.

One of the mechanisms of cell growth inhibition is the alteration of movement of cells through the cell cycle. Different anthocyanins have been reported to affect the cell cycle at different phases (11, 18, 19). Exposed to anthocyanidins from grape rind and red rice, HCT-15 cells were arrested at the S phase (11). Anthocyanin fractions extracted from rose petals, and red and white wines, and synthetic cytostatic agents arrested the cells at various stages, including G1, S, and G2/M phases of cell cycle (18, 19).

Cell cycle progression is regulated by interaction between cyclin-dependent kinases (CDKs) and cyclins, members of cell cycle regulators, that bind to and activate CDKs. Cyclin-dependent kinase inhibitors (CDKIs) also play a critical role in controlling cell cycle progression by negatively regulating the CDK activities (20-22). Two CDKIs, $p21^{WAF1}$ and $p27^{KIP1}$ are related proteins, which bind to cyclin-CDK complexes and causes arrest in the G1 phase of the cell cycle (23). We evaluated the effect of chokeberry ARE on cell cycle of HT-29 and NCM460 cells using flow cytometry. Within 24 h of exposure to ARE an increased percentage of HT-29 cells were observed in G1/G0 phase indicating a block at that cell cycle checkpoint. In our study, ARE-induced G1/G0 cell cycle arrest coincided with a marked increase in expression of $p21^{WAF1}$ and $p27^{KIP1}$ genes and was strongly dependent on time of exposure to ARE. The movement of the cells from the S phase into the G2/M phase appears to continue as observed by the decreasing percentage of cells in S phase. Accumulation of the ARE exposed cells in the G2/M phase suggests that the cells are not reentering the G1/G0 phase of the cell cycle. The G2/M block can be attributed to increased inhibition of Cyclin A and Cyclin B1 genes, as observed in the HT-29 cells that were exposed to ARE as compared to the control cells.

Similar changes in cyclins and CDKIs have been reported in colon cancer cells in response to various phytochemicals. Down regulation of Cyclin A expression and up regulation of $p21^{WAF1}$ and $p27^{KIP1}$ resulting in cell cycle arrest of various colon cancer cells on exposure to β-carotene, a carotenoid (24) and tangeretin, a flavonoid (25) are some examples. The increased expression of $p21^{WAF1}$ gene due to ARE exposure can also be responsible for block at both the G1/G0 and G2/M phases of the cell cycle. The $p21^{WAF1}$ CDKI has broad specificity and is able to inhibit G1 as well as G2 phase cyclin-CDK complexes resulting in a block at both phases of the cell cycle (26). This has been demonstrated in human prostrate and mammary cancer cell lines in response to genistein (27, 28). The $p21^{WAF1}$ can be upregulated in both p53 dependent and independent manner (29), and as HT-29 cell line is known to have a mutated p53 the induction of $p21^{WAF1}$ gene expression in these cells can be presumed to be independent of p53 status.

Dual blockage at G1/G0 and G2/M phases by chokeberry ARE exposed HT-29 cells appears to be unique though further identification of the active compounds in this semi-purified extract is required. Interestingly, chokeberry ARE does not appear to induce apoptosis at concentrations of up to 50 μg/ml as was observed by the lack of the apoptotic peak (sub-G0) in the cell cycle analysis. Chokeberry ARE did not affect the cell cycle or expression of any of the cell cycle genes in normal colon cells which supports the hypothesis that cancer cell growth inhibition by ARE is due to inhibition of cell cycle events.

An up-regulation in the expression of COX-2 has been observed in colorectal adenomas and carcinomas with an increase of COX-2 mRNA in 86% of carcinomas compared with normal mucosa (30). Cyclooxygenase enzymes catalyze the oxygenation of arachidonic acid, leading to formation of prostaglandins. There are two isoforms of cyclooxygenase; COX-1 is constitutively expressed in all body tissues, also termed as having a 'housekeeping' role. The other isoform is COX-2, which is induced, or up regulated in response to inflammation (31). There is controversy over whether a basal concentration of COX-2 gene is expressed in all tissue (32). We were able to show that cell line NCM460 derived from normal colon mucosa demonstrates a very low level of COX-2 gene expression as compared to the COX-1 gene that is constitutively expressed. On the other hand, high expression of COX-2 gene in colon cancer cell line HT-29 has been shown previously (33, 34).

Numerous epidemiological studies have shown that inhibition of COX genes is linked to colon cancer prevention and drugs, especially non-steroidal anti-inflammatory drugs (NSAIDs), which inhibit the COX-2 enzyme, can delay or prevent colon cancer (35, 36). Inhibition of the activity of purified cyclooxygenase enzyme, in vitro, by anthocyanin fractions isolated from different berries was reported recently (37, 38). Seeram et al (38) demonstrated that the anthocyanins cyanidin-3-glucosylrutinoside and cyanidin-3-rutinoside from raspberries and sweet cherries inactivated COX-1 and COX-2 enzymes. Therefore, we investigated if the effect of the ARE on HT-29 cell proliferation may be due to inhibition of cyclooxygenase expression or activity. NCM460 derived from normal epithelial cells of colon showed a basal level of COX-2 RNA that was not altered by exposure to chokeberry ARE. Comparatively, basal levels of COX-2 RNA are higher in HT-29 cells derived from colon adenocarcinoma. The difference in basal levels of cyclooxygenase expression of the two cell lines supported the hypothesis that the different growth response of the two cell lines to chokeberry ARE may be through a COX-dependent mechanism. However, further experimentation illustrated that although 24 h exposure to ARE decreased the level of COX-2 mRNA in HT-29 cells, this decrease appeared to be a transient effect. An increase in level of COX-2 gene expression was observed with increased time of exposure of the HT-29 cells to chokeberry ARE. Interestingly, the levels of COX-2 protein and $PGE_2$ were significantly increased in cells treated with ARE, indicating that the mechanism of growth inhibition was not due to COX-2 inhibition. The significance of the increased COX-2 activity in the HT-29 cells is not clear at this time. Although anthocyanins may inhibit the activity of purified COX enzymes in vitro (38), the growth inhibition of HT-29 cells by the chokeberry anthocyanin-rich extract does not involve suppression of COX-2 activity and may act in a COX-independent manner. It has been observed that NSAIDs like celecoxib also affect growth of colorectal cancer cells in a COX-independent manner (39) and it is suggested that the mechanism may involve the peroxisome proliferator-activated receptor (PPAR) family of nuclear hormone receptors, inhibition of the NF-κB pathway, or expression of the cell cycle genes (40-41).

Conclusion

In conclusion, anthocyanin-rich extract from chokeberry specifically inhibited the growth and cell cycle progression in colon carcinoma cells mainly through up regulation of CDKIs, p21$^{WAF1}$ and p27$^{KIP1}$ and down regulation of cyclin A and cyclin B1. Little to no effect of the ARE was observed on the growth of normal colon cells. Additional studies investigating ARE mediated changes in expression and activity of genes involved in cell cycle are underway. Additionally, cyanidin-3-galactoside, the major anthocyanin found in the extract of chokeberry ARE, may have an effect on growth and cellular mechanisms of colon cancer cell lines.

Example 1 References

1. Yang C S, Landau J M, Huang M T, and Newmark H L: Inhibition of carcinogenesis by dietary polyphenolic compounds. *Annu Rev Nutr* 21, 381-406, 2001.
2. Scalbert, A, and Williamson, G: Dietary intake and bioavailability of polyphenols. *J Nutr* 130, 2073S-2085S, 2000.
3. Timberlake C F, and Bridle P: Anthocyanins: colour augmentation with catechin and acetaldehyde. *J Sci Food Agric* 28, 539-544, 1977.
4. Cao G, and Prior R L: Anthocyanins are detected in human plasma after oral administration of an elderberry extract. *Clin Chem* 45, 574-576, 1999.
5. Degenhardt A, Knapp H, and Winterhalter P: Separation and purification of anthocyanins by high-speed countercurrent chromatography and screening for antioxidant activity. *J Agric Food Chem* 48, 338-343, 2000.
6. Borissova P, Valcheva S, and Belcheva A: Antiinflammatory effect of flavonoids in the natural juice from *Aronia melanocarpa*, rutin and rutin-magnesium complex on an experimental model of inflammation induced by histamine and serotonin. *Acta Physiol Pharmacol Bulg* 20, 25-30, 1994.
7. Kresty L A, Morse M A, Morgan C, Carlton P S, Lu J et al.: Chemoprevention of esophageal tumorigenesis by dietary administration of lyophilized black raspberries. *Cancer Res* 61, 6112-6119, 2001.
8. Jankowski A, Jankowska B, and Niedworok J: The influence of *Aronia melanocapra* in experimental pancreatitis. *Pol Merkuriusz Lek* 8, 395-398, 2000.
9. Xue H, Aziz R M, Sun N, Cassady J M, Kamendulis L M, et al.: Inhibition of cellular transformation by berry extracts. *Carcinogenesis* 22, 351-356, 2001.
10. Kamei H, Kojima T, Hasegawa M, Koide T, Umeda T, et al.: Suppression of tumor cell growth by anthocyanins in vitro. *Cancer Invest* 13, 590-594, 1995.
11. Koide T, Kamei H, Hashimoto Y, Kojima T, and Hasegawa M: Antitumor effect of hydrolyzed anthocyanin from grape rinds and red rice. *Cancer Biother Radiopharm* 11, 273-277, 1996.
12. Koide T, Hashimoto Y, Kamei H, Kojima T, Hasegawa M, et al.: Antitumor effect of anthocyanin fractions extracted from red soybeans and red beans in vitro and in vivo. *Cancer Biother Radiopharm* 12, 277-280, 1997.
13. Kuntz S, Wenzel U, and Daniel H: Comparative analysis of the effects of flavonoids on proliferation, cytotoxicity, and apoptosis in human colon cancer cell lines. *Eur J Nutr* 38, 133-342, 1999.
14. Hagiwara A, Miyashita K, Nakanishi T, Sano M, Tamano S, et al.: Pronounced inhibition by a natural anthocyanin, purple corn color, of 2-amino-1-methyl-6-phenylimidazo[4,5-b]pyridine (PhIP)-associated colorectal carcinogenesis in male F344 rats pretreated with 1,2-dimethylhydrazine. *Cancer Lett* 171, 17-25, 2001.
15. Giusti M M, and Wrolstad R E: Characterization of red radish anthocyanins. *J Food Sci* 61, 322-326, 1996.
16. Park J B, and Schoene N: Synthesis and characterization of N-coumaroyltyramine as a potent phytochemical which arrests human transformed cells via inhibiting protein tyrosine kinases. *Biochem Biophys Res Commun* 292, 1104-1110, 2002.
17. Moyer M P M, Merriman R L, Stauffer J S, and Tanzer L R: NCM460 a normal human colon mucosal epithelial cell line. *In Vitro Cell Devel Biol* 32, 315-317, 1996.
18. Koide T, Kamei H, Hashimoto Y, Kojima T, Terabe K, et al.: Influence of flavonoids on cell cycle phase as analyzed by flow-cytometry. *Cancer Biother. Radiopharm* 12, 111-115, 1997.
19. Kamei H, Hashimoto Y, Koide T, Kojima T, and Hasegawa M: Anti-tumor effect of methanol extracts from red and white wines. *Cancer Biother Radiopharm* 13, 447-452, 1998.
20. el-Deiry W S, Tokino T, Velculescu V E, Levy D B, Parsons R, et al.: WAF1, a potential mediator of p53 tumor suppression. *Cell* 75, 817-825, 1993.
21. Harper J W, Adami G R, Wei N, Keyomarsi K, and Elledge S J: The p21 Cdk-interacting protein Cip1 is a potent inhibitor of G1 cyclin-dependent kinases. *Cell* 75, 805-816, 1993.
22. Gartel A L, Serfas M S, and Tyner A L. p21-negative regulator of the cell cycle. *Proc Soc Exp Biol Med* 213, 138-149, 1996.
23. Sherr C J, and Roberts J M: CDK inhibitors: positive and negative regulators of G1-phase progression. *Genes Dev* 13, 1501-1512, 1999.
24. Palozza P, Serini S, Maggiano N, Angelini M, Boninsegna A, et al.: Induction of cell cycle arrest and apoptosis in human colon adenocarcinoma cell lines by beta-carotene through down-regulation of cyclin A and Bcl-2 family proteins. *Carcinogenesis* 23, 11-18, 2002.
25. Pan M H, Chen W J, Lin-Shiau S Y, Ho C T, and Lin J K: Tangeretin induces cell-cycle G1 arrest through inhibiting cyclin-dependent kinases 2 and 4 activities as well as elevating Cdk inhibitors p21 and p27 in human colorectal carcinoma cells. *Carcinogenesis* 23, 1677-1684, 2002.
26. Cayrol C, Knibiehler M, and Ducommun B: p21 binding to PCNA causes G1 and G2 cell cycle arrest in p53-deficient cells. *Oncogene* 16, 311-320, 1998.
27. Choi Y H, Lee W H, Park K Y and Zhang L: p53-independent induction of p21 (WAF1/CIP1), reduction of cyclin B1 and G2/M arrest by the isoflavone genistein in human prostate carcinoma cells. *Jpn J Cancer Res* 91, 164-173, 2000.
28. Frey R S, Li J, and Singletary K W: Effects of genistein on cell proliferation and cell cycle arrest in normeoplastic human mammary epithelial cells: involvement of Cdc2, p21$^{waf/Cip1}$, p27$^{kip1}$, and Cdc25C expression. *Biochem Pharmacol* 61, 979-989, 2001.
29. Gartel A L, and Tyner A L: Transcriptional regulation of the p21(WAF1/CIP1) gene. *Exp Cell Res* 246, 280-289, 1999.
30. Eberhart C E, Coffey R J, Radhike A, Giardiello F M, Ferrenbach S, et al.: Up-regulation of cyclooxygenase 2 gene expression in human colorectal adenomas and adenocarcinomas. *Gastroenterology* 107, 1183-1188, 1994.
31. Smith W L, DeWitt D L, and Garavito R M: Cyclooxygenases: structural, cellular, and molecular biology. *Ann Rev Biochem* 69, 145-182, 2000.
32. O'Neill G, and Fordhutchinson A: Expression of mRNA for cyclooxygenase-1 and cyclooxygenase-2 in human tissues. *FEBS Lett* 330, 156-160, 1993.

33. Shao J, Sheng H, Inoue H, Morrow J D, and DuBois R N: Regulation of constitutive cyclooxygenase-2 expression in colon carcinoma cells. *J Biol Chem* 275, 33951-33956, 2000.
34. Battu S, Chable-Rabinovitch H, Rigaud M, and Beneytout J L: Cyclooxygenase-2 expression in human adenocarcinoma cell line HT-29c1.19A. *Anticancer Res* 18, 2397-2404, 1998.
35. DuBois R N, Giardiello F M, and Smaley W E: Nonsteroidal anti-inflammatory drugs, eicosanoids and colorectal cancer prevention. *Gastroenterology Clinics N Am* 25, 773-791, 1996.
36. Prescott S M, and Fitzpatrick F A: Cyclooxygenase-2 and carcinogenesis. *Biochim Biophys Acta* 1470, M69-M78, 2000.
37. Seeram N P, Schutzki R, Chandra A, and Nair M G: Characterization, quantification, and bioactivities of anthocyanins in Cornus species. *J Agric Food Chem* 50, 2519-2523, 2002.
38. Seeram N P, Momin R A, Nair M G, and Bourquin L D: Cyclooxygenase inhibitory and antioxidant cyanidin glycosides in cherries and berries. *Phytomedicine* 8, 362-369, 2001.
39. Grosch S, Tegeder I, Niederberger E, Brautigam L, and Geisslinger G: COX-2 independent induction of cell cycle arrest and apoptosis in colon cancer cells by the selective COX-2 inhibitor celecoxib. *FASEB J* 15, 2742-2744, 2001.
40. Wang C, Fu M, D'Amico M, Albanese C, Zhou J-N, et al.: Inhibition of cellular proliferation through IkB kinase-independent and Peroxisome Proliferator-Activated Receptor g-dependent repression of cyclin D1. *Mol Cell Biol* 21, 3057-3070, 2001.
41. Gupta R A, and DuBois R N: Colorectal cancer prevention and treatment by inhibition of cyclooxygenase-2. *Nature Reviews Cancer* 1, 11-21, 2001.
42. NAS/NRC. The 1977 survey of industry on the use of food additives: estimates of daily intake. *Nat Acad Sci/Nat Res Council* 3, Washington D.C. 1979.

Example 2

Characterization of Anthocyanin Rich Extracts Having Biological Activity

Anthocyanins are the pigments responsible for the bright attractive red, orange, purple, blue colors of most fruits and vegetables. Through the centuries anthocyanin-containing products have been consumed without apparent adverse effects. They have served as tools for botanical classification since they can be used as a fingerprint that identifies a commodity. Also, anthocyanins have found considerable potential in the food industry as safe and effective food colorants (Strack and Wray 1994, Giusti and Wrolstad 1996). The worldwide demand for more "natural" ingredients coupled with the discovery of acylated and polyacylated anthocyanins with increased stability have made these pigments even more attractive to the food industry as alternatives to the use of artificial dyes (Bassa and Francis 1987; Baublis and Berber Jimenez 1995; Giusti and Wrolstad 1996; Rodriguez-Saona and others 1998).

The chemical structure of anthocyanin compounds plays an important role on food systems. Anthocyanins belong to the flavonoid group of compounds. Although flavonoids are generally colorless, anthocyanins occur in the cell sap in chemical states strongly absorbing visible light (Brouillard, 1983). Anthocyanins are glycosides of anthocyanidin (aglycon) chromophores, these being polyhydroxy and polymethoxy derivatives of 2-phenylbenzopyrylium (flavylium) salts (Jackman and Smith, 1996; Brouillard, 1982). There are only 6 major anthocyanidins found in nature (Table 2) in spite of the great variety of plant colors (Goto, 1987).

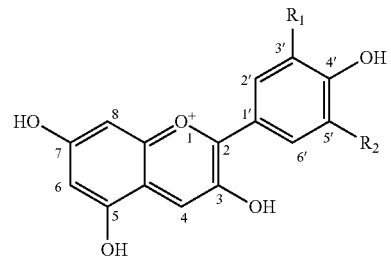

| | Substitution | | $\lambda_{max}$ (nm) |
|---|---|---|---|
| Aglycon | R1 | R2 | visible spectra |
| Pelargonidin | H | H | 494 (orange) |
| Cyanidin | OH | H | 506 (Orange-red) |
| Delphinidin | OH | OH | 508 (Bluish-red) |
| Peonidin | OMe | H | 506 (Orange-red) |
| Petunidin | OMe | OH | 508 (Bluish-red) |
| Malvidin | OMe | OMe | 510 (Bluish-red) |

Table 2 Chemical Structure and spectral characteristics of anthocyanidins commonly found in nature Anthocyanidins are rarely found in their free form in plant tissues and occur mainly in the glycosylated forms (Harborne, 1979). The most common sugars substituted on the aglycone are glucose, rhamnose, xylose, galactose, arabinose, and fructose. They occur as mono-, di- (sophorose, rutinose, gentiobiose, laminaribiose) and tri-glycosides (Francis, 1989).

There is a wide variety of chemical structures that can be encountered among anthocyanins: different glycosylating patterns, different acylating groups, many different hydroxyl groups available for esterification of the acylating groups and finally presence of cinnamic acids in different stereo isomeric forms (Dangles and others 1993, Giusti and others 1998). The 3-hydroxyl is always replaced by a sugar, which confers stability and solubility to the anthocyanin molecule. When a second sugar is present, it is generally attached to the C-5 hydroxyl. Other glycosylation positions include the 7-, 3'-4' and 5'-hydroxyl groups (Francis 1989; Brouillard 1982) and anthocyanins with five sugars (*Platycodon grandiflorum*) and six sugars (*Ipomoea purpura*) have been reported, being attached to the basic molecule with alternating sugar and acyl acid linkages (Francis 1989). The nature of the sugar residue(s) appears to have a greater influence on anthocyanin stability than the nature of the aglycone, with decreasing stability reported for glycosyl moieties in the order glucose>galactose>arabinose (Jackman and Smith 1996). The sugar residues are often acylated (Formula I) with aromatic acids including p-coumaric, caffeic, ferulic, sinapic, gallic or p-hydroxybenzoic acids, and/or aliphatic acids such as malonic, acetic, malic, succinic or oxalic acids (Jackman and Smith 1996). Acyl substituents are commonly bound to the C-3 sugar, esterified to the 6-OH or less frequently to the 4-OH group of the sugars. However, anthocyanins containing rather complicated acylation patterns attached on different sugar moieties have been reported (Odake and others 1992; Lu and others 1992; Shi and others 1992; Goto 1987). Acylation has an important stabilizing effect on anthocyanins via intramolecular copigmentation. Formula I shows the chemical structure of the highly stable acylated pigments from radish (*Raphanus sativus*). Pigments: pelargonidin-3-sophoroside-5-glucoside acylated with malonic acid and (4) p-coumaric acid or (5) ferulic acid (modified from Giusti and others (1998)).

Formula 1

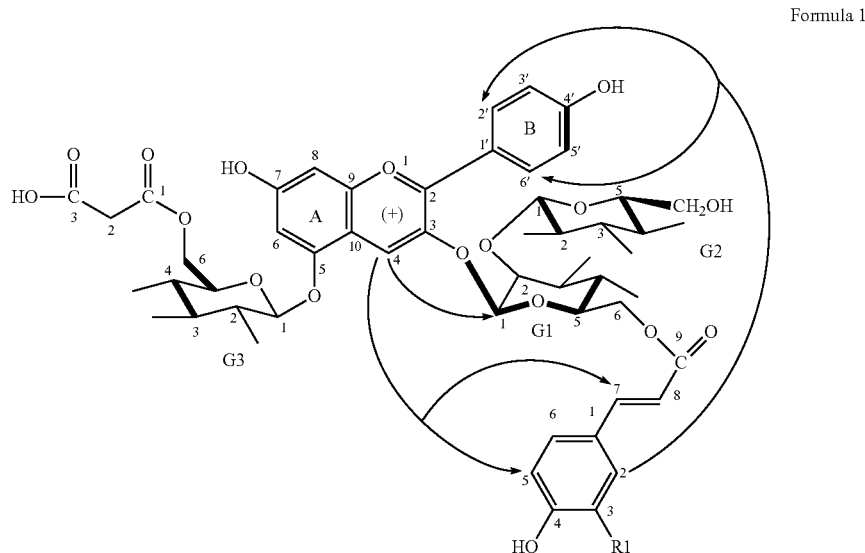

Pigment 4: $R_1 = H$
Pigment 5: $R_1 = OCH_3$

In a recent study (Giusti and others 1999) we compared the effects of glycosylation and acylating on the color characteristics and pigment stability of pelargonidin derivatives. There was a clear impact of glycosylation and acylation on the stability of the compounds. We expect that these chemical characteristics will also have a great impact on the biological activity of these compounds. Acylated anthocyanins would be the best choice as stable colorants to be used by the food industry. However, limited research has been conducted on the potential beneficial effects of acylated anthocyanins.

Anthocyanins have been consumed for thousand of years without any apparent adverse effect on human health (Timberlake 1988; Brouillard 1982). On the contrary, beneficial therapeutical properties have been attributed to anthocyanins. Preparations of anthocyanin-based extracts from wild blueberries and European bilberries (*Vaccinium myrtillus*) are marketed as potent phytochemicals (Timberlake 1988).

Recently, interest in the anthocyanin content of foods and anthocyanin extracts (food colorants) has intensified because of their possible health benefits. Health benefits associated with anthocyanin extracts include enhancement of sight acuteness (Timberlake and Henry 1988), antioxidant capacity (Wang and others 1997; Tamura and Yamagami, 1994; Rice-Evans and others, 1996, Prior and others 1998; Degenhard and others 2000), treatment of various blood circulation disorders resulting from capillary fragility (Timberlake and Henry 1988), vaso-protective and anti-inflammatory properties (Lietti and others 1976), inhibition of platelet aggregation (Morazzoni and Magistretti 1986), maintenance of normal vascular permeability (Timberalke and Henry 1988), controlling diabetes, anti-neoplastic and chemo protective activity (Kamei and others 1995; Karaivanova and others 1990), radiation-protective activity (Akhmadieva and others 1993), and possibly others due to their diverse action on various enzymes and metabolic processes (Wang and others 1997).

A limitation of the study of anthocyanins is that there are very few anthocyanin standards commercially available, making it difficult to work with individual components. Also, most of the studies performed with complex matrixes have lacked chemical characterization of the test material (uncharacterized crude extracts). These limitations are confounded by the vast array of anthocyanins present in nature, and by the complexity of food matrices. Polyphenols Inc, a company based on Norway, has now a number of pure anthocyanins commercially available.

For many biologically active natural compounds, large doses need to be consumed in order to be effective. In the mid 70's, Kuhnau (1976) estimated that the daily intake of anthocyanins in humans in the US was 180-215 mg/day due to their widespread distribution and occurrence in fruits and vegetables. The anthocyanin content of some fruits and vegetables is presented in Table 3. Therefore, the high level of anthocyanins present in the diet may offer an advantage in this regard. There is also potential for drastically increasing anthocyanin consumption by using them as natural alternatives to the use of the artificial dyes to color foods, mainly due to the fact that relatively large doses of anthocyanins pigments (as compared to synthetic dyes) are usually required to confer attractive color to foods.

TABLE 3

Anthocyanin Content of Some Common Fruits and Vegetables

| Source | Pigment content (mg/100 g fresh weight) | Reference |
| --- | --- | --- |
| Apples | 10 | Mazza and Miniati, 1993 |
| Bilberries | 300-320 | Mazza and Miniati, 1993 |
| Blackberries | 83-326 | Mazza and Miniati, 1993 |
| Black currants | 130-400 | Timberlake, 1988 |
| Blueberries | 25-495 | Mazza and Miniati, 1993 |
| Red cabbage | 25 | Timberlake, 1988 |
| Black chokeberries | 560 | Kraem er-Schafhalter et al., 1996 |
| Cherries | 4-450 | Kraem er-Schafhalter et al., 1996 |
| Cranberries | 60-200 | Timberlake, 1988 |
| Elderberry | 450 | Kraem er-Schafhalter et al., 1996 |
| Grapes | 6-600 | Mazza and Miniati, 1993 |
| Kiwi | 100 | Kraem er-Schafhalter et al., 1996 |
| Red Onions | 7-21 | Mazza and Miniati, 1993 |
| Plum | 2-25 | Timberlake, 1988 |
| Red radishes | 11-60 | Giusti et al., 1998 |
| Black raspberries | 300-400 | Timberlake, 1988 |
| Red raspberries | 20-60 | Mazza and Miniati, 1993 |

TABLE 3-continued

Anthocyanin Content of Some Common Fruits and Vegetables

| Source | Pigment content (mg/100 g fresh weight) | Reference |
| --- | --- | --- |
| Strawberries | 15-35 | Timberlake, 1988 |
| Tradescantia pallida (leaves) | 120 | Shi et al., 1992 |

Flavonoids have been intensively investigated due to their possible protective effects against chronic diseases (Bohm and others 1998). Over 5,000 different flavonoids have been described, and they are categorized into flavonols, flavones, catechins, flavanones, anthocyanidins and isoflavonoids. Flavonoids have a variety of biological effects in numerous mammalian cell systems, in vitro as well as in vivo. Recently, much attention has been paid to their antioxidant properties and to their inhibitory role in various stages of tumor development in animal studies (Hollman and Katan 1997, 1999; Rice-Evans and others 1996).

The metabolism of flavonoids has been studied frequently in various animals, but very few data in humans are available. Two major sites of flavonoid metabolism are the liver and the colonic flora (Hollman and Katan 1997). Flavonoids present in foods were considered non-absorbable because they are bound to sugars as beta-glycosides. Only free flavonoids without a sugar molecule, the so-called aglycones, were thought to be able to pass through the gut wall. Hydrolysis only occurs in the colon by microorganisms, which at the same time degrade flavonoids. Recently, Hollman and Katan (1999) found that human absorption of the quercetin glycosides from onions was far better than that of the pure aglycone. The sugar moiety was an important determinant of their absorption and bioavailability. Simultaneously, Miyazawa and coworkers (1999) reported that cyanidin-3-glucoside and cyanidin-3,5-diglucoside were found in the plasma of rats and humans 30 minutes after oral supplementation of the pigments. Cyanidin aglycones or its methylated or conjugated derivatives were not found in the plasma after ingestion of the glucoside forms. These results indicated that anthocyanins are incorporated keeping structurally intact glycoside forms, from the digestive tract into the blood circulation system in mammals.

Wine polyphenolic extract containing anthocyanins, flavonals, phenolic acids, catechin, epecatechin and proanthocyanins significantly reduced the incidence and number of colorectal tumors in F344 rats (Caderni and others 2000). No change in the apoptosis index was observed in the tumors from rats fed the wine extract. The authors concluded that further studies are needed to elucidate which compounds are responsible for the effect, and the mechanism of inhibition. Extracts of red wine that were free of low-mass phenols, including anthocyanins, cathechins and resveratrol did not suppress carcinogen-induced early lesions number or size (Caderni and others 1999). These data suggest that these compounds, either individually, or in combination may be responsible for the anticarcinogenic effect of the wine extracts containing low-mass phenolics.

The potential cancer chemo-preventive activity of different berry derivatives, such as strawberry and blackberry, has been reported by inhibiting the endogenous formation of N-nitrosamines (Hesler and others 1992), reducing the incidence of esophageal tumors (Stoner and other 1997; Kresty and others 1998), and inhibiting cell transformation in the presence of benzo[α]pyrene (Xue and others 2001). Crude methanolic fractions, containing anthocyanin pigments, were used in these studies. However, further identification of the compounds in the fractions responsible for the chemopreventive activity and possible mechanisms involved in these processes are needed.

Recent studies have reported anticancer activity of anthocyanin fractions extracted from different sources including flower petals (Kamei and others 1995); grape rinds and red rice (Koide and others 1996); red soybeans and red beans (Koide and others 1997); Vaccinium species (Bomser and others 1996) and purple corn (Hagiwara and others 2001).

The in vitro study conducted by Kamei and coworkers (1995) showed that the anthocyanin fractions were more effective than other flavonoids for direct cell growth inhibition, and proposed a cytostatic inhibitory mechanism, affecting cell proliferation and differentiation. Different degrees of inhibition of cancerous cell growth and dose responses were also observed with individual isolated anthocyanidins. A 50% cell growth suppression (HCT-15 cells derived from human colon carcinoma) was obtained at 0.5, 2 and 5 μg/ml dose with delphinidin, cyanidin and pelargonidin, respectively.

Using the same HCT-15 model, Koide and coworkers (1996 and 1997) found that different sources of anthocyanins, and even the presence of glycosylations may affect the inhibitory effect of anthocyanin fractions. Also, chemical structure has been correlated with antimutagenic activity, with acylation of anthocyanin with organic acids markedly increasing antimutagenecity of anthocyanin pigments as compared with the deacylated counterparts (Yoshimoto and others 2001). However, the identity and proportions of individual anthocyanins in those extracts is not reported. This information would be required in order to establish structure/function relationships. The potential of a commercial colorant extract obtained from purple corn to inhibit colorectal carcinogenesis was tested in an in vivo system (Hagiwara and others 2001). Colon cancer was initiated with 1,2-dimethylhydrazine in F344 rats and further treatment included dietary supplementation of 5% color extract and 2-amino-1-methyl-6-phenylimidazo[4,5-b] pyridine (PhIP). Colorectal adenomas and carcinomas in rats were clearly induced by PhIP, while lesion development was suppressed by the pigment administration. Even more, the color extract decreased the PhIP induction of aberrant crypt foci. However, the compound(s) in the extract actually responsible for these effects were not identified.

Common characteristics of the studies reported in this Example are that they point to the same conclusion; a potential protective effect against cancer of anthocyanin-containing extracts. These findings suggest that it may be possible to expand the markets of anthocyanin-rich agricultural commodities by identifying anthocyanin-rich products with added value due to the potential biological activity of their components as tested by the inhibition of colon cancer cell proliferation. Further investigation is needed to assign structure/function relationships between components in these extracts and specific biological activity. In this study, we propose to investigate such relationships.

Figure 9:
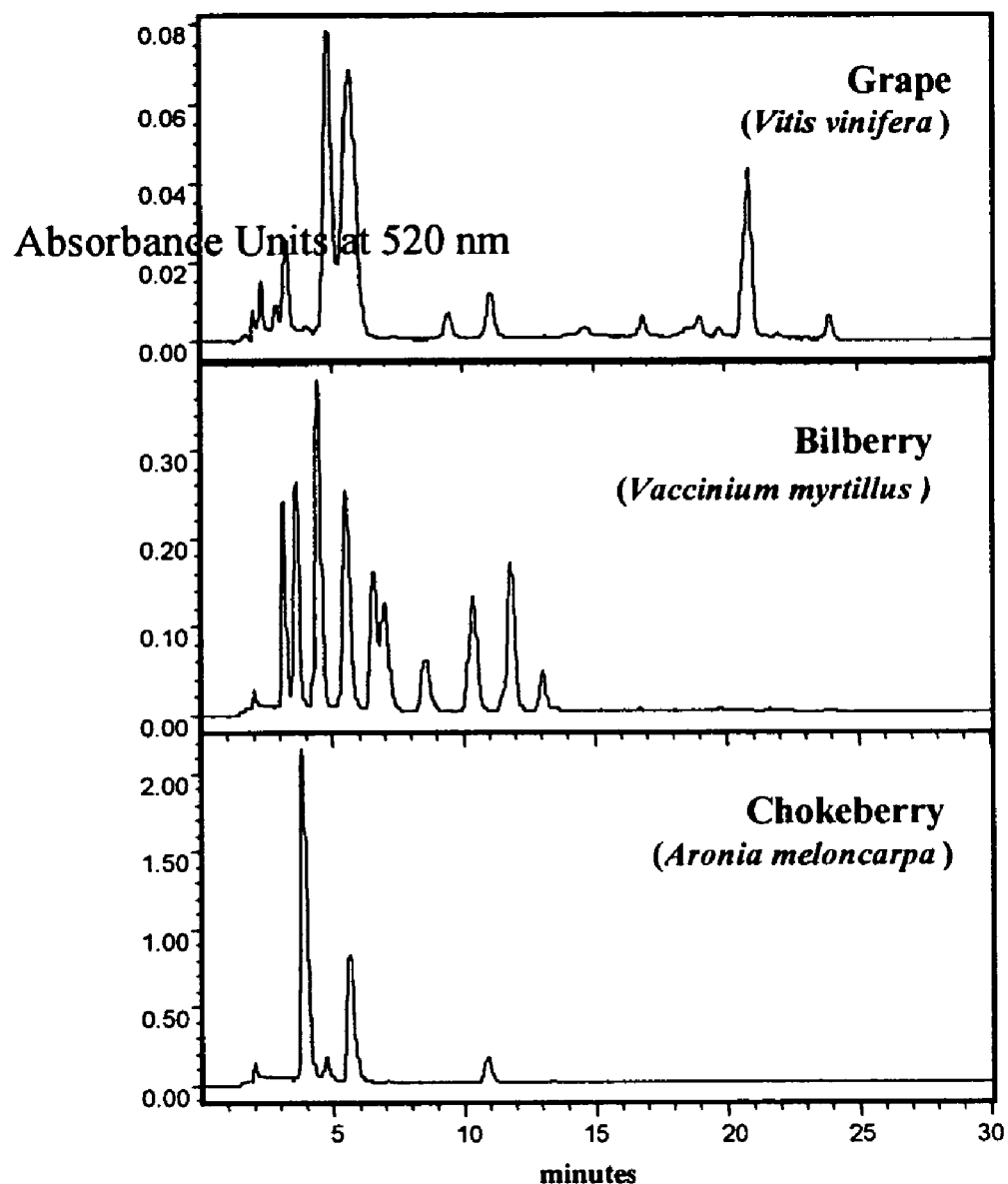
FIG. 9 shows the anthocyanin pigment profile of commercial AREs derived from grape, bilberry, and chokeberry, run under identical HPLC conditions.

Experiments were conducted using three different commercially available anthocyanin rich extracts: grape (Vitis vinifera), chokeberry (Aronia meloncarpa) and bilberry (Vaccinium myrtillus). These extracts were chosen because all of them are marketed as having high antioxidant activity. Also, in selecting the extracts we looked for extracts with contrasting pigment profiles (FIG. 9). Grape and bilberry have both rather complex pigment profiles, with 5 different anthocyanidin groups. The main difference between them is that grapes are glycosylated only with glucose, and have pigments acylated with p-coumaric acid (seen as late eluting peaks in FIG. 9). Bilberries are all non-acylated pigments and show different glycosylations, including galactose, glucose and arabinose. In contrast, chokeberry exhibits a rather simple pigment profile, with two major anthocyanins, both cyanidin derivatives, monoglycolysated with different sugar substitutions: galactose (~65%) and arabinose (~30%).

The biological activity was assessed by determining the level of inhibition of growth of the colon carcinoma cell line, HT-29. This measure of biological activity was chosen for several reasons.

1. First, this cell line is widely used as a simple and rapid in vitro screening method for identifying chemopreventive compounds (Hirsh and others 2000; Miranda and others 1999; Kuntz and others 1999).
2. Second, colon cancer is the second leading cause due to cancer in the US (following lung cancer), so the market for foods inhibiting colon cancer would be substantial (Greenlee and others 2001).
3. Third, unlike cells in other organs, the cells lining the intestine are affected by compounds that are not absorbed due to direct contact, as well as compounds entering the blood.
4. And last, studies described above support the hypothesis that anthocyanins may inhibit colon cancer cell growth.

All anthocyanin-rich extracts inhibited the growth of HT-29 cells (Table 4). HT-29 cells were plated and grown in McCoys media for 24 hours. Semi-purified anthocyanin-rich extracts were added at a concentration of 50 µg monomeric anthocyanin/ml of media and cells were grown for an additional 24, 48 or 72 hrs. The number of viable cells in extract-exposed flasks and control flasks (exposed to vehicle only) were determined using trypan blue exclusion hemocytometry. The percent growth inhibition with the different extracts is presented in Table 4 and was calculated using the following equation:

$$\%\text{Growth inhibition} = \frac{(\#\text{ of cell in control} - \text{number of cells in treated group})}{\#\text{ of cell in control}} \times 100$$

TABLE 4

Percent growth inhibition of HT-29 colon cells by anthocyanin-rich extracts *

| Anthocyanin extract | 24 hr exposure | 48 hr exposure | 72 hr exposure |
|---|---|---|---|
| Chokeberry | 61% | 83% | 96% |
| Bilberry | 43% | 59% | 76% |
| Grape | 27% | 55% | 63% |

* means of duplicate flasks. Similar results for 24 hr exposure were obtained in 3 separate experiments.

One question that arises when compounds are shown to inhibit growth of cancer cells is "what effect will they have on normal cells?" We recently tested the effect of bilberry and chokeberry extracts on the growth of the normal epithelial colon cell line NCM460 (Zhao and others, 2002). Growth of HT-29 cancer cells was significantly inhibited by all doses (25, 50 and 75 ug/ml) of bilberry ARE after 48 hours. In contrast, growth of NCM 460 normal cells was not inhibited until 72 hours, and to a lesser degree (FIG. 10A-B). Similar results were obtained with grape (data not shown) and chokeberry ARE (Example 1). This study supports the hypothesis that anthocyanins may preferably inhibit growth of colon cancer cells. Despite the fact that the extracts were standardized for equal monomeric anthocyanin content, differences were observed in the inhibitory effect of the different extracts (Table 4). All anthocyanin-rich extracts inhibited the growth of HT-29 cells to varying degrees despite the fact that the extracts were standardized for equal monomeric anthocyanin content. Chokeberry, with two major anthocyanins present, was the extract with the simplest pigment profile of all, and also the pigment with the highest observed inhibition (96% in 72 hr) of cancer cell growth. However, bilberry and grape with rather complex pigment profiles, inhibited HT-29 cell growth (up to 76% and 63% inhibition in 72 hr), but not to the same degree as the chokeberry extract.

The dose response was evaluated using chokeberry anthocyanins at concentrations of 50, 100, 150, 200 µg monomeric anthocyanin/ml media (Table 5).

TABLE 5

Effect of chokeberry anthocyanins in the growth of carcinoma cells and distribution of cell cycle.

| Chokeberry anthocyanin concentration | Initial cell count ($10^6$) | Final cell count ($10^6$) | % Inhibition | Cell cycle analyses | | |
|---|---|---|---|---|---|---|
| | | | | G1 | S | G2/M |
| 0 µg/ml (Control) | 1 | 2.79 | 0 | 57.25 | 30.86 | 11.89 |
| 50 µg/ml | 1 | 0.48 | 80 | 29.77 | 54.63 | 15.60 |
| | 1 | 0.61 | | | | |
| 100 µg/ml | 1 | 0.36 | 86 | 29.09 | 53.02 | 17.89 |
| | 1 | 0.42 | | | | |
| 150 µg/ml | 1 | 0.46 | 83 | 32.53 | 52.54 | 14.92 |
| | 1 | 0.49 | | | | |
| 200 µg/ml | 1 | 0.67 | 81 | 29.33 | 56.88 | 13.79 |
| | 1 | 0.36 | | | | |

Cell viability and number were determined by hemocytometry with trypan blue, and cells were fixed for cell cycle analyses. At the levels used, no dose response was observed. It is expected then that lower concentrations of chokeberry anthocyanins may also have an inhibitory effect. Further experiments are proposed to determine the minimum concentration needed to inhibit proliferation of cancerous cells. Considerable differences between control and chokeberry-treated cells were also observed using cell cycle analysis (Table 5) and by assessing cell morphology (data not shown). The cell cycle analyses indicated that chokeberry extract is inhibiting cell growth by stopping cancer cells from completing the DNA synthesis (S-phase). This suggests that the effect of the extract is on a specific target in the cancer cells, and not due to general cell toxicity. Our studies in normal cells support this hypothesis.

The above experiment was conducted to determine if in fact anthocyanins are playing an important role in the inhibition of cancer cell growth. A pure cyanidin-3-galactoside extract was purchased from Polyphenols Inc, and tested on HT-29 carcinoma cells. Visual observations of cell growth and viability suggested that cancerous colonic cell growth was notably inhibited by the pure anthocyanin (see Example 6).

Example 3

Screen Anthocyanin-Rich Extracts for Anticancer Activity Using an In Vitro Biological Model System Commercially available extracts will be used in this first stage. Different anthocyanin-rich sources, with reported antioxidant activity and with different anthocyanin profiles will be screened for their ability to inhibit cell proliferation in a colon cancer cell line. We have previous data indicating that different anthocyanin profiles will exhibit different biological activity (Examples 1 and 2). A total of 6 anthocyanin extracts will be screened to cover different possible main characteristics in pigment profiles (see Table 6 for pigment composition of proposed extracts):

a single aglycone with different sugars substitutions: chokeberry (*Aronia meloncarpa* E.), elderberry (*Sambucus nigra* L.).

different aglycones with different simple sugars substituents: bilberry (*Vaccinium myrtillus* L.)

different aglycone groups, with only glucose as sugar substituent: grape (*Vitis vinifera*)

a single aglycone with high number of substitution, including different sugars and acylating groups, representing acylated food colorants: purple carrot (*Daucus dacota* L), and red radish (*Raphanus sativus*).

TABLE 6

Pigment composition of different anthocyanin-rich commodities

| Source | Type of pigments | Composition |
|---|---|---|
| Chokeberry (*Aronia meloncarpa* E.) | Mono-glycosylated cyanidin derivatives | Cy-3-galactoside Cy-3-arabinoside Cy-3-xyloside Cy-3-glucoside |
| Elderberry (*Sambucus nigra* L.) | Mono- and di-glycosylated cyanidin derivatives | Cy-3-glu Cy-3-sambubioside Cy-3-sam-5-glu Cy-3,5-diglu |
| Bilberry (*Vaccinium myrtillus* L.) | A mixture of 5 different aglycones, mono-glycosylated with galactose, glucose, or arabinose | Dp-3-gal; Dp-3-glu; Dpd-3-ara Cy-3-gal; Cy-3-glu; Cy-3-ara Pt-3-gal; Pt-3-glu; Pt-3-ara Pn-3-gal; Pn-3-glu; Pn-3-ara Mv-3-gal; Mv-3-glu; Mv-3-ara |
| Grape (*Vitis vinifera*) | A mixture of 5 different aglycones, glycosylated with glucose acylated and non acylated with p-coumaric acid | Cy, Dp, Pt, Pn, and Mv-3-glucosides, And their acylated derivatives, with p-coumaric acid |
| Radish (*Raphanus sativus*) | Pg-derivative acylated with one cinnamic acid and an aliphatic acid | Pg-3-soph-5-glu acylated with: P-coumaric acid, Ferulic acid, P-coumaric acid and malonic acid, Ferulic acid and malonic acid |
| Purple carrot (*Daucus carota* L.) | Cy-3-rut-glu-gal acylated with 1 cinnamic acid | Cy-3-gal-xyl (1), Cy-3-gal-xyl-glu Cy-3-gal-xyl-glu + p-coumaric Cy-3-gal-xyl-glu + ferulic Cy-3-gal-xyl-glu + sinapic |

Figure 10:
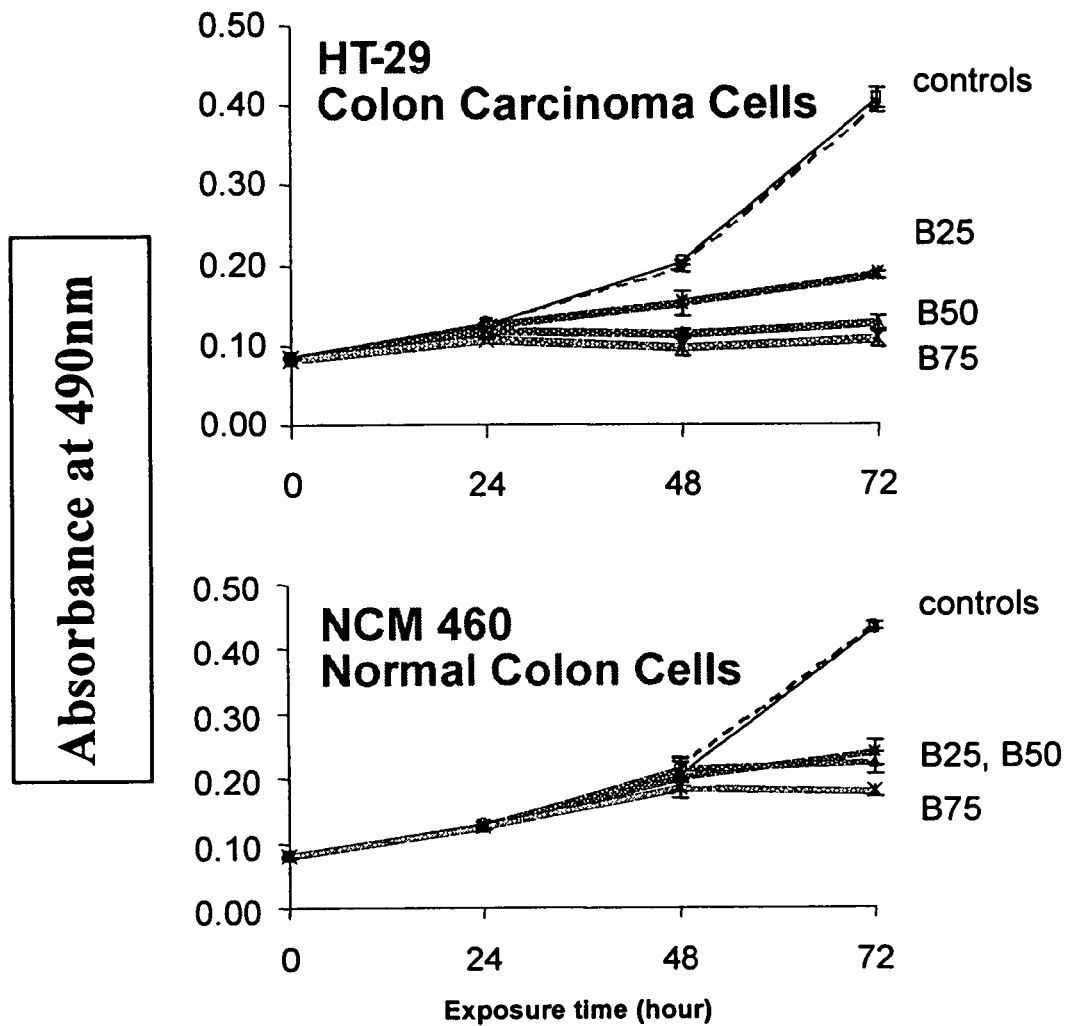
FIG. 10 is a graph showing cell growth over time of HT-29 and NCM cell lines exposed to anthocyanin rich extracts. Controls: no treatment and vehicle only. B25, B50, B75: bilberry at 25 µg/mL, 50 µg/mL and 75 µg/mL respectively.

Anthocyanin extracts will be semi-purified and concentrated using a C-18 resin (for a discussion of Materials and Methods used in this Example, see Example 4, infra). Monomeric anthocyanin content and total phenolics will be quantified in all extracts by using the pH-differential and Folin-Ciocalteu's methods, respectively. Anthocyanin and phenolic profiles will be also monitored by HPLC. Highly concentrated extracts containing 2-3 g monomeric anthocyanin/L will be prepared and tested on HT-29 colon cancer cell at concentration levels ranging from 0 to 100 µg/mL anthocyanin in media. The concentration range was selected based on previous results (Table 4) that showed that at 50 µg/ml anthocyanins in media was enough to achieve close to complete inhibition with chokeberry, while other extracts exhibited only partial inhibition of cancer cell growth at that same dose. Extracts that inhibit cancer cell growth will then be tested using normal colonic cell lines (FIG. 10). Treatments will be done in triplicate and after 24 and 48 hr cell proliferation and viability will be evaluated. A negative control (only media) and a control containing media and acidified water will be used to evaluate our results.

Expected results: We expect to find anthocyanin-rich extracts that inhibit cancer cell proliferation, and cause minimal or no damage to normal cells at doses lower than 50 µg/ml, and we expect that, as suggested by preliminary data, chokeberry will be one of them. Cell count and viability will provide the necessary data to determine anthocyanin concentration required for 50% cancer cell growth inhibition.

Data analysis and interpretation: A reduction in cell count will indicate an inhibition of cell proliferation and increased biological activity. Anthocyanin and phenolic content and profiles of extracts with the greatest cancer cell growth inhibition, and low or no toxicity to normal cells will be used to determine the types of anthocyanin extracts to be evaluated in the following stages of the experiments.

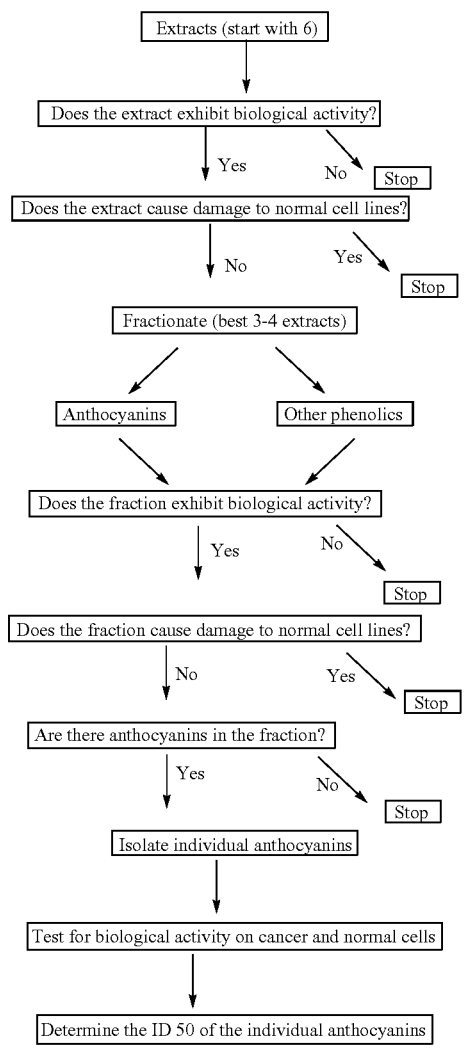

Example 4

Determine the Structure/Function Relationship Between Anthocyanins and Biological Activity The first approach will be to identify 3-4 extracts that exhibited the greatest inhibition of cancer cell proliferation and minimum damage to normal cells as determined in the previous Example 3. Those extracts will be fractionated to be able to determine the compound or group of compounds responsible for the inhibitory effect. First, anthocyanins will be separated from other phenolics using solid phase extraction (C-18 resin) phenolics can be recovered with ethyl acetate while anthocyanins are removed with acidified methanol. Both fractions will be evaluated for biological activity. The fractions will be characterized again by measuring total monomeric anthocyanin content (pH-differential method), polymeric color (by bisulfite bleaching method), total phenolics (Folin Ciocalteu's method) and anthocyanin and phenolic acid profiles (by HPLC). Then we will proceed to isolate the major individual components from the anthocyanin fractions that exhibit biological activity, by using preparative HPLC. The goal is to determine the comparative activity of different components. For that purpose, the ID 50 of the different isolated anthocyanins will be determined.

The second approach will be to screen other commodities with anthocyanin profiles similar to those found to possess promising biological activity. At present we have only 1 or 2 commodities for each pigment profile type. We will screen additional commodities with reported similar anthocyanin profiles to confirm the structure/function relationship. Those commodities will be screened with the same protocol described before and the results compared to results from the previous experiment.

Expected results: Previous experiments demonstrated that different anthocyanin extracts exhibit different levels of biological activity (Table 4), even at equivalent levels of pigment content. We would expect that certain anthocyanin fractions would show higher activity than others, and than many of the phenolic fractions. We also expect to determine what specific chemical structures are more biologically active (lower GI50), and even synergistic effects among compounds. From published literature and preliminary data we anticipate that simple mono-glycoside forms of cyanidin might be highly biologically active. If the biological activity is due to the anthocyanin profile, we would expect that commodities with similar anthocyanin profiles would have comparable biological activity when compared under similar conditions.

Data analyses and interpretation: Statistical analyses will be used to evaluate the data obtained. Percent inhibition, and GI50 of different extracts and individual anthocyanins will be analyzed using PROC Mixed of SAS for Windows 8.1 (SAS Institute Inc. Cary, N.C.). The fixed portion of the model included the effects of the combinations of cell lines, treatments and different time points. Contrasts will be used to test for differences in the response across time for different treatments within and between cell lines. The chemical structure of the anthocyanins that produce the highest % inhibition and the lowest GI50 will be considered as responsible for the biological activity.

Materials and Reagents
Anthocyanin Sources:
Anthocyanin-rich fruit extracts exhibiting different polyphenolic profiles will be obtained from commercial manufacturers: grape extract will be obtained from Polyphenolics, Inc. (Madera, Calif.); the different berry extracts (chokeberry, elderberry and bilberry) will be obtained from Artemis International, Inc. (Fort Wayne, Ind.); and vegetable extracts (purple carrot and radish) will be obtained from RFI Ingredients, Inc. (New York, N.Y.).

Reagents
All HPLC reagents will be purchased from Fisher Scientific (Fisher Scientific, Fair Lawn, N.J.). Standards and reagents for phenolic acid analyses will be purchased from Sigma (Sigma Chemical Co., St. Louis, Mo.).

Cell Lines:
The HT-29 cell line derived from colorectal adenocarcinoma (ATCC; HTB 38) grows as a monolayer in McCoy's 5A medium at 37° C. and 5% $CO_2$ atmosphere. Results will be compared with a normal cell line to determine the potential impact of these compounds/extracts on normal cells. The NCM 460 cell line was derived from a normal human colon by Moyer and others (1996). These cells require highly specialized M3:10™ culture media (InCell Corp. San Antonio, Tex.). These cell lines are already being maintained in Dr. Magnuson's laboratory (see attached letter of intent).

Methods and Procedures
Semi-Purification of Anthocyanin Extracts:
Anthocyanins and other phenolics will be semi-purified by solid phase extraction using a C-18 cartridge (Waters Corp.) as described by Giusti and Wrolstad (1996). Ten grams of powder will be dissolved in 100 mL of 0.01% HCl. Anthocyanins and other phenolics are bound to the cartridge while sugars and other polar compounds are washed away with acidified water. Anthocyanins and other phenolics are then recovered with ethanol containing 0.01% HCl. The alcohol is then removed in a rotary evaporator at 40° C., and the solutes are re-dissolved in 10 ml of 0.01% HCl deionized water.

Fractionation
A crude separation of anthocyanins from other phenolics will be carried out using C-18 Sep-Pak cartridge (Waters Assoc., Milford, Mass.). Anthocyanins (and other phenolics) are adsorbed onto the mini-column. The less polar phenolics are recovered from the mini-column by washing with 2 volumes of ethyl acetate to obtain the non-anthocyanin phenolic fraction. Anthocyanins are subsequently eluted with ethanol containing 0.01% citric acid (v/v) to obtain the anthocyanin extract. The extracts are then concentrated using a Büchi rotovapor at 40° C. and each fraction is then re-dissolved in distilled deionized water containing 0.01% citric acid.

Monomeric Anthocyanin Content:
Monomeric anthocyanin content will be determined by the pH-differential method (Giusti and Wrolstad, 2001) using two different pH buffer solutions, 0.025M potassium chloride buffer (pH 1.0) and 0.4 M sodium acetate buffer (pH 4.5). A Shimadzu 1601 UV spectrophotometer (Shimadzu Scientific Instruments, Inc., Columbia, Md.) and 1 cm path length disposable cells will be used for spectral measurements at 520 and 700 nm. Pigment content will be calculated as cyanidin-3-glucoside, using an extinction coefficient of 26,900 L cm-1mol-1 and molecular weight of 449.2 g mol-1 (Giusti and others 1999).

Color density and Polymeric Color
Polymeric color and color density will be determined by the bisulfite bleaching method (Giusti and Wrolstad, 2001). A Shimadzu 1601 UV spectrophotometer (Shimadzu Scientific Instruments, Inc., Columbia, Md.) and 1 cm path length disposable cells will be used for spectral measurements at 420, 520 and 700 nm (Giusti and others 1999).

HPLC Analysis
Equipment and solvents: The equipment to be used will be a Waters Delta 600 High Pressure Liquid Chromatograph (HPLC), equipped with a Waters 996 photodiode array detector, a Waters 717 plus autosampler and Millenium32 software (Waters Corp., Milford, Mass.). The mobile phase will be composed of A: 1% phosphoric acid, 10% acetic acid, 5% acetonitrile, 84% water and B: 100% acetonitrile. Solvents and samples will be filtered through 0.45 µm PTFE membrane filters (Pall Life Sciences, Ann Arbor, Mich.) and 0.45 µm polypropylene filters (Whatman Inc., Clifton, N.J.)

respectively. Spectral information (from 260 to 600 nm) will be collected over the whole run, and chromatograms extracted at 520, 320 and 280 nm. Spectra and retention times of each peak will be compared to those of authentic known fruit and vegetable samples (Giusti and others 1999).

Analytical work: Anthocyanins and phenolics will be separated using a Symmetry C18 5 μm 4.6×150 mm column (Waters Corp., Milford, Mass.), fitted with a 22×4.6 mm Symmetry™ 2 micro guard column (Waters Corp., Milford, Mass.). The separation is achieved by using a linear gradient from 0 to 35% B in 35 minutes. An injection volume of 50 μl and flow rate of 1 ml/min will be used.

Semi-Preparative HPLC: Individual anthocyanins will be isolated using a Microsorb™ C-18 column (5μ), 250×21.4 mm i.d. fitted with a 50×21.4 mm i.d. guard module (both from Rainin Instrument Co., Inc., Emeryville, Calif.). Separation will be achieved using linear gradients optimized for the specific commodity, so that maximum resolution is achieved in minimum time. The elution of individual anthocyanins to be collected from the semi-preparative HPLC will be monitored by spectral information. Identity and purity of the compounds will be verified by analytical HPLC of isolated compounds.

Total Phenolics

Total phenolics will be measured using a modification of the Folin-Ciocalteau method for total phenols (Singleton and Rossi 1965, Singleton 1988). Different concentrations of gallic acid (40-200 ppm) are used to make the standard curve for total phenol analysis. Two dilutions will be prepared for each sample. The Folin-Ciocalteau reagent and a 20% $Na_2CO_3$ solution are then used to produce a color reaction. Samples with reagents are placed in a thermolyne dri-bath (Barnstead, Dubuque, Iowa) heating block at 40° C. for 20 min and then cooled in an ice bath. The absorbance of the samples and standards will be measured at 755 nm using a Shimadzu UVPC 1601 *Spectrophotometer. Total phenols will be calculated as gallic acid equivalents based on the gallic acid standard curve.*

Pigment/Compound Isolation

Individual pigments or other phenolics of interest will be isolated using semi-preparative HPLC and further purified by passing them through a C-18 Sep-Pak cartridge as previously described. Pigments will be recovered from the cartridge with 90% ethanol and 10% acidified ethanol (0.01% citric acid in ethanol). The ethanol will be evaporated in a Büchi rotovapor at 35° C. and the compounds re-dissolved in sterile deionized water. Purity of isolated compound will be checked using analytical HPLC.

Anthocyanin Extraction

Chemical extraction: Anthocyanin pigments will be extracted from the treated colon cells, after completing the counting and morphological observations. An observation from the preliminary experiments is that cells treated with anthocyanins look darker and reddish in color, even after subsequent washing procedures. We will use acidified methanol (0.1% HCl) to recover anthocyanin pigments from the interior of washed treated cells. The extract obtained will be concentrated by evaporating the methanol and re-dissolving the pigments in 1 ml deionized water. The extract obtained will be analyzed by analytical HPLC as a preliminary look at anthocyanin bioavailability. Also, anthocyanins will be extracted from fruit and vegetable sources selected as providing biologically active extracts, based on results of previous experiments. Samples will be frozen with liquid nitrogen to preserve the integrity of the compounds and to inhibit deterioration. Pigments and other phenolics will be extracted using acetone, and partitioned with chloroform as described by Giusti and Wrolstad (1996).

Aqueous extraction: An additional procedure will be used to extract anthocyanin from fruits and vegetables, using only aqueous solutions and physical means of purification and concentration, to simulate processes used by the juice industry (for fruit and vegetable juice concentrates).

Cell Viability

Cell viability will be assessed using trypan blue exclusion method. Viable cells have an intact cell membrane that excludes the dye. Dead cells take up the dye and are blue when looked under the microscope. Cell morphology assessed using Wright's stain (Sigma Chem.) will also used to assess cell viability.

Cell Proliferation Assays:

Cell proliferation will be assessed using hemocytometry or the CyQUANT Cell Proliferation Assay Kit (Molecular Probes Inc.). The cells will be plated in 24 or 96-well plates (PGE Instruments) for 24 hr before being exposed to different concentrations of the different treatments. For the CyQuant assay the changes in cell proliferation will be read spectrofluorometrically (Carey Eclipse, Varian, Walnut Grove, Calif.) and the cell number in each experiment will be related to the standard curve plotted for the specific cell line. The GI50 value, the concentration that causes 50% growth inhibition will be determined according the National Cancer Institute's protocol for screening chemopreventive agents.

Examples 2-4 References

Akhmadieva, A. K., Zaichkina, S. I., Ruzieva, R. K. and Ganassi, E. E. 1993. Issledovanie zashchitnogo deistviia prirodnogo preparata antotsiana (pelargonidin-3,5-digliukozid). (The protective action of a natural preparation of anthocyan (pelargonidin-3,5-diglucoside). Radiobiologiia, 33(3): 433-435.

Atanasova-Goranova, V. K., Dimova, Pevicharova, G. T. 1997. Effect of food products on endogenous generation of N-nitrosamines in rats. Br. J. Nutr. 78(2): 335-45.

Basa, I. A.; Francis, F. J. 1987. Stability of anthocyanins from sweet potatoes in a model beverage. J. Food Sci. 52: 1753-1754.

Baublis, A., Spomer, A. and Berber-Jimenez, M. D. 1994. Anthocyanin pigments: comparison of extract stability. Journal of Food Science, 59(6): 1219-1221, 1233.

Baublis, A.; Berber-Jimenez, M. 1995. Structural and conformational characterization of a stable anthocyanin from Tradescantia pallida. J. Agric. Food Chem. 43: 640-646.

Bohm H, Boeing, H., Hempel J., Raab, B. and Kroke, A. 1998. Flavonols, flavone and anthocyanins as natural antioxidants of food and their possible role in the prevention of chronic diseases. Z Ernahrungswiss, 37(2): 147-63.

Bomser J, Madhavi, D. L., Singletary, K. and Smith, M. A. 1996. In vitro anticancer activity of fruit extracts from *Vaccinium* species. Planta Med, 62(3): 212-216.

Brouillard, R. 1982. Chemical structure of anthocyanins Food Colors. Anthocyanins as food colors. Pericles Markakis (ed). New York: Academic Press.

Brouillard, R. 1983. The in vivo expression of anthocyanin colour in plants. Phytochemistry, 22 (6): 1311-1323.

Caderni G, De Filippo, C., Luceri, C., Salvadori, M., Giannini, A., Biggeri, A., Remy, S., Cheynier, V. and Dolara, P. 2000. Effects of black tea, green tea and wine extracts on intestinal carcinogenesis induced by azoxymethane in F344 rats. Carcinogenesis, 21(11): 1965-1969.

Caderni, G, Remy, S., Cheynier, V., Morozzi, G and P. Dolara. 1999. Effect of complex polyphenols on colon carcinogenesis. Eur J Nutr, 38(3): 126-132.

Cao, G, Alessio, H M and Cutler, R. G. 1993. Oxygen-radical absorbance capacity assay for antioxidants. Free Radic Biol Med, 14(3): 303-311.

Chen, Y. C., Kuo, T. C., Lin-Shiau, S. Y. and Lin, J. K. 1996. Induction of HSP70 gene expression by modulation of Ca(+2) ion and cellular p53 protein by curcumin in colorectal carcinoma cells. Mol Carcinog, 17(4): 224-34.

Dangles, O., Saito, N. and Brouillard, R. 1993. Anthocyanin intramolecular copigment effect. Phytochemistry, 34(1): 119-124.

Degenhardt, A., Knapp, H. and Winterhalter, P. 2000. Separation and purification of anthocyanins by high-speed countercurrent chromatography and screening for antioxidant activity. J. Agric. Food Chem. 48(2): 338-343.

FMI/Prevention. 2000. Self care needs and whole health solutions. Food Mktg. Inst. Washington D.C.

Francis, F. J. Food colorants: anthocyanins. 1989. Critical reviews in food science and nutrition, 28(4): 273-314.

Giusti, M. M. and R. E. Wrolstad, R. E. 1996. Characterization of red radish anthocyanins. Journal of Food Science, 61(2): 322-326.

Giusti, M. M., Ghanadan, H. and Wrolstad, R. E. 1998. Elucidation of the structure and conformation of red radish (Raphanus sativus) anthocyanins using one- and two-dimensional nuclear magnetic resonance techniques. J. Agric. Food Chem. 46(12): 4858-4863.

Giusti, M. M., Rodriguez-Saona, L. E., and Wrolstad, R. E. 1999. Molar absorptivity and color characteristics of acylated and non-acylated pelargonidin-based anthocyanins. J. Agric. Food Chem. 47(11): 4631-4637.

Goto, T. 1987. Structure, stability and color variation of natural anthocyanins. Fortschritte der Chemie organischer Naturstoffe (Progress in the chemistry of organic natural products), 52: 113-158.

Greenlee, R. T.; Hill-Harmon, M. B.; Murray, T. and Thun, M. 2001. Cancer Statisticas, 2001. CA Cancer J. Clin 51: 15-36.

Hagiwara, A.; Miyashita, K.; Nakanishi, T.; Sano, M.; Tamano, S.; Kadota, T.; Nakamura, M.; Imaida, K.; Ito, N. and Shirai, T. 2001. Pronounced inhibition by a natural anthocyanin, purple corn color, of 2-amino-1-methyl-6-phenylimidazo[4,5-b]pyridine (PhIP)-associated colorectal carcinogenesis in male F344 rats pretreated with 1,2-dimethylhudrazine. Cancer Letters 171: 17-25.

Hanif, R.; Qiao, L.; Shiff, S. J.; and Rigas, B. 1997. Curcumin, a natural plant phenolic food additive, inhibits cell proliferation and induces cell cycle changes in colon adenocarcinoma cell lines by a prostaglandin-independent pathway. J Lab Clin Med, 130(6): 576-584.

Harborne, J. B. 1979. Correlations between flavonoid chemistry, anatomy and geography in the Restionaceae from Australasia and South Africa. Phytochemistry, 18 (8): 1323-1327.

Harborne, J. B. 1986. Nature, distribution and function of plant flavonoids. In Plant flavonoids in biology and medicine. B. Codi, E. Midleton, J. B. Harborne (Eds.). Alan Liss. New York. Pp 15-24.

Heuer, S., Richter, S., Metzger, J. W., Wray, V., Nimtz, M. and Strack, D. 1994. Betacyanins from bracts of Bougainvillea glabra. Phytochemistry, 37(3): 761-767.

Hesler, M. A.; Hotchkiss, J. H. and Roe, D. A. 1992. Influence of fruit and vegetable juices on the endogenous formation of N-nitrosoproline and N-nitrosothiazolidine-4-carboxylic acid in humans on controlled diets. Carcinogenesis, 13: 2277-2280.

Hirsch K., Danilenko M., Giat J., Miron T., Rabinkov A., Wilchek M., Mirelman D., Levy, J., Sharoni Y. 2000. Effect of purified allicin, the major ingredient of freshly crushed garlic, on cancer cell proliferation. Nutr. Cancer 38(2): 245-54.

Hollman, P. C. H., and Katan, M. B. 1997. Absorption, metabolism and health effects of dietary flavonoids in man. Biomedicine and Pharmacotherapy, 51 (8): 305-310.

Hollman, P. C. H., and Katan, M. B. 1999. Health effects and bioavailability of dietary flavonols. Free Radical Research, 31 (SUPPL.):S75-580.

Hong, V.; Wrolstad, R. E. 1990. Use of HPLC separation/photodiode array detection for characterization of anthocyanins. J. Agric. Food Chem. 38: 708-715.

Jackman R. L.; Smith J. L. 1996. Anthocyanins and Betalains. Ch. 8 In Natural Food Colorants. Eds. G. A. F. Hendry and J. D. Houghton. 2nd Ed. Blackie A&P Great Britain.

Kamei, H.; Kojima, T.; Hasegawa, M.; Koide, T.; Umeda, T.; Yukawa, T. and Terabe, K. 1995. Suppression of tumor cell growth by anthocyanins in vitro. Cancer Invest, 13(6): 590-594.

Karaivanova M., Drenska D., and Ovcharov R. 1990. Modifitsirane na toksichnite efekti na platinovi kompleksi s antotsiani (A modification of the toxic effects of platinum complexes with antocyans). Eksp Med Morfol, 29(2): 19-24.

Koide, T., Hashimoto, Y., Kamei, H., Kojima, T., Hasegawa, M. and Terabe, K. 1997. Antitumor effect of anthocyanin fractions extracted from red soybeans and red beans in vitro and in vivo. Cancer Biother Radiopharm, 12(4): 277-280.

Koide, T., Kamei, H., Hashimoto, Y., Kojima, T. and Hasegawa, M. 1996. Antitumor effect of hydrolyzed anthocyanin from grape rinds and red rice. Cancer Biother Radiopharm, 11(4): 273-7.

Kramer-Schafhalter, A.; Fuchs, H.; Silhar, S. S.; Kovac, M. and Pfannhauser, W. 1996. Process consideration for extraction from black chokeberry. In The 2" Int. Symposium on natural colorants INF/COL II. The Hereld organization. Acapulco, Mexico.

Kresty, L. A.; Morse, M. A.; Adams, C. A., Lu, J. and Stoner, G. D. 1998. Inhibitory effect of lyophilized black raspberries on esophageal tumorigenesis and $O^6$-methylguanine levels in F344 rat. Proc. Annu. Meet. Am. Assoc. Cancer Res. 39, A120.

Kuhnau, J. 1976. The Flavonoids. A class of semi-essential food components: Their role in human nutrition. World Rev. Nutr. Dietet. 24:117-191.

Kuntz, S., Wenzel, U., and Daniel, H.1999. Comparative analysis of the effects of flavonoids on proliferation, cytotoxicity, and apoptosis in human colon cancer cell lines. Eur J Nutr 38(3): 133-42.

Lietti, A.; Cristoni, A. and Picci, M. 1976. Studies on Vaccinium myrtillus anthocyanosides. I. Vasoprotective and anti-inflamatory activity. Arzeim-Forsch. 26(5): 829-832.

Lu, T. S., Saito, N., Yokoi, M., Shigihara, A. and Honda, T. 1992. Acylated pelargonidin glycosides in the red-purple flowers of Pharbitis nil. Phytochemistry, 31(1): 289-295.

Lu, T. S., Saito, N., Yokoi, M., Shigihara, A. and Honda, T. 1992. Acylated peonidin glycosides in the violet-blue cultivars of Pharbitis nil. Phytochemistry. 31(2): 659-663.

Mazza, G. and Miniati, E. 1993. Anthocyanins in fruits, vegetables, and grains. Boca Raton: CRC Press.

Messina, M. J., Loprinzi, C. L. 2001. Soy for brest cancer survivors: a critical review of the literature. Am. Inst. Cancer Res. 11$^{th}$Annual Res. Conf. Diet Nutr. Cancer.

Miyazawa, T., Nakagawa, K., Kudo, M., Muraishi, K., and Someya, K. 1999. Direct intestinal absorption of red fruit anthocyanins, cyanidin-3-glucoside and cyanidin-3,5-diglucoside, into rats and humans. J. Agric. Food Chem. 47(3): 1083-1091.

Morazzoni, P. and Magistretti, M. J. 1986. Effects of *Vaccinium myrtillus* anthocyanosides on prostacyclin-like activity in rat arterial tissue. Fitoterapia, 57(1): 11-14.

Moyer, M. P.; Manzano, R. L. Merriman, R. L., Stauffer, J. S, and Tanzer, L. R. 1996. NCM 460 a normal human colon mucosal epithelial cell line. In Vitro Cell. Devel. Biol.: Animal 32: 315-317.

Odake, K., Terahara, N., Saito, N., Toki, K., and Honda, T. 1992. Chemical structures of two anthocyanins from purple sweet potato, *Ipomoea* batatas. Phytochemistry, 31(6): 2127-2130.

Prior, R. L., Cao, G., Martin, A., Sofic, E., McEwen, J., O'Brien, C., Lischner, N., Ehlenfeldt, M., Kalt, W., Krewer, G. and Mainland, C. M. 1998. Antioxidant capacity as influenced by total phenolic and anthocyanin content, maturity, and variety of *Vaccinium* species. J. Agric. Food Chem. 46(7): 2686-2693.

Rice-Evans, C. A., and Miller, N. J. 1996. Antioxidant activities of flavonoids as bioactive components of food. Transactions, 24(3): 790-795.

Rodriguez-Saona, L. E., Giusti, M. M., and Wrolstad, R. E. 1998. Anthocyanin pigment composition of red-fleshed potatoes. J. Food Sci. 63: 458-465.

Rodriguez-Saona, L. E., Giusti, M. M., and Wrolstad, R. E. 1999. Color and pigment stability of red radish and red-fleshed potato anthocyanins in juice model systems. J. Food Sci. 64: 451-456.

Rommel, A.; Wrolstad, R. E.; Heatherbell, D. A. 1992. Blackberry juice and wine: processing and storage effects on anthocyanin composition, color and appearance. J. Food Sci. 57: 385-391, 410.

Shi, Z., Bassa, I. A., Gabriel, S. L. and Francis, F. J. 1992. Anthocyanin pigments of sweet potatoes—*Ipomoea* batatas. Journal of Food Science, 57(2): 755-757, 770.

Stoner, G. D. and Morse, M. A. 1997. Inhibitory effect of strawberries on esophageal tumorigenesis and 0$^6$-methylguanine levels in F344 rat. Proc. Annu. Meet. Am. Assoc. Cancer Res. 38, A2462.

Strack, D.; Wray, V. The anthocyanins. In The Flavonoids: Advances in Research Since 1986. Ed. J. B. Harborne. Chapman and Hall. 1994.

Tamura, H. and Yamagami, A. 1994. Antioxidative activity of monoacylated anthocyanins isolated from Muscat Bailey A grape. J. Agric. Food Chem. 42(8): 1612-1615.

Tessitore, L.; Davit, A.; Sarotto, I.; and Caderni, G. 2000. Resveratrol depresses the growth of colorectal aberrant crypt foci by affecting bax and p21(CIP) expression. Carcinogenesis, 21(8): 1619-22.

Timberlake, C F.; Henry, B. S. 1988. Anthocyanins as natural food colorants. Prog. Clin. Biol. Res. 280: 107-121.

Timberlake, C. F. 1988. The biological properties of anthocyanin compounds. NATCOL 1988. Quarterly Bulletin.

USDA. 2000. Commodity reports. US Department of Agriculture.

Verma, S. P., Goldin, B. R., and Lin, P. S. 1998. The inhibition of the estrogenic effects of pesticides and environmental chemicals by curcumin and isoflavonoids. Environ Health Perspect, 106(12): 807-12.

Wang, H., Cao, G. and Prior, R. L. 1997. Oxygen radical absorbing capacity of anthocyanins. Journal of Agricultural and Food Chemistry, 45(2): 304-309.

Xue, H., Aziz, R. M., Sun, N., Cassady, J. M., Kamendulis, L. M., Xu, Y., Stoner, G. D. and Klaunig, J. E. 2001. Inhibition of cellular transformation by berry extracts. Carcinogenesis, 22(2): 351-356.

Yoshimoto, M.; Okuno, S.; Yamaguchi, M. and Yamakawa, O. 2001. Antimutagenecity of deacylated anthocyanins in purple-fleshed sweet potatoes. Biosci. Biotechnol. Biochem. 65(7): 1652-1655.

Zhao, C.; Malik, M.; Magnuson, B. A.; Giusti, M. M. 2002. The inhibitory effect of different anthocyanin-rich extracts on cancer cell growth. Presented at the Ann. Mtg., Inst. Food Technol., Anaheim, Calif., June 15-19.

Example 5

Anthocyanin-Rich Extracts Inhibit Azoxymethane-Induced Colon Aberrant Crypt Foci in Rats The aim of the present study was to investigate the effects of anthocyanin-rich extracts (AREs) from bilberry (*Vaccinium myrtillus* L.), chokeberry (*Aronia meloncarpa* E.) and grape (*Vitis vinfera*) on development of aberrant crypt foci (ACF) in male rats treated with colon carcinogen, azoxymethane (AOM). Fischer 344 male rats were fed with AIN-93 diet (control) and AIN-93 diet supplemented with AREs for 14 weeks. The rats were injected with 20 mg/kg body weight of azoxymethane in the second week of the study. After 14 weeks, colons were scored for number and multiplicity of ACF. The total ACF were significantly reduced ($p<0.05$) in bilberry, chokeberry and grape ARE fed rats as compared to the control group. The number of large ACFs ($\geq 5$ multiplicity) was reduced significantly in bilberry and chokeberry ARE fed rats. To measure in-vivo oxidative damage in all groups, competitive ELISA was used to measure urinary 8-hydroxyguanosine. No significant difference was observed within rats fed different diets. Significant decrease in cellular proliferation was observed in colon crypts of rats on bilberry and chokeberry diets with the greatest degree of inhibition in the bottom third of the crypts. To understand molecular mechanism of action, expression of cyclooxygenase genes was studied. A significant difference in the expression of cyclooxygenase-2 gene in rats fed diets with bilberry and grape ARE was observed. The results indicate a protective role of the AREs in colon carcinogensis ACF are putative preneoplastic lesions widely used as biomarker for colon cancer, which may develop into colorectal tumors. ACF do not occur in untreated rats but appear in colon and rectum within few weeks during post initiation phase after treatment with carcinogens such as AOM.

Proliferating cell nuclear antigen (PCNA) immunohistochemistry was done to measure cell proliferation. Changes in expression of cyclooxygenase (COX-1 and COX-2) genes were also evaluated. COX-1 maintains normal gastric mucosa and influences kidney function. The inhibition of COX-1 gene expression is therefore undesirable whereas blocking of induced COX-2 gene expression in animal studies have shown to decrease colon cancer development therefore this is considered potential target for therapeutics.

Materials and Methods

Test compound and other chemicals—Commercially available anthocyanin-rich extracts of bilberry (Vaccinum myrtillus L.) and chokeberry (*Aronia meloncarpa* E.) were supplied by Artemis International, Inc. (Fort Wayne, Ind.). Grape *Vitis vinfera*) extract was supplied by Polyphenolics, Inc. (Madera, Calif.). AOM, (lot no. 111k1502) was obtained from Sigma Chemical (St. Louis, Mo.).

Analysis and preparation of diets-Diets containing 4 g/kg monomeric anthocyanin from chokeberry, bilberry or grape ARE were prepared by supplementing AIN-93 powdered diet (Dyets Inc., PA). All the three anthocyanin extracts were added in on the basis of their monomeric anthocyanin content. They were added at the expense of cornstarch. The composition of experimental diet is summarized in Table 7. All diets were prepared fresh on a weekly basis and stored at 4° C. until use.

TABLE 7

| Ingredient gm/kg | AIN-93 | AIN-93 with 5% Chokeberry ARE | AIN-93 with 3.5% Bilberry ARE | AIN-93 with 2.6% Grape ARE |
|---|---|---|---|---|
| Casein | 200 | 200 | 200 | 200 |
| L-Cystine | 3.0 | 3.0 | 3.0 | 3.0 |
| Sucrose | 100 | 100 | 100 | 100 |
| Corn starch | 397.486 | 347.486 | 362.486 | 370.986 |
| Soyabean oil | 70 | 70 | 70 | 70 |
| Fiber (cellulose) | 50 | 50 | 50 | 50 |
| Mineral Mix | 35 | 35 | 35 | 35 |
| Vitamin mix | 10 | 10 | 10 | 10 |
| Choline bitartrate | 2.5 | 2.5 | 2.5 | 2.5 |
| AREs | — | 50 | 35 | 26 |

Monomeric anthocyanin content and total phenolics measurement—The monomeric anthocyanin content of all three extracts was determined by pH-differential method. A Shimadzu 1601 UV spectrophotometer (Shimadzu Scientific Instruments, Inc. Columbia, Md.) and 1 cm path length disposable cuvettes were used for spectral measurements at 520 and 700 nm. Pigment content calculation was done as cyanidin-3-glucoside, using extinction coefficient ($\epsilon$) of 26900 L cm$^{-1}$ mol$^{-1}$ and molecular weight (MW) of 449.2 g mol$^{-1}$.

Total phenolics were measured using a modification of the Folin-Ciacalteau method for total phenols as described by Singleton. V. L. (1988) *Modern Methods of Plant Analysis*, Berlin, Heidelberg, Spring Verlag. The absorbance of the samples and standards was measured at 755 nm. Total phenols were calculated as gallic acid equivalents based on a gallic acid standard curve.

Oxygen Radical Absorbance Capacity (ORAC) values—The ORAC values for AREs was measured based on a procedure described by Prior et al. (2003) *J. Agric. Food Chem.* 51:3273-3279.

Animals, treatment and housing—Forty 3-4 week old male specific pathogen free F 344 (maintain standard form throughout the paper) rats were obtained from Harlan (Indianapolis Ind.). In the first week of acclimatization rats were slowly weaned from pelleted rat chow to powdered AlN-93 diets. Chewing bones (Bio-Serv, NJ) were also provided for overgrowing teeth due to feeding of powdered diet for long time. Rats were randomly allocated in four groups of ten animals each. The animals were housed in pairs in suspended stainless steel cages with wire mesh floor and front. Powdered diet was provided in standard feeding cups. Diet and tap water was available ad libitum. Artificial light was supplied from fluorescent tubes, in a 12 h light-12 h dark cycles. The number of air changes were ~10 per hour. Relative humidity was maintained at 25%-60%. Clinical signs for all the animals were recorded regularly.

Carcinogen injection—All animals randomly received one dose of a subcutaneous injection of AOM in saline at 20 mg/kg sc.

Body weight and food consumption—Body weight was recorded twice in a week and 3-days food intake was measured two times for all the animals in 14 the week study.

Tissue Collection

Fourteen weeks after the start of experimental diets, the animals were sacrificed by carbon dioxide asphyxiation. Colon was flushed with ice-cold saline to remove fecal material. The proximal 4 cm was immersed and fixed in RNAlater (Ambion Inc.) for RNA isolation. The remaining colon was slit open and fixed flat on balsa wood (with mucosal side up). Colon tissue was preserved in 10% buffered formalin for evaluation of ACF and cell proliferation. Caecal, Liver etc. . . . were weighed and immediately frozen in liquid nitrogen and stored at −80° C.

Aberrant crypt foci (ACF)—ACF were evaluated by previously described method of (Magnuson et al. 1998, American Chemical Society, 231-243). ACF were made visible by staining the colons with 0.1% methylene blue in saline. ACF were identified using light microscope at 40× magnifications. Aberrant crypts have large usually elongated openings. The lining epithelial cells in ACF are larger and are more intensely stained with methylene blue than surrounding normal epithelial cells. The number of aberrant crypts in each focus was also noted to determine multiplicity.

Immunohistochemical staining of PCNA—Cell proliferation was measured using Proliferating Cell Nuclear Antigen (PCNA) immunohistochemistry. PCNA is used as a reliable marker of epithelial colonic cell. Only complete crypts sectioned longitudinally from top to bottom with full length of the crypt and muscularis mucosa at the base visible were scored. The total number of epithelial cells in each crypt column (side) was defined as crypt height. Darkly stained cell divided by crypt height was the labeling index. Twenty values were obtained (10 crypts of 2 crypts column each). The mean of these 20 values for each rat was then used in subsequent statistical analysis. Measurement of urinary 8-OHdG-Urinary 8-OHdG is widely used as a biomarker for oxidative damage of DNA. 8-OHdG reflects DNA mutation potential and therefore recently it has attracted attention as a marker of carcinogenic risk. To compare antioxidant potential of three AREs measurement of urinary 8-OHdG was done by ELISA (Genox Corporation, MD). ELISA method is considered more sensitive and generally provides higher level than other methods. Urine collection was standardized by analysis of creatinine {KIT} concentrations. Analysis was performed using a creatinine colorometric microplate assay (Oxford, Mich.).

Analysis of Cyclooxygenase-1 and 2 expression—Changes in expression of cyclooxygenase genes was analyzed as described earlier in Example 1. In brief, total cellular RNA was extracted from colonic mucosa lining using Trizol reagent (Invitrogen, CA). Human COX-1 and COX-2 gene-specific Relative RT-PCR Kits (Ambion, Inc.) were used with ribosomal gene 18S (498 bp) as an internal control. The following thermocycling conditions were used for PCR assays: one 2-min cycle at 92° C. followed by 26 cycles of denaturation for 30 s at 92° C., annealing for 30 s at 59° C. (COX-1) or 30 s at 60° C. (COX-2), and extension for 1 min at 72° C. The final extension was given for 5 min at 72° C. The PCR products from multiplex reactions were analyzed using DNA 7500 LabChip® and Agilent 2100 bioanalyzer according to the manufacturer's protocol. The changes in the gene expression were represented by the changing ratio between the area of bands representing gene of interest and the band representing 18S gene. A ratio difference in the control versus the treated cells is the measure of change in gene expression.

Results

Figure 11:
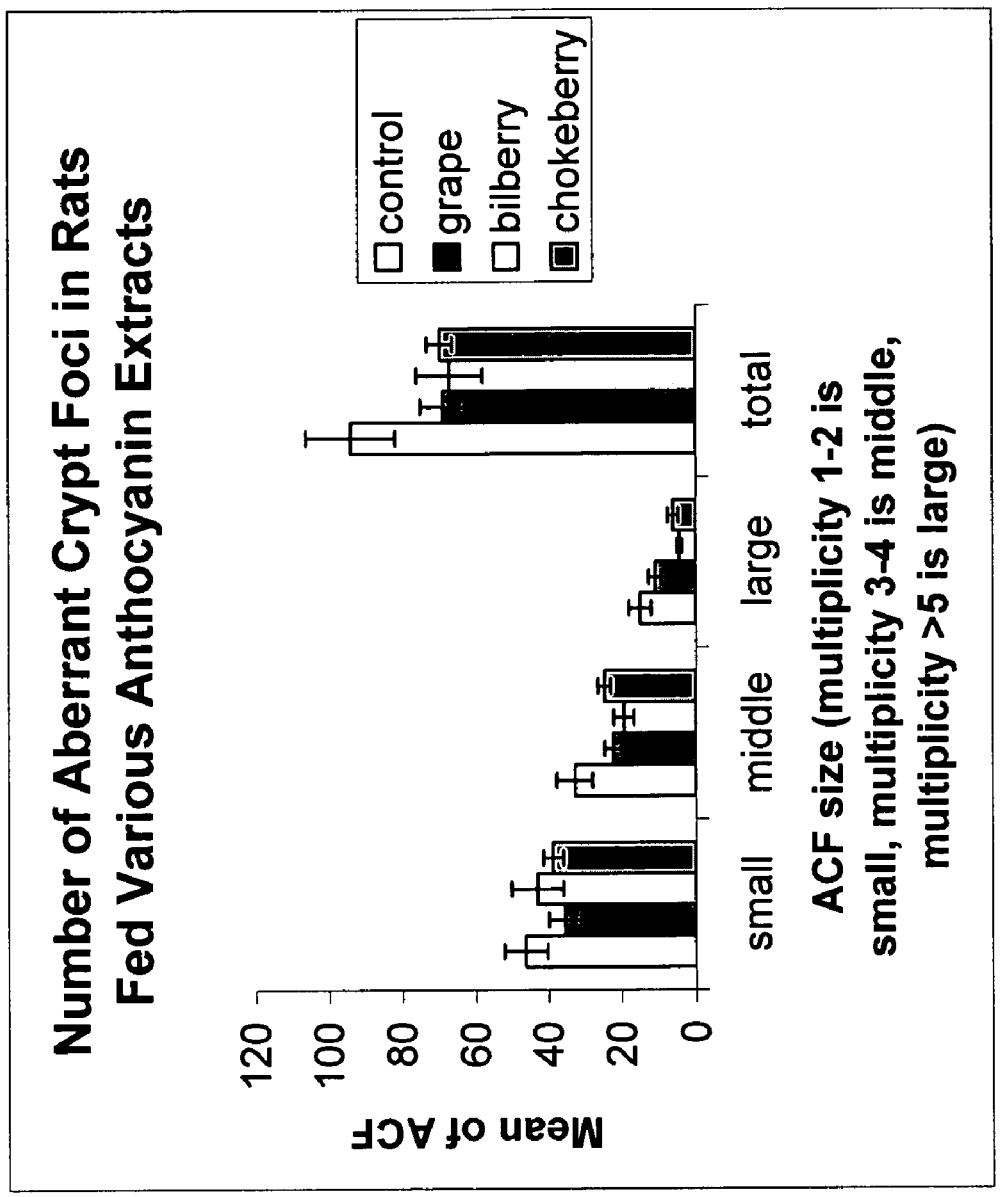
FIG. 11 is a graph showing aberrant crypt foci development in rats fed either a control diet or a diet containing ARE.
Figure 12:
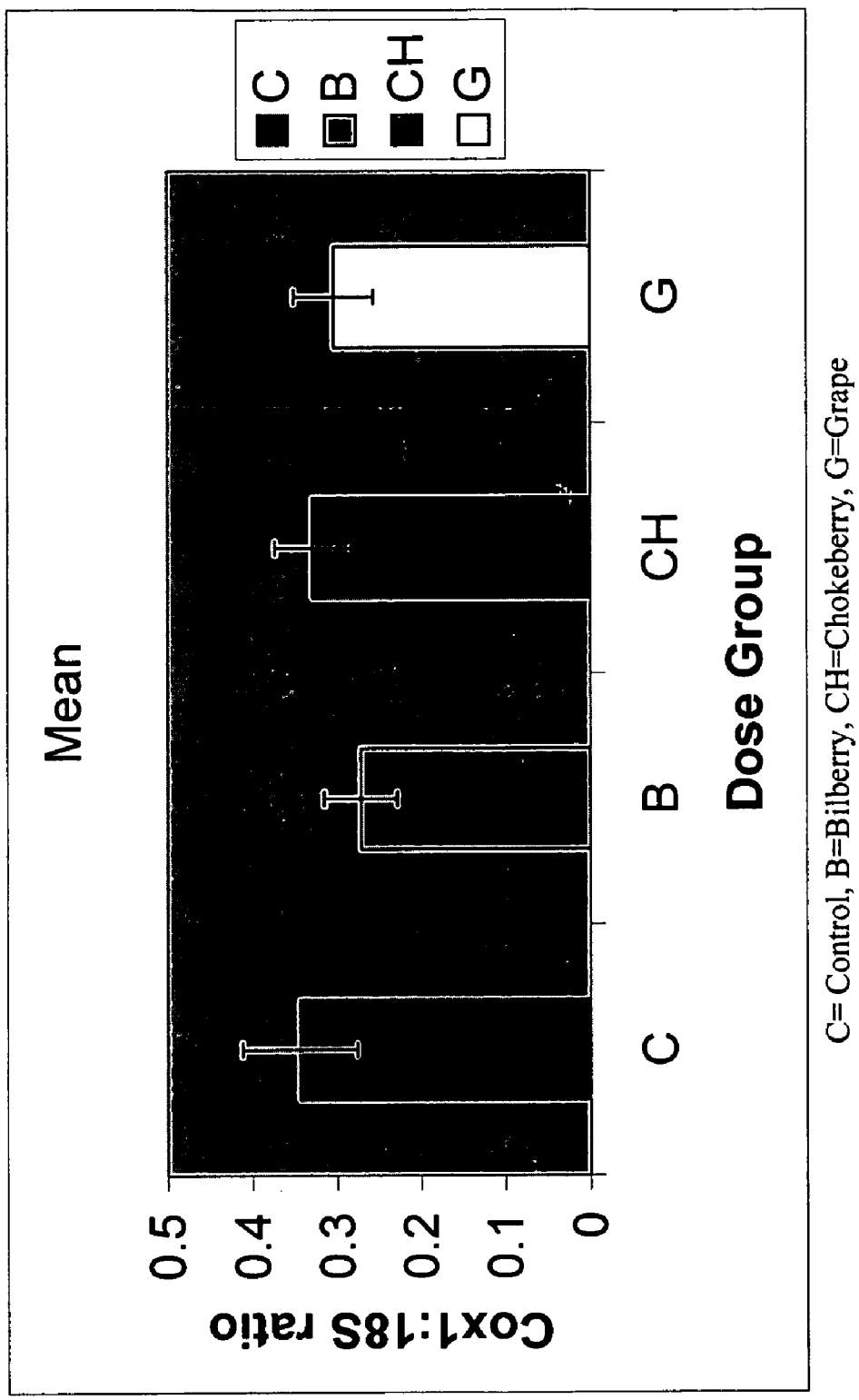
FIG. 12 is a graph showing the expression of cyclooxygenase-2 (Cox-2) gene expression in the colonic mucosa of rats fed either a control or an ARE diet.
Figure 13:
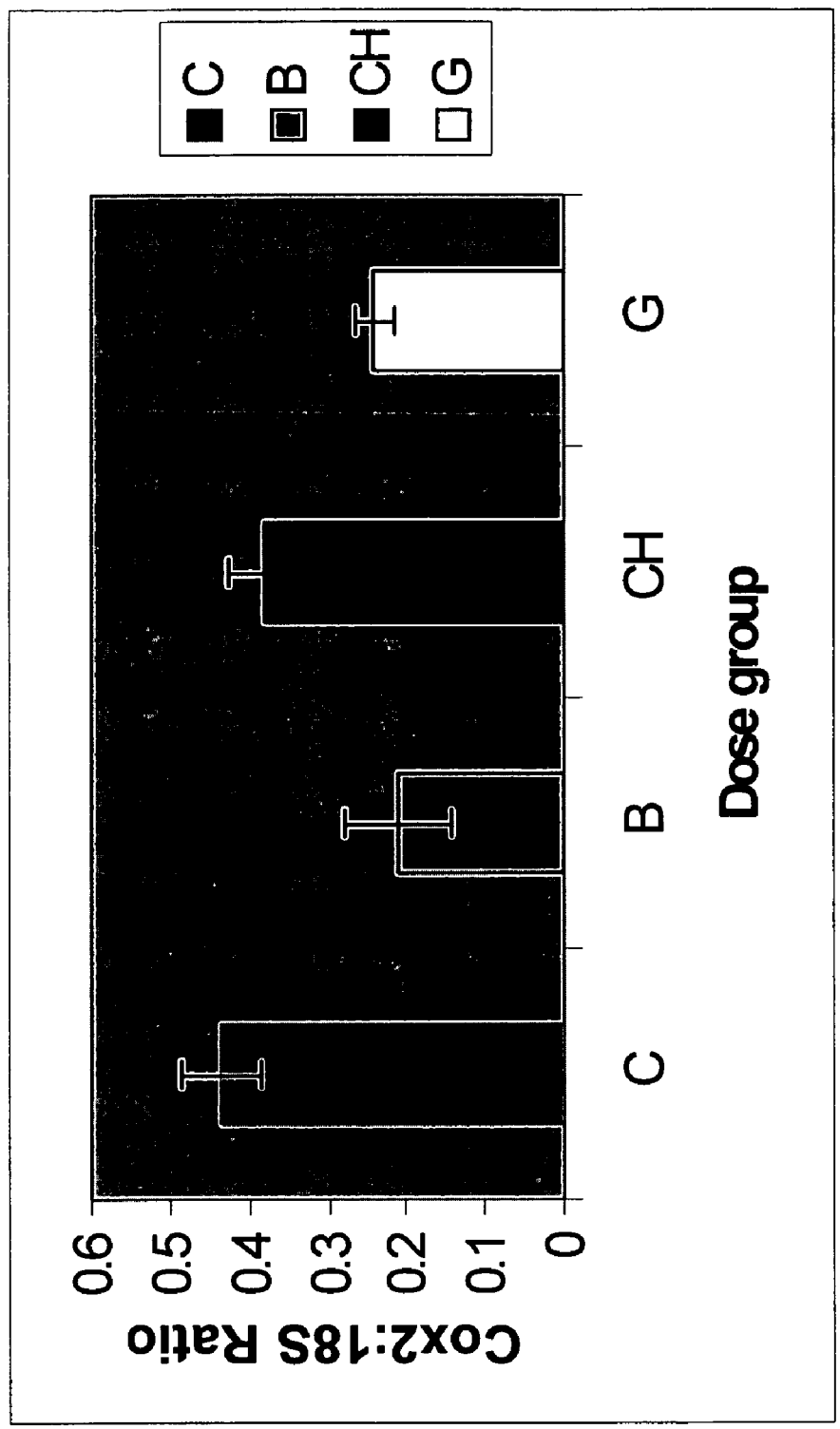
FIG. 13 is a graph showing the expression of cyclooxygenase-1 (Cox-1) gene in the colonic mucosa of rats fed either control or an ARE diet.

Body weight and food consumption—There were no significant (p>0.05) differences among AREs and control groups in either weight gain or feed intake (Table 7).
Aberrant crypt foci-Total number of ACF in the control diet group was significantly higher than the total number of ACF in all anthocyanin-fed groups (p<0.05). Also large size ACF (≧5 multiplicity) were significantly reduced in both bilberry- and chokeberry-fed rats as compared to rats fed the control diet (p=0.0003 and 0.0020) Bilberry fed rats also had significant fewer large size ACF than rats fed with the grape (p=0.02). There are no significant difference (p>0.05) in small ACF among the different group (FIG. 11).
Cellular proliferation—Colonic cellular proliferation was significantly decreased in rats fed the bilberry (P=0.008) and chokeberry (P=0.015) diets compared to rats fed with control diet. The greatest degree of inhibition was occurring in the bottom third of the crypts (data not shown).
Urinary 8-OHdG determination—There was no significant difference in urinary 8-OHdG levels among the groups. Adjusting for creatinine levels also resulted in no significant difference in any of the groups.
Cox-1 and Cox-2 gene expression—No significant difference was observed in the expression of COX-1 gene (FIG. 13) in the colonic mucosa of the rats fed the ARE diet as compared to rats fed the control diet. The COX-2 gene expression (FIG. 12) was significantly down regulated in colonic mucosa of rats fed the bilberry and grape ARE diets (p=0.0086). The chokeberry ARE fed rats did not show a significant change in COX-2 gene expression as compared to rats fed the control diet.

Discussion

These results demonstrate that anthocyanin rich extracts of bilberry, chokeberry and grape reduced the total number of early lesions of colon cancer called aberrant crypt foci (ACF) induced in rat colon by AOM. The number of large ACF, which are most predictive of tumor outcome, was also significantly reduced in rats fed with bilberry and chokeberry diets. These in vivo results demonstrating chemopreventive activity of bilberry and chokeberry ARE in development of preneoplastic lesions of colorectal tumors agree with our previous reports that commercially available ARE from chokeberry and bilberry can inhibit growth of colon cancer cells without affecting growth of normal colonic cells in vitro.
We investigated several potential mechanisms for the observed chemopreventive activity in vivo, based on our previous in vitro reports and the reports of others. As we observed in vitro, the addition of AREs to the diets of rats resulted in inhibition of cell proliferation. Rats fed bilberry and grape, but not chokeberry, diets had down regulated gene expression of COX-2 but not COX-1. These results are in agreement with the in-vitro experiment described in Example 1 (see also, Malik et al., 2003, *Nutr & Cancer*, 46(2):186-196) that the growth inhibition of HT-29 cells by the chokeberry anthocyanin-rich extract does not involve suppression of COX-2 activity. They are in contrast to Seeram et al (2001) *Phytomedicine*, 8(5)362-369 who reported inhibition of both COX-1 and -2 purified enzymes by anthocyanins in vitro. Although Harris and colleagues (Harris et al. (2001) *Nutr. Cance,r* 40(2):125-133) observed significant reduction in urinary 8-OHdG levels in rats fed freeze-fried black raspberries and treated with AOM, we did not observe a similar effect. This is in agreement with reported results of Pool-Zobel et al. (1999) *Eur. J. Nutr.*, 38(5):227-234 that intracellular oxidative stress is weakly effected by anthocyanins/anthocyandins found in *Aronia melanocarpa* elliot concentrates (elderberry, macqui and tintorera fruits concentrates).

Example 6

Figure 14A:
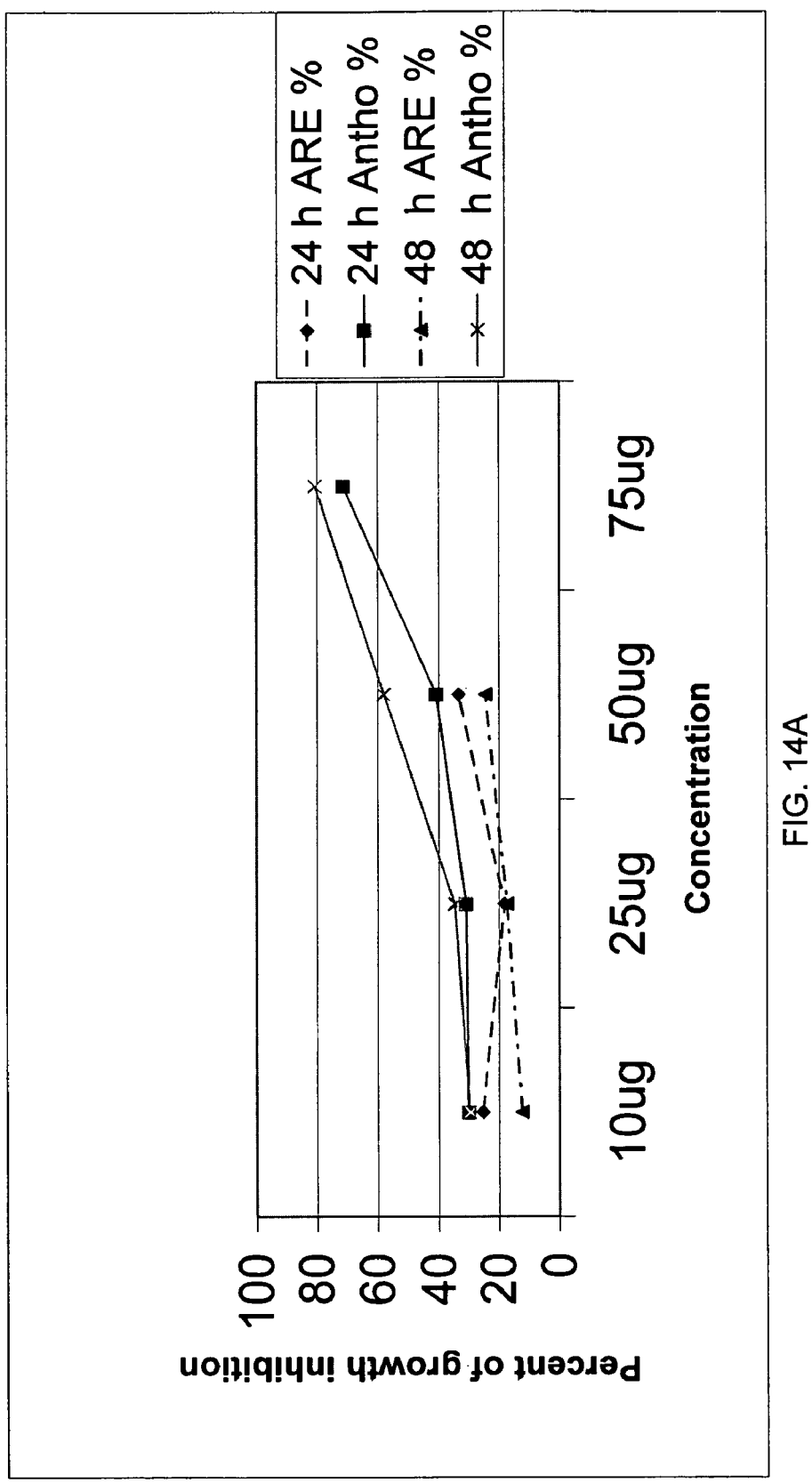
FIGS. 14A-C shows the percentage of growth inhibition of HT 29 colonic cancer cells treated with various ARE fractions.
Figure 14B:
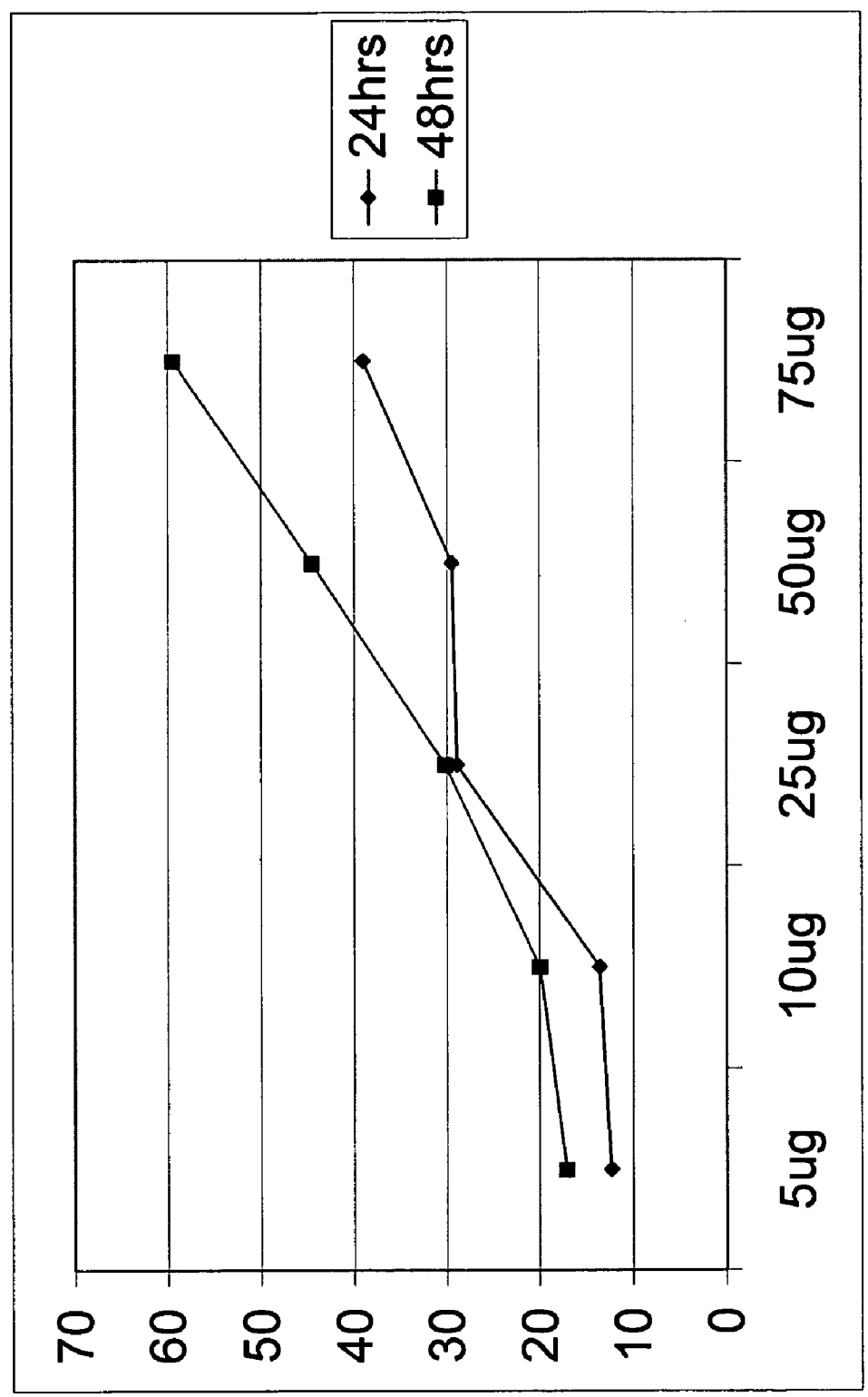
Figure 14C:
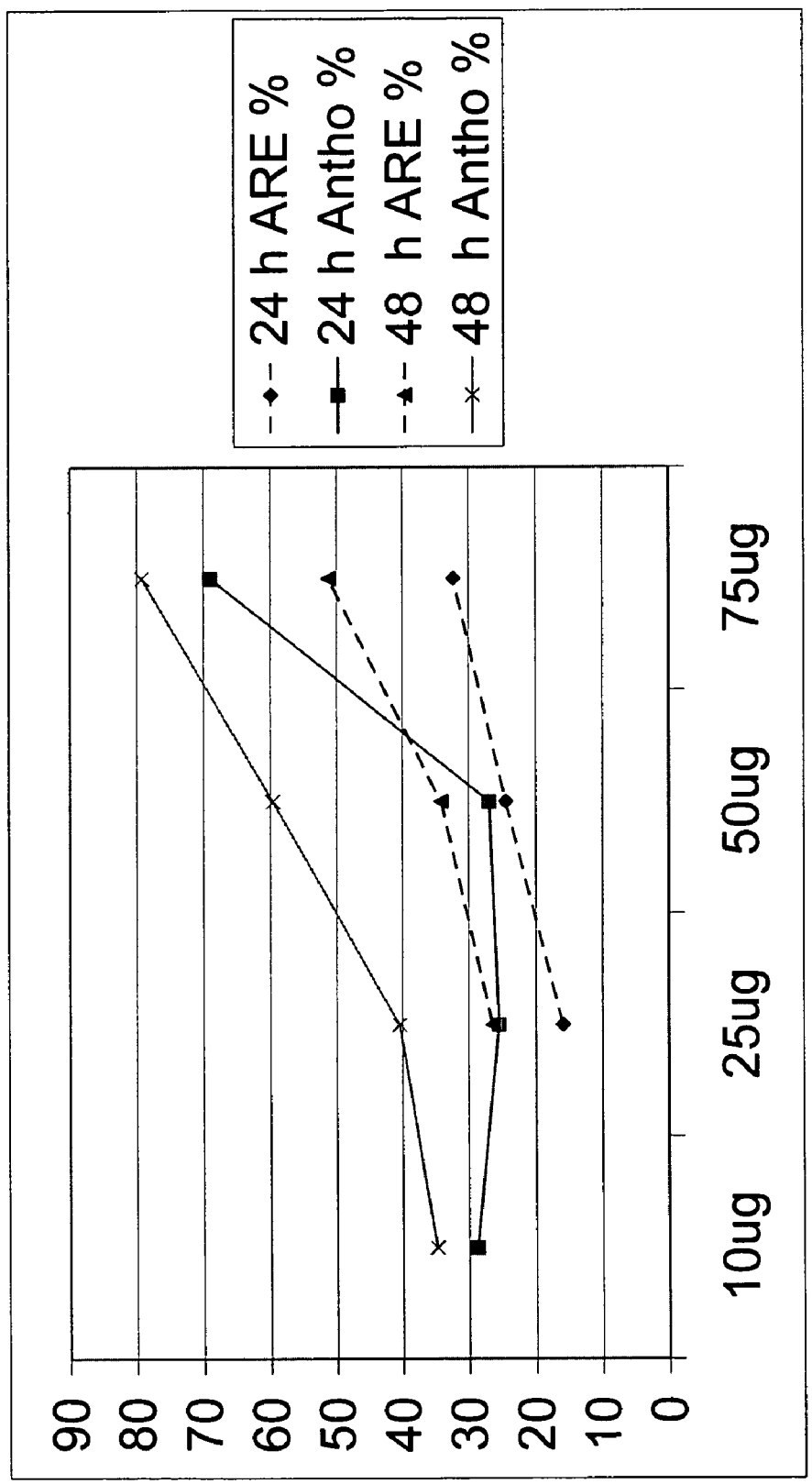

Growth Inhibition of Colon Cancer Cells by Various ARE Fractions of Chokeberry and Bilberry Extracts This aims of this experiment were: (1) To confirm that the anthocyanins are significantly contributing to the anticarcinogenic effect of the ARE and (2) to assess the effect of the aglcyon of the anthocyanins on growth inhibition. To do this, we first purified the anthocyanin fraction from the chokeberry and bilberry AREs, to remove all other phenolics. Secondly, we treated the purfied chokeberry anthocyanins with acid to generate chokeberry aglycones from the anthocynanins.
Growth inhibition of HT-29 cells exposed to 10, 25, and 50 µg/ml chokeberry ARE, 10, 25, 50 and 75 µg/ml of purified chokeberry anthocyanin fraction and 5, 10, 25, 50 and 75 µg/ml of purified chokeberry aglycon was studied at two time points of 24 and 48 h. The concentrations were based on monomeric anthocyanin content of the extract added per ml of media. Typical purification procedures for AREs are described in Examples 4 and 5. Cell preparation, maintenance and testing are described in Examples 1-5.
As observed in FIG. 14A chokeberry purified anthocyanin fraction demonstrated slightly higher percentage of inhibition of HT-29 cells. The difference is clearly observed at 50 µg/ml concentration and 24 h time point. The decreased inhibition of cells after 48 h with chokeberry ARE as compared to 24 h may be due to experimental error. FIG. 14B demonstrates that the purified fraction of aglycon (mainly cyanidin in chokeberry ARE) also has the ability to inhibit the growth of HT-29 cells.
Growth inhibition of HT-29 cells exposed to 25, 50 and 75 µg/ml and 10, 25, 50 and 75 µg/ml of purified bilberry anthocyanin fraction was studied at two time points of 24 and 48 h. The concentrations were based on monomeric anthocyanin content of the extract added per ml of media.
As observed in FIG. 14C, bilberry purified anthocyanin fraction demonstrated a much higher percentage of inhibition of HT-29 cells. The inhibition observed at 75 µg/ml concentration clearly demonstrates that the percentage of cells inhibited increase almost 2-fold when exposed to the purified anthocyanin fraction of bilberry ARE.
Therefore, the main findings of these experiments are that purified anthocyanins of bilberry and chokeberry ARE are as effective as the complete ARE in inhibiting the growth of HT29 cells and that the inhibition of HT29 by aglcyons (anthocyanidins) of chokeberry anthocyanins is similar to that of the purified anthocyanins in chokeberry ARE.
The patent and scientific literature referred to herein establishes the knowledge that is available to those with skill in the art. All United States patents and published or unpublished United States patent applications cited herein are hereby incorporated by reference. All published foreign patents and patent applications cited herein are hereby incorporated by reference. All other published references, documents, manuscripts and scientific literature cited herein are hereby incorporated by reference.
While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting the growth and cell cycle progression of colon carcinoma cells comprising the step of contacting the cells with an anthocyanin-rich extract in an amount effective to inhibit the growth and cell cycle progression of the colon carcinoma cells without affecting the growth and cell cycle progression of normal colon cells wherein the anthocyanin extract is derived from chokeberries and wherein at least 70% of the total anthocyanins in the chokeberry anthocyanin-rich extract are cyanidin-3-galactoside.

* * * * *